United States Patent [19]
Korsmeyer

[11] Patent Number: 5,955,593
[45] Date of Patent: Sep. 21, 1999

[54] BH3 INTERACTING DOMAIN DEATH AGONIST

[75] Inventor: Stanley J. Korsmeyer, Clayton, Mo.

[73] Assignee: Washington University, St. Louis, Mo.

[21] Appl. No.: 08/706,741

[22] Filed: Sep. 9, 1996

[51] Int. Cl.⁶ ............................ C07H 21/04; C07H 21/02
[52] U.S. Cl. ....................... 536/23.5; 536/23.1; 536/23.4; 435/69.1; 435/69.7; 435/71.1; 514/12; 530/350
[58] Field of Search ................................ 514/44; 536/23.1

[56] References Cited

PUBLICATIONS

Oltvai and Korsmeyer, Checkpoints of Dueling Dimers Foil Death Wishes, *Cell* 79:189–192, 1994.
Korsmeyer, Bcl–2 Initiates a New Category of Oncogenes: Regulators of Cell Death, *Blood* 80:879–886, 1992.
Zha et al., Proapoptotic Protein Bax Heterodimerizes with Bcl–2 and Homodimerizes with Bax via a Novel Domain (BH3) Distinct from BH1 and BH2, *J. Biol. Chem.* 271:7440–7444, 1996.
Boyd et al., Bik, a novel death–inducing protein shares a distinct sequence motif with Bcl–2 family proteins and interacts with viral and cellular survival–promoting proteins, *Oncogene* 11:1921–1928, 1928.
Chittenden et al., A conserved domain in Bak, distinct from BH1 and BH2, mediates cell death and protein binding functions, *Embo. J.* 14:5589–5596, 1995.
Boise et al., bcl–x, a bcl–2–Related Gene That Functions as a Dominant Regulator of Apoptotic Cell Death, *Cell* 74:597–608, 1993.
Han et al., The E1B 19K protein blocks apoptosis by interacting with and inhibiting the p53–inducible and death–promoting Bax protein, *Genes & Dev.* 10:461–477, 1996.
Hunter and Parslow, A Peptide Sequence from Bax That Converts Bcl–2 into an Activator of Apoptosis, *J. Biol. Chem.* 271:8521–8524, 1996.
Trofatter et al, An Expression–independent Catalog of Genes from Human Chromosome 22, *Genome Res.* 5:214–224, Nov. 20, 1995.
Hillier et al. Accession No: RO9650. GenBank, Est. Jun. 6, 1995.
Trofatter et al. Accession No: H55483. GenBank, Est. Dec. 7, 1995 as shown on pages 3–4 of MPSRCH for US–08–706–741A–1.

*Primary Examiner*—Paula K. Hutzell
*Assistant Examiner*—Timothy A. Worrall
*Attorney, Agent, or Firm*—Howell & Haferkamp, L.C.

[57] ABSTRACT

A novel death agonist, BID, which is related to the BCL-2 family of apoptosis regulating proteins only in the conserved BH3 domain, is provided along with encoding polynucleotides. BID polypeptides and derivatives thereof are useful in modulating apoptosis. Polynucleotides encoding BID polypeptides and derivatives thereof are useful as templates for recombinantly expressing BID polypeptides, as probes for detecting endogenously expressed BID polynucleotides, and in gene therapy for treating or preventing disease. Methods for modulating inappropriate expression of BID using BID antisense molecules or anti-BID antibodies are also provided. In addition, screening assays for identifying agents which modulate binding between BID and other BCL-2 family members are provided.

16 Claims, 28 Drawing Sheets

FIGURE 1A. hBID (SEQ ID NO:1)

```
      ATGGA CTGTGAGGTC AACAACGGTT CCAGCCTCAG GGATGAGTGC ATCACAAACC
TACTGGTGTT TGGCTTCCTC CAAAGCTGTT CTGACAACAG CTTCCGCAGA GAGCTGGACG
CACTGGGCCA CGAGCTGCCA GTGCTGGCTC CCCAGTGGGA GGGCTACGAT GAGCTGCAGA
CTGATGGCAA CCGCAGCAGC CACTCCCGCT GGGAAGAAT AGAGGCAGAT TCTGAAAGTC
AAGAAGACAT CATCCGGAAT ATTGCCAGGC ACCTCGCCCA GGTCGGGGAC AGCATGGACC
GTAGCATCCC TCCGGGCCTG GTGAACGGCC TGGCCCTGCA GCTCAGGAAC ACCAGCCGGT
CGGAGGAGGA CCGGAACAGG GACCTGGCCA CTGCCCTGGA GCAGCTGCTG CAGGCCTACC
CTAGAGACAT GGAGAAGGAG AAGACCATGC TGGTGCTGGC CCTGCTGCTG GCCAAGAAGG
TGGCCAGTCA CACGCCGTCC TTGGCTCCGT GATGTCTTTC ACACAACAGT AATTTTATTA
ACCAGAACCT ACGCACCTAC GTGAGGAGCT TAGCCAGAAA TGGGATGGAC TGA
```

FIGURE 1B. hBID VARIANT (SEQ ID NO:2)

```
      ATGGA CTGTGAGGTC AACAACGGTT CCAGCCTCAG GGATGAGTGC ATCACAAACC
TACTGGTGTT TGGCTTCCTC CAAAGCTGTT CTGACAACAG CTTCCGCAGA GAGCTGGACG
CACTGGGCCA CGAGCTGCCA GTGCTGGCTC CCCAGTGGGA GGGCTACGAT GAGCTGCAGA
CTGATGGCAA CCGCAGCAGC CACTCCCGCT GGGAAGAAT AGAGGCAGAT TCTGAAAGTC
AAGAAGACAT CATCCGGAAT ATTGCCAGGC ACCTCGCCCA GGTCGGGGAC AGCATGGACC
GTAGCATCCC TCCGGGCCTG GTGAACGGCC TGGCCCTGCA GCTCAGGAAC ACCAGCCGGT
CGGAGGAGGA CCGGAACAGG GACCTGGCCA CTGCCCTGGA GCAGCTGCTG CAGGCCTACC
CTAGAGACAT GGAGAAGGAG AAGACCATGC TGGTGCTGGC CCTGCTGCTG GCCAAGAAGG
TGGCCAGTCA CACGCCGTCC TTGGCTCCGT GATGTCTTTC ACACAACAGT AATTTTATTA
ACCAGAACCT ACGCACCTAC GTGAGGAGCT TAGCCAGAAA T<u>GTAAGAACC CTTGAGGGGA
TGGACTGA</u>
```

FIGURE 1C. mBID (SEQ ID NO:3)

```
ATGGACTCTG AGGTCAGCAA CGGTTCCGGC CTGGGGGCCA AGCACATCAC AGACCTGCTG
GTGTTCGGCT TTCTCCAAAG CTCTGGCTGT ACTCGCCAAG AGCTGGAGGT GCTGGGTCGG
GAACTGCCTG TGCAAGCTTA CTGGGAGGCA GACCTCGAAG ACGAGCTGCA GACAGACGGC
AGCCAGGCCA GCCGCTCCTT CAACCAAGGA AGAATAGAGC CAGATTCTGA AAGTCAGGAA
GAAATCATCC ACAACATTGC CAGACATCTC GCCCAAATAG GCGATGAGAT GGACCACAAC
ATCCAGCCCA CACTGGTGAG ACAGCTAGCC GCACAGTTCA TGAATGGCAG CCTGTCGGAG
GAAGACAAAA GGAACTGCCT GGCCAAAGCC CTTGATGAGG TGAAGACAGC CTTCCCCAGA
GACATGGAGA ACGACAAGGC CATGCTGATA ATGACAATGC TGTTGGCCAA AAAAGTGGCC
AGTCACGCAC CATCTTTGCT CCGTGATGTC TTCCACACGA CTGTCAACTT TATTAACCAG
AACCTATTCT CCTATGTGAG GAACTTGGTT AGAAACGAGA TGGACTGA
```

```
huBid  - MDCEVNNGSSLRDECITNLLVFGFLQSCSDNSFRRELDALGHELPVLAPQ  - 50
          ||||||| ||| ||  || ||||||||||| ||   |  || ||||
muBid  - MDSEVSNGSSLGAKHITDLLVFGFLQSSG--CTRQELEVLGRELPV-QAY  - 47

BH3
huBid  - WEGY--DELQTDGNRSSHS-RLGRIEADSESQEDIIRNIARHLAQVGDSM  - 97
         ||    ||||||||  |  ||||| |||||||||  |||||||||| ||
muBid  - WEADLEDELQTDGSQASRSFNQGRIEPDSESQEEIIHNIARHLAQIGDEM  - 97
                             ‾‾‾‾‾‾‾‾‾‾‾‾‾‾‾‾‾‾
                                  Peptide 1 huBid  - DRSIPPGLVNGLALQLRNTSRSEEDRNRDLATALEQLLQAYPRDMEKEKT  - 147
         ‾   |  |  |  ||  ||  |||| ||||||  || |||||||| | |
muBid  - DHNIQPTLVRQLAAQFMNGSLSEEDKRNCLAKALDEVKTAFPRDMENDKA  - 147
                                       ‾‾‾‾‾‾‾‾‾‾‾‾‾‾‾‾‾‾‾‾
                                              Peptide 2 huBid  - MLVLALLLAKKVASHTPSLLRDVFHTTVNFINQNLRTYVRSLARNGMD  -195
         ||   ||||||||||| || |||||||||||||||||  ||| ||||
muBid  - MLIMTMLLAKKVASHAPSLLRDVFHTTVNFINQNLFSYVRNLVRNEMD  -195
```

|  | start | | | | | BH3 | | | | | | | | | end |
|---|---|---|---|---|---|---|---|---|---|---|---|---|---|---|---|
| hBak | 76 | R | Q | L | A | I | G | D | D | I | N | R | R | | 88 |
| mBax | 61 | E | C | L | R | - | G | D | E | L | D | S | N | | 73 |
| hBik | 59 | L | L | A | C | I | G | D | D | M | V | V | S | | 71 |
| mBid | 88 | R | H | L | A | Q | I | G | D | E | M | D | H | N | 100 |

| | | | | | | | | | | | | | |
|---|---|---|---|---|---|---|---|---|---|---|---|---|---|
| Bid-wt      | – | – | – | – | – | – | – | – | – | – | – | – | – |
| Bid-mIII-1  | – | – | – | – | – | – | – | A | A | – | – | – | – |
| Bid-mIII-2  | – | – | – | – | A | A | A | A | – | – | – | – | – |
| Bid-mIII-3  | – | – | – | – | – | A | – | – | – | – | – | – | – |
| Bid-mIII-4  | – | – | – | – | – | E | – | – | – | – | – | – | – |

Hours of Induction: 0 12 24 36 54
BIDmIII-1 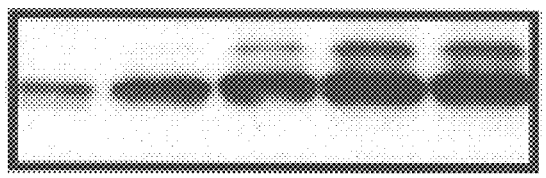
BIDmIII-2 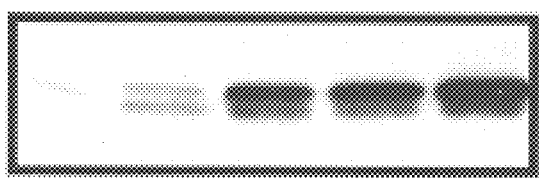
BIDmIII-3 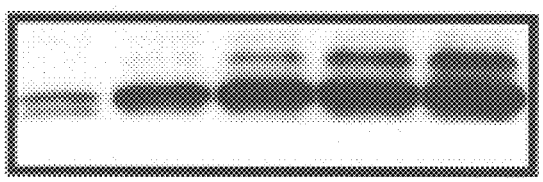
BIDmIII-4 
FIGURE 11B peptide A

NH2- YGRKKRRQRRR G DSESQEEIIHNIARHLAQIGDEMDHNIQPTLV -COOH (Tat peptide)    (murine BID aa75-106)

peptide B

NH2- YGRKKRRQRRR G EIIHNIARHLAQIGDEMDHN -COOH (Tat peptide)    (murine BID aa81-100)

peptide C

NH2- YGRKKRRQRRR G HNIARHLAQIGDEMD -COOH (Tat peptide)    (murine BID aa84-98)

| | | | | | | | | |
|---|---|---|---|---|---|---|---|---|
| Bcl-2 | 97 | L | R | Q | A | G | D | D | F | S | 105 |
| Bax | 63 | L | K | R | I | G | D | E | L | D | 71 |
| Bcl-x | 90 | L | R | E | A | G | D | E | F | E | 98 |
| Bak | 77 | L | A | I | I | G | D | D | I | N | 85 |
| Mcl1 | 213 | L | R | R | V | G | D | G | V | Q | 221 |
| Ced-9 | 116 | M | R | V | M | G | T | I | F | E | 124 |
| A1 | | | | | | | | | | |
| Bad | | | | | | | | | | |
| LMW5-HL | | | | | | | | | | |
| BHRF1 | | | | | | | | | | |
| Bik | 61 | L | A | C | I | G | D | E | M | D | 69 |
| Bid | 90 | L | A | Q | I | G | D | E | M | D | 98 |

| | | | | | | | | | | | |
|---|---|---|---|---|---|---|---|---|---|---|---|
| Bcl-2 | 133 | D | G | - | V | N | W | G | R | I | V | A | 142 |
| Bax | 102 | D | G | N | F | N | W | G | R | V | V | A | 112 |
| Bcl-x | 140 | D | G | - | V | N | W | G | R | I | V | A | 149 |
| Bak | 121 | S | G | - | I | N | W | G | R | V | V | A | 130 |
| Mcl1 | 256 | D | G | V | T | N | W | G | R | I | V | T | 266 |
| Ced-9 | 164 | C | P | - | M | S | Y | G | R | L | I | G | 173 |
| A1 | 81 | D | G | - | I | N | W | G | R | I | V | T | 91 |
| Bad | 142 | W | A | A | Q | R | Y | G | R | E | L | R | 152 |
| LMW5-HL | 80 | D | L | - | I | N | W | G | R | I | C | G | 89 |
| BHRF1 | 93 | R | G | D | P | S | L | G | R | A | L | A | 103 |

| | | | | | | | | | |
|---|---|---|---|---|---|---|---|---|---|
| Bcl-2 | 188 | W | I | Q | D | N | G | G | W | D | 196 |
| Bax | 151 | W | I | Q | D | Q | G | G | W | D | 159 |
| Bcl-x | 181 | W | I | Q | E | N | G | G | W | D | 189 |
| Bak | 170 | W | I | A | Q | R | G | G | W | V | 178 |
| Mcl1 | 305 | W | L | V | K | Q | R | G | W | D | 313 |
| Ced-9 | 214 | W | K | E | H | N | R | S | W | D | 222 |
| A1 | 133 | W | I | R | G | N | G | G | W | E | 141 |
| Bad | 183 | W | T | R | I | - | Q | S | W | D | 191 |
| LMW5-HL | 127 | W | M | I | S | H | G | G | W | E | 135 |
| BHRF1 | 143 | W | I | H | Q | Q | G | G | W | D | 151 |

| | | | | | | | | | | | | | | |
|---|---|---|---|---|---|---|---|---|---|---|---|---|---|---|
| Bcl-2 | 11 | N | R | E | - | - | - | - | I | V | M | K | Y | I | H | Y | K | L | S | Q | R | G | Y | E | W | 30 |
| Bcl-x | 5 | N | R | E | - | - | - | - | L | V | V | D | F | L | S | Y | K | L | S | Q | K | G | Y | S | W | 24 |
| Ced-9 | 73 | W | E | E | P | R | L | D | I | E | G | F | V | V | D | Y | F | T | H | R | I | R | Q | N | G | M | E | W | 99 |

BH3 INTERACTING DOMAIN DEATH AGONIST

REFERENCE TO GOVERNMENT GRANT

This invention was made with government support under Grant Number CA50239. The government has certain rights in this invention.

BACKGROUND OF THE INVENTION (1) Field of the Invention

This invention relates generally to the regulation of apoptosis and to polypeptides, including both antagonists and agonists, which regulate apoptosis as well as to polynucleotides encoding these polypeptides, and, more particularly, to the novel death agonist, BID and the polynucleotide encoding BID.

(2) Description of the Related Art

Programmed cell death, referred to as apoptosis, plays an indispensable role in the development and maintenance of homeostasis within all multicellular organisms (Raff, *Nature* 356: 397–400, 1992 which is incorporated by reference). Genetic and molecular analysis from nematodes to humans has indicated that the apoptotic pathway of cellular suicide is highly conserved (Hengartner and Horvitz, *Cell* 76: 1107–1114, 1994 which is incorporated by reference). In addition to being essential for normal development and maintenance, apoptosis is important in the defense against viral infection and in preventing the emergence of cancer.

Considerable progress has been made in identifying the molecules that regulate the apoptotic pathway at each level. Of note, both positive and negative regulators, often encoded within the same family of proteins, characterize the extracellular, cell surface and intracellular steps (Oltvai and Korsmeyer, *Cell* 79: 189–192, 1994 which is incorporated by reference).

One such family of proteins that constitutes an intracellular checkpoint of apoptosis is the BCL-2 family of proteins. The founding member of this family is the apoptosis-inhibiting protein encoded by the bcl-2 protooncogene which was initially isolated from a follicular lymphoma (Bakhshi et al., *Cell* 41: 889–906, 1985; Tsujimoto et al, *Science* 229: 1390–1393, 1985; Cleary and Sklar, *Proc Natl Acad Sci USA* 82: 7439–7443, 1985 which are incorporated by reference). The BCL-2 protein is a 25 kD, integral membrane protein of the mitochondria. This factor extends survival in many different cell types by inhibiting apoptosis elicited by a variety of death-inducing stimuli (Korsmeyer, *Blood* 80: 879–886, 1992 which is incorporated by reference).

The family of BCL-2-related proteins has been defined by sequence homology that is largely based upon conserved motifs termed bcl-homology domains. (Yin et al, *Nature* 369: 321–323, 1994 which is incorporated by reference). Bcl-homology domains 1 and 2 (BH1 and BH2) domains have been shown to be important in dimerization and in modulating apoptosis (Yin et al., *Nature* 369: 321–323, 1994 which is incorporated by reference). A third homology region, BH3, has also been identified as important to dimerization as well as apoptosis (Boyd et al., *Oncogene* 11: 1921–1928; Chittenden et al., *Embo J* 14: 5589–5596, 1995 which are incorporated by reference) as has been a fourth homology region, BH4, near the amino terminal end of some family members (Farrow and Brown, *Curr Opin Genet Dev* 6: 45–49, 1996 which is incorporated by reference)(see FIGS. 13A–13E).

Members of this family can heterodimerize and, in most cases, homodimerize as well. The ratio of death antagonists (BCL-2, BCL-$X_L$, MCL-1 and A1) to agonists (BAX, BAK, BCL-$X_S$ and BAD) determines which homodimers or heterodimers are formed and the balance of these is believed to determine whether a cell will respond to an apoptotic signal (Oltvai and Korsmeyer, *Cell* 79: 189–192, 1994 which is incorporated by reference). Thus, dimerization between agonists and antagonists is competitive. For example, the death promoting molecule BAX forms homodimers that favor death whereas BAX will also form heterodimers with BCL-2 or BCL-$X_L$ (Oltvai et al., *Cell* 74: 609–619, 1993 which is incorporated by reference) and the formation of these heterodimers results in inhibition of cell death. Mutagenesis studies have revealed that intact BH1 and BH2 domains of the antagonists (BCL-2, BCL-$X_L$) are required for them to heterodimerize with BAX and to repress cell death (Yin et al., *Nature* 369: 321–323, 1994; Sedlak et al. 1995 which are incorporated by reference). Conversely, deletion analysis has indicated that the BH3 domain of death agonists (BAK, BAX) is required for them to heterodimerize with BCL-$X_L$ or BCL-2 and to promote cell death (Chittenden et al., *Embo J* 14: 5589–5596, 1995; Zha et al. 1996 which are incorporated by reference). However, other mutations in BCL-$X_L$ have been noted to disrupt heterodimerization with BAX, but retain death repressor activity (Cheng et al., *Nature* 379: 554–556, 1996 which is incorporated by reference). This suggests that these molecules might also work independent of one another. Recently, the first X-ray and multidimensional NMR structure of a family member, BCL-$X_L$, was determined (Muchmore et al., *Nature* 381: 335–341, 1996 which is incorporated by reference). It was found that α helices correspond to the BH1–BH4 domains and that a hydrophobic pocket results from the close spatial proximity of the BH1, BH2 and BH3 domains.

The BH3 domain may play a role in the promotion of death by some of the death agonists although in others such as BAD the BH3 domain is not present. An important role for the BH3 domain has been suggested for death agonist family members that lack both the BH1 and BH2 domains, but have a BH3 domain. One such family member is BCL-$X_S$. This protein, which is translated from an alternatively spliced version of the mRNA encoding BCL-$X_L$, inhibits the ability of BCL-2 protein to enhance the survival of growth-factor deprived cells (Boise et al. *Cell* 74: 597–608, 1993 which is incorporated by reference). BCL-$X_S$ also contains a BH4 homology region as does BCL-$X_L$.

BIK is another death agonists having a BH3 but not BH1 or BH2 domains and this protein also lacks a BH4 domain (Boyd et al., *Oncogene* 11: 1921–1928, 1995 which is incorporated by reference). Like the classic family members such as BCL-2 itself, this protein has a C-terminal hydrophobic domain which appears to function as a signal/anchor segment to enable transmembrane localization (Nguyen et al., *J Biol Chem* 268: 25265–25268, 1993 which is incorporated by reference).

The BH3 domain of BAK, an agonist with BH1, BH2 BH3 and C-terminal membrane localization domains, has been postulated to be of central importance in mediating the cell death promoting effect of this family member. This conclusion was based upon deletion studies which identified the BH3 region as necessary for induction of cell-death and upon the retention of cell killing activity by a 50 amino acid polypeptide fragment including BH3 but excluding BH1 and BH2 which indicated that the BH3 domain is sufficient for eliciting cell death.

Some disease conditions are believed to be related to the development of a defective down-regulation of apoptosis in the affected cells. For example, neoplasias may result, at least in part, from an apoptosis-resistant state in which cell proliferation signals inappropriately exceed cell death signals. Furthermore, some DNA viruses such as Epstein-Barr virus, African swine fever virus and adenovirus, parasitize the host cellular machinery to drive their own replication and at the same time modulate apoptosis to repress cell death and allow the target cell to reproduce the virus. Moreover, certain disease conditions such as lymphoproliferative conditions, cancer including drug resistant cancer, arthritis, inflammation, autoimmune diseases and the like may result from a down regulation of cell death regulation. In such disease conditions it would be desirable to promote apoptotic mechanisms and one advantageous approach might involve treatment with a cell death agonists having a BH3 domain which has been identified as being an important agonist determinant.

Furthermore, in certain disease conditions it would be desirable to inhibit apoptosis such as in the treatment of immunodeficiency diseases, including AIDS, senescence, neurodegenerative disease, ischemic and reperfusion cell death, infertility, wound-healing, and the like. In the treatment of such diseases it would be desirable to diminish the cell death agonist activity of endogenous proteins containing BH3 domains. Thus it would be desirable to identify new members of the BCL-2 family which have cell-death agonist properties by virtue of the presence of a BH3 domain and to utilize these as a basis for treatment modalities in advantageously modulating the apoptotic process in disease conditions involving either inappropriate repression or inappropriate enhancement of cell death.

SUMMARY OF THE INVENTION

Briefly, therefore, the present invention is directed to the identification, isolation and use of substantially purified proteins and encoding polynucleotides which belong to the BCL-2 family of apoptosis regulating proteins. Accordingly, the inventor herein has succeeded in discovering a new cell-death agonist which contains only the BH3 domain in common with the BCL-2 family. This new death agonist referenced herein as BID (BH3 Interacting domain Death agonist) includes, sequences which are related to the BCL-2 family only in the BH3 domain. BID has a sequence deduced from the BID cDNA of 195 amino acid with a predicted molecular weight of 21.95 kDa. BID cDNA molecule identified and isolated herein include the human polynucleotide (SEQ ID NO: 1) which encodes the human BID polypeptide (SEQ ID NO: 4) and the mouse polynucleotide (SEQ ID NO: 3) which encodes the mouse BID polypeptide (SEQ ID NO: 6). Human BID cDNA has also been discovered to exist in a variant form which contains an additional 15 nucleotides near the 3' end (SEQ ID NO: 2) and which encodes a human BID polypeptide having 200 amino acids (SEQ ID NO: 5).

It has been unexpectedly discovered that BID heterodimerizes with both the death antagonists, BCL-2 and BCL-$X_L$, and the death agonist, BAX using in vivo and in vitro binding assays as well as yeast two-hybrid assays. BID over expression can induce apoptotic death as well as counter protection by BCL-2 and activates the common pathway of apoptosis including cysteine proteases (Martin and Green, Cell 82: 349–352, 1995; Henkart, Immunity 4: 195–201, 1996 which are incorporated by reference).

BID's only homology with the BCL-2 family is a conserved BH3 domain which is required for heterodimerization with its partners and for its death promoting activity. BID lacks the typical carboxyl-terminal signal-anchor segment and has both cytosolic and membrane locations. Mutagenesis of BH3 revealed the importance of BID/BAX heterodimers and indicated that BID serves as a death agonist ligand.

The present invention, therefore, provides novel compositions and methods for modulating cell death using BID polynucleotide sequences and BID polypeptide sequences as well as methods for identifying agents which can modulate cell death.

Accordingly, in one embodiment of the present invention, an isolated and substantially purified mammalian BID polypeptide is provided and fragments thereof. The BID polypeptides of the present invention are substantially identical to naturally occurring sequences which are believed to have at least about 85% sequence identity among orthologs from different mammalian species and can be identified by virtue of their (a) lacking the carboxyl terminal signal-anchor sequence characteristic of the membrane bound members of the BCL-2 family, (b) lacking the BH1 and BH2 domains, (c) possessing the amino acid sequence of a BH3 domain and (d) selectively heterodimerizes with BAX, BCL-2 and BCL-$X_L$. In one embodiment, the BH3 domain of BID polypeptides is comprised of the sequence: Leu-Ala-Gln-$Xaa_1$-Gly-Asp-$Xaa_2$, where $Xaa_1$ is Ile or Val and $Xaa_2$ is Glu or Ser (SEQ ID NO: 7) and more particularly a BH3 domain of human BID is comprised of the sequence Leu-Ala-Gln-Val-Gly-Asp-Ser-Met-Asp (SEQ ID NO: 8). The BID polypeptide is substantially identical to a human BID polypeptide (SEQ ID NOS: 4 and 5) or to a murine BID polypeptide (SEQ ID NO: 6) or to a derivative thereof or a fragment or fusion protein thereof.

The invention also provides modified BID polypeptides comprising a BH3 domain and an overall sequence with amino acid substitution, addition and/or deletion compared to one of the naturally-occurring BID sequences (SEQ ID NOS: 4–6) or a fragment thereof. Such modified BID polypeptides can show either death agonist activity as the naturally-occurring BID polypeptides, or altered biological activity from the native protein, or antagonist activity to block the effect of naturally-occurring BID polypeptides.

In another embodiment, the present invention also provides polynucleotides encoding BID polypeptides. Such polynucleotides can serve as templates for the recombinant expression of quantities of BID polypeptides or as probes in detection assays in which the polynucleotides hybridize to endogenous BID polynucleotides such as in Northern blot analysis.

The present invention also provides vectors comprising a recombinant DNA molecule comprising expression regulatory elements operably linked to a nucleic acid sequence encoding a BID polypeptide.

Another embodiment provides for screening assays for identifying agents which modulate of inhibit the binding of BID to BAX, BCL-2 or BCL-$X_L$ or other BCL-2 family members.

The present invention also provides for antisense polynucleotides complementary to polynucleotides encoding BID polypeptide sequences. Such antisense polynucleotides are employed to inhibit transcription and/or translation of the BID polypeptide mRNA and thereby effect a reduction in the amount of the respective BID polypeptide in a cell. As such, the antisense polynucleotides can inhibit apoptotic cell death.

The polynucleotides of the present invention can also be used in diagnostic assays for pathological conditions or genetic diseases that involve neoplasia or other disease condition related to BID function, specifically, conditions and diseases that involve alterations in the structure or abundance of a BID polypeptide, RNA transcript or splicing intermediate, mRNA, or genomic gene locus.

The present invention also provides antibodies which bind to BID and which are selective over related BCL-2 family members for use in diagnostic assays to detect any altered expression of BID polypeptides such as in degenerative, senescent, preneoplastic, hyperplastic, or neoplastic cells or to follow the course of a particular disease. The BID antibodies can also be used in the treatment of inappropriate or overexpression of BID polypeptides.

In another aspect of the present invention, non-human animals such as mice are provided including knockout animals having a homozygous pair of functionally disrupted endogenous BID genes. Also included are transgenic non-human animals or cells from humans or non-human animals with a transgene encoding a BID polypeptide.

The present invention also provides methods and compositions for gene therapy using BID polynucleotides and BID gene therapy vectors for treating or preventing disease.

In another embodiment, the present invention provides methods for treating diseases in which cell death is inappropriately inhibited in conditions such as neoplasia or autoimmunity. Such methods involve treatment with a BID polypeptide or fragment thereof or fusion protein or peptidomimetic of BID. Also provided are methods for treating diseases in which BID is over expressed or inappropriately expressed, the methods comprising administration of BID antisense molecules or BID antibody or substance that binds and neutralizes BID. Alternatively, mutant forms of BID can be administered to counter endogenous BID activity.

The present invention also provides pharmaceutical compositions, which contain pharmaceutically effective amounts of a BID polypeptide or a BID polynucleotide and a suitable pharmaceutical carrier or delivery system.

Among the several advantages found to be achieved by the present invention, therefore, may be noted the provision of the new death agonist, BID which contains only the BH3 domain in common with the BCL-2 family of proteins and derivatives of the BID polypeptide as well as fragments thereof which can promote cell death in cells with an inappropriately repressed apoptotic state such as in neoplasia or autoimmunity; the provision bid polynucleotides and derivatives thereof which encode BID polypeptides; the provision of methods for treating disease conditions mediated by a repressed apoptotic state using BID polypeptides or derivatives thereof or fragments thereof; the provision of methods for modulating overexpression or inappropriate expression of BID using BID antisense molecule or BID antibodies; the provision of methods for detecting and monitoring BID polypeptide levels in cells or in a patient; and the provision of methods for detecting alterations in a BID gene.

BRIEF DESCRIPTION OF THE DRAWINGS

FIGS. 1A–C illustrate full-length cDNA Sequence: FIG. 1A is human BID (SEQ ID NO: 1), FIG. 1B is a variant of human BID (SEQ ID NO: 2) having an additional 15 nucleotides near the 3' end as indicated by underline, and FIG. 1C is murine BID (SEQ ID NO: 3);

FIG. 2 illustrates the aligned human and murine BID polynucleotides with the BH3 domain overlined and two murine polypeptide epitopes which were able to elicit antibodies, underlined;

(FIG. 8B) in in vitro binding of [$^{35}$S]Met labeled BCL-$X_L$, BCL-2, BAX or BID with purified GST-BID or GST control; (FIG. 8C) in in vitro binding of [$^{35}$S]Met labeled BCL-2 and BAX mutants with GST-BID; and (FIG. 8D) in in vitro binding of [$^{35}$S] Met labeled pre-associated BCL-2 wt and BAX mutants with GST-BID;

FIG. 9A–B illustrates (FIG. 9A) the alignment of BH3 domains of death promoting molecules (human BAK, murine BAX, human BIK and murine BID, SEQ ID NOS: 38–41 represented with two upstream and two downstream amino acids, SEQ ID NOS: 42–45) and schematic representation of mutations introduced into BID (SEQ ID NOS: 46–49) and (FIG. 9B) in vitro binding of BCL-2 or BAX with GST-BID or BID mutants;

FIGS. 11A–C illustrates (FIG. 11A) the viability of Jurkat cells expressing wild type and BH3-domain mutant BID; (FIG. 11B) Western blot showing levels of BID polypeptides; and (FIG. 11C) viability measured in luciferase activity in Rat-1 fibroblasts co-transfected with luciferase reporter gene and with bcl-2, bcl-2 along with bid and with wild type and BH3-domain mutant bid;

FIGS. 12A–C illustrate (FIG. 2A) the full-length and truncated murine BID polypeptides with primers used to generate truncated polypeptides indicated by arrows and the amino acid of full-length murine BID for each of the truncated polypeptides (SEQ ID NOS: 50–53), (FIG. 12B)

Figure 3:
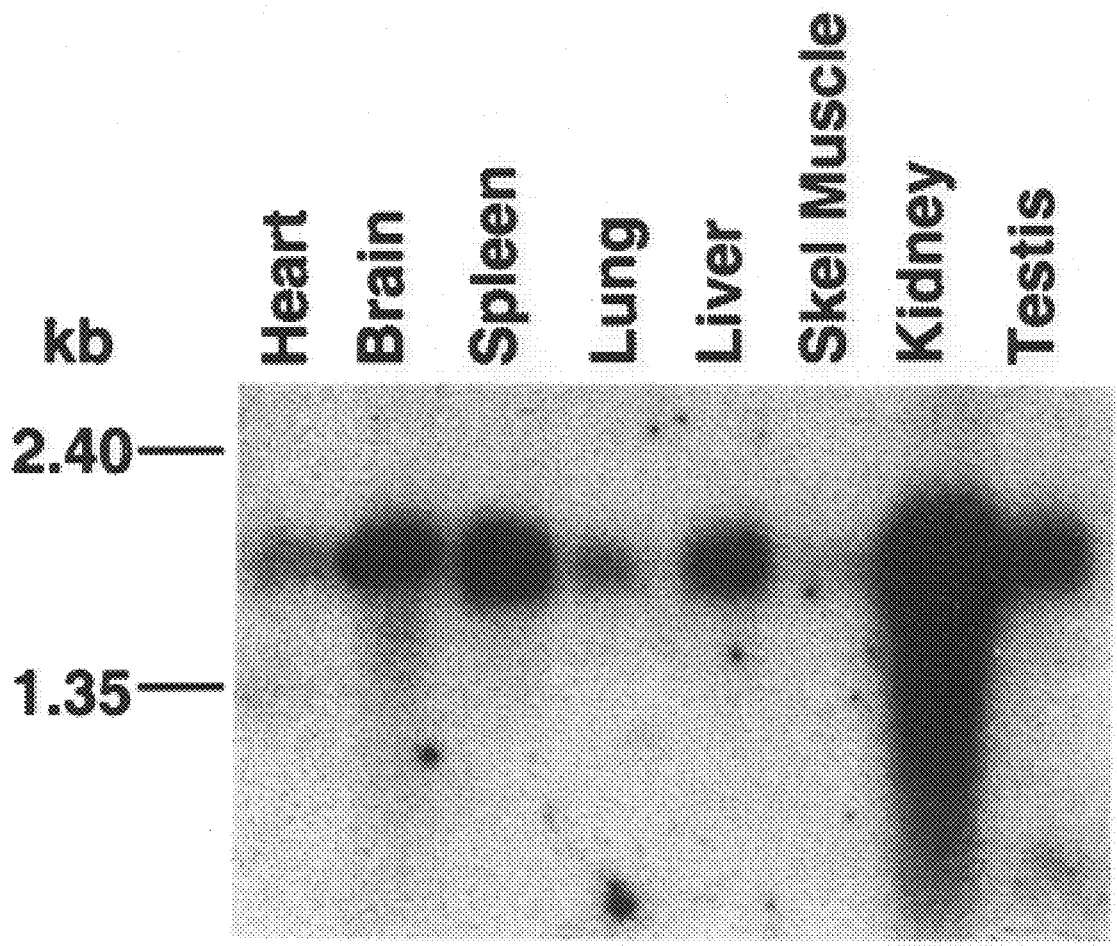
FIG. 3 illustrates the Northern blot analysis in adult mouse tissues using a radiolabeled murine Bid cDNA containing the open reading frame as a probe.

the Tat-BH3 fusion protein (SEQ ID NO: 56) containing the HIV-1 tat protein (SEQ ID NO: 54) and the BH3 domain encompassing polypeptides of amino acids 75–106 (peptide A), 81–100 (peptide B) and 84–98 (peptide C) of murine BID (SEQ ID NOS: 55, 85, and 86, respectively) and (FIG. 12C) the decrease in viability in 2B4 cells treated with 100 μm Tat-BID(75–106) (peptide A; SEQ ID NO: 56) and 100 μm Tat-BID (81–100) (peptide B; SEQ ID NO: 87).

FIGS. 13A–E illustrate (FIG. 13A) the BH1, BH2, BH3, BH4 and transmembrane domains of BID and BCL-2 family members and comparison of the sequences of (FIG. 13B) BH3 (SEQ ID NOS: 38, 40, 41, and 57–61), (FIG. 13C) BH1 (SEQ ID NOS: 62–71), (FIG. 13D) BH2 (SEQ ID NOS: 72–81) and (FIG. 13E) BH4 domains (SEQ ID NOS: 82–84).

DESCRIPTION OF THE PREFERRED EMBODIMENTS

The present invention is based upon the discovery, isolation and identification of a new BCL-2 family member, BID, including both bid polynucleotides and the deduced BID polypeptides encoded by the polynucleotides. Surprising, the BID polypeptides have been discovered to be able to heterodimerize with the death agonist, BAX and the death antagonists, BCL-2 and BCL-$X_L$ and to promote cell death. Prior to this invention, BID was unknown and had not been identified as a discrete biologically active substance nor had it been isolated in pure form.

It is known that the development as well as the maintenance of many adult tissues is achieved by several dynamically regulated process that include cell proliferation, differentiation and programmed cell death. In the latter process, cells are eliminated by a highly characteristic suicide program termed apoptosis.

BCL-2 was first isolated at the chromosomal breakpoint of t(14;18) bearing follicular B cell lymphomas. Transgenic mice bearing a BCL-2-Ig mini-gene that recapitulates this translocation displayed a polyclonal follicular hyperplasia with a four-fold increase in resting B cells and as such B cells accumulate because of extended cell survival rather than increased proliferation.

A survey of adult tissues indicates that BCL-2 has played several roles in a variety of cell lineages. Glandular epithelium that undergoes hyperplasia or involution in response to hormonal stimuli or growth factors express BCL-2. In complex epithelium, such as the skin and gut, BCL-2 is generally restricted to stem cells and proliferation zones. Within the adult nervous system, BCL-2 is more prominent in the peripheral nervous system rather than the central nervous system. Thus, BCL-2 can be needed to save the progenitor and long-lived cells in a variety of cell lineages.

BCL-2 localizes to intracellular membranes, especially to the outer mitochondrial membrane. It associates, in vivo with a 21 kKD protein partner called BAX which shows extensive amino acid homology with BCL-2 and forms homodimers with itself and heterodimers with BCL-2 and BCL-$X_L$ in vivo. BAX is encoded by 6 exons and demonstrates a complex pattern of alternative RNA splicing that predicts a 21 kD membrane form. When BAX 5 predominates in a cell, programmed cell death is favored and the death repressor activity of BCL-2 and/or BCL-$X_L$ is countered.

The ratio of BCL-2/BAX and/or BCL-$X_L$/BAX is one determinate of cell susceptibility to death following an apoptotic stimulus. In the presence of IL-3, overexpressed BAX does not noticeably alter normal cell division or viability. BAX is present and associated with BCL-2 and/or BCL-$X_L$ prior to growth factor deprivation. BAX mRNA is expressed in normal tissues and in a variety of cell lines prior to a death induction signal. Excess BAX also counters the death repressor activity of BCL-2. When BCL-2 is in excess, cells are protected. However, when BAX is in excess and BAX homodimers dominate, cells are susceptible to apoptosis.

Nevertheless, prior mutagenesis approaches to assess whether the death agonists or antagonists were dominant in regulating apoptosis have not been entirely consistent. Select mutations within the BH1 and BH2 domains of BCL-2 or BCL-$X_L$ led to simultaneous loss of BAX binding and anti-apoptotic activity (Yin et al. 1994; Sedlak et al., *Proc Natl Acad Sci USA* 92: 7834–7838, 1995; Cheng et al., *Nature* 379: 554–556, 1996 which are incorporated by reference). This suggested that death inhibitors protect cells by binding and neutralizing death agonists like BAX. However, several BCL-$X_L$ mutations that lost interaction with BAX or BAK still retained 70–80% of their anti-apoptotic activity (Cheng et al., *Nature* 379: 554–556, 1996 which is incorporated by reference) suggesting that the death antagonist and agonist members of the family can function independently of one another.

BID which is disclosed herein, is a novel partner which surprisingly interacts with both death agonists and death antagonists of the BCL-2 family. Thus, the characteristics of BID suggest yet another model in which agonists (BAX) or antagonists (BCL-2) represent membrane bound receptors that compete for a common ligand, BID.

The basis of the present invention is the unexpected discovery of a new naturally-occurring polypeptide, BID, which contains a BH3 domain but not the BH1, BH2, BH4 or membrane anchoring domains found in members of the BCL-2 family of apoptosis modulating proteins. BID acts as a death agonist as well as acting to heterodimerize with related BCL-2 family members, specifically, binding to the death agonist, BAX, and the death antagonists BCL-2 and BCL-$X_L$.

Murine BID cDNA was identified and isolated by protein interactive cloning. Murine BCL-2 and BAX cDNAs deleted of the carboxy-terminal signal anchor segments were used to generate glutathione s-transferase, (GST)/heart muscle kinase (HMK)/BCL-2 or GST/HMK/BCL-2 fusion proteins which were labeled in vitro. Labeled proteins were used to screen a λEXlox expression library constructed from a murine T cell hybridoma line, 2B4. The same, novel gene was identified multiple times with both BCL-2 and BAX probes.

A full length murine cDNA was found to have an open reading frame of 588 nucleotides (SEQ ID NO: 3; FIG. 1A). The encoded polypeptide was deduced to contain 195 amino acids (SEQ ID NO: 6) with a predicted molecular weight of 21.95 kDa (FIG. 2A). Using the murine polynucleotide sequence, a GenBank search found two Expressed Sequence Tag (EST) human cDNA clones with substantial homology to the murine bid polynucleotide in which each EST contained overlapping portions of a full-length sequence corresponding to the presumed human BID (clone ID No.: 52055 from an infant brain cDNA library and clone I.D. No. 128065 from a fetal liver, spleen cDNA library). One of these clones was obtained and completely sequenced to obtain the human bid cDNA homolog to the murine bid cDNA (FIGS. 1A and 1C, respectively; SEQ ID NOS: 1 and 3). The human sequence obtained from this clone (infant brain cDNA) has 588 nucleotides whereas the sequence or the 128065 clone (fetal liver spleen cDNA) was presumed from the reported EST sequence to contain an extra 15 base pairs (FIG. 1B; SEQ ID NO: 2). This sequence from the 128065 clone was considered to be a variant human bid cDNA.

The polynucleotide encoded by the 588 nucleotide human bid cDNA was deduced to encode a 195 amino acid open reading frame with 72.3% homology to murine BID polypeptide, representing the human homolog (see FIG. 2).

Figure 13A:
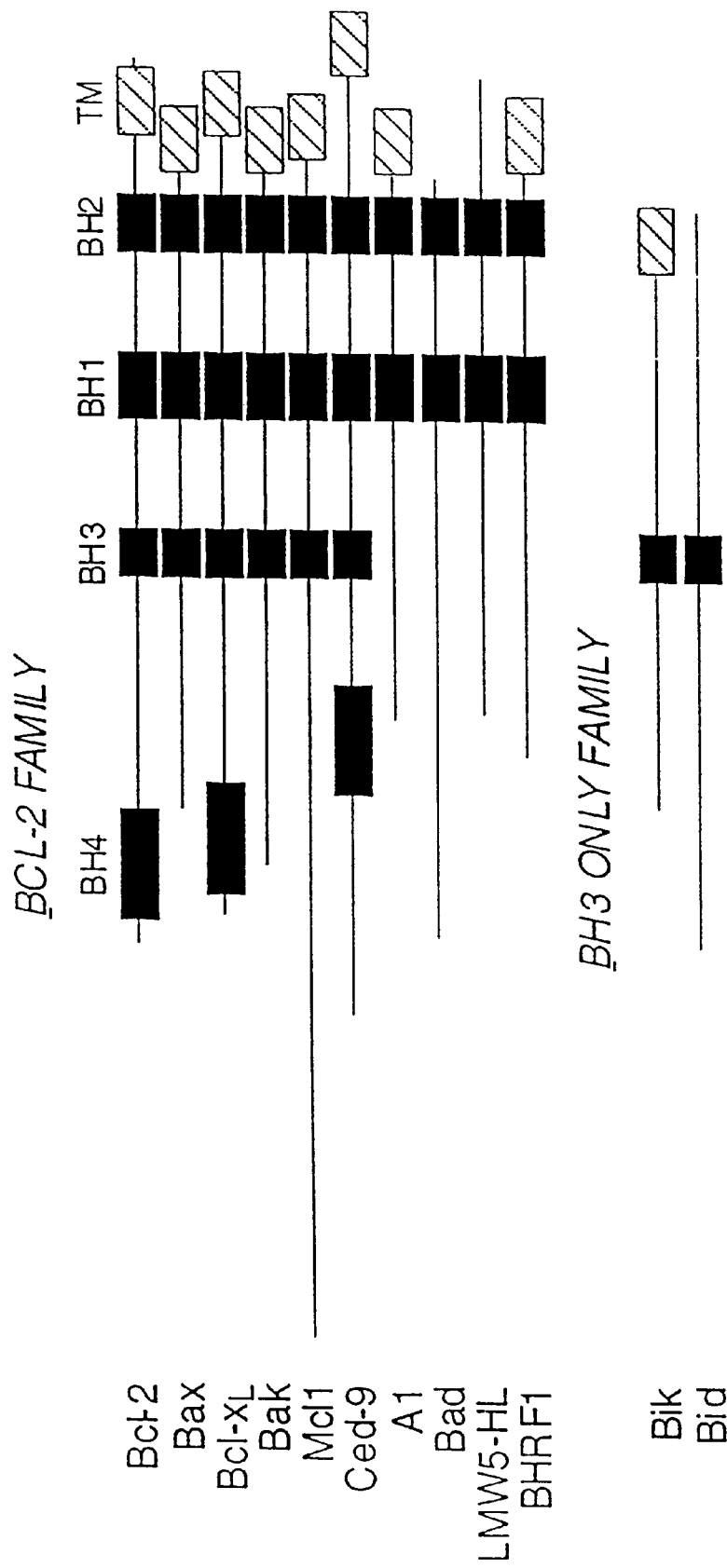

The human BID polypeptide sequences contain a region (amino acids 90–98 .(SEQ ID NO: 8) FIGS. 2, 9A and 13B) that shares high sequence homology with the well-conserved BH3 domain (Chittenden et al., *Embo J* 14: 5589–5596, 1995; Han et al., *Genes & Dev* 10: 461–477, 1996; Zha et al., *J Biol Chem* 271: 7440–7444, 1996 which are incorporated by reference) of the BCL-2 family. However, BID does not display sequence conservation with other regions of the BCL-2 family including the BH1, BH2 or BH4 domains (FIGS. 13A–E). Moreover, BID does not possess a COOH-terminal hydrophobic region typical of most BCL-2 family members which serves as a signal-anchor segment for these membrane proteins (Nguyen et al., *J Biol Chem* 268: 25265–25268, 1993 which is incorporated by reference) (FIG. 13E). Thus, BID contains only the BH3 domain of the BCL-2 family. Another death agonist BIK possesses BH3 and the COOH-terminal signal-anchor segment but also lacks recognizable BH1, 2 or 4 domains (Boyd et al., *Oncogene* 11: 1921–1928, 1995 which is incorporated by reference). Of note, BID and BIK share 8 of 9 amino acids in BH3 (FIG. 9A), but show no homology beyond this domain. In distinction, BID does not possess a COOH-terminal signal-anchor segment and resides in cytosol as well as membrane fractions.

The terms "BID" or "BID polypeptide" or "BID protein" as referenced herein is intended to be construed to include polypeptide modulators of cell death of any origin which are substantially homologous to and which are biologically equivalent to the BID polypeptides characterized and described herein. Such substantially homologous polypeptides may be native to any tissue or species and, similarly, biological activity can be characterized in any of a number of biological assay systems.

Reference to BID herein preferably includes a BID polypeptide which has at least 85 percent conservation with any one of SEQ ID NOS: 3–6 polypeptides or a bid polynucleotide encoding one such BID polypeptide; more preferably, a BID polypeptide which has at least 85 percent substantial identity to any one of SEQ ID NOS: 3–6 polypeptides or a bid polynucleotide encoding one such BID polypeptide or a bid polynucleotide which has at least 85 percent substantial identity to any one of SEQ ID NOS: 1–3 polynucleotides; even more preferably a BID polypeptide which has at least 90–95 percent conservation with any one of SEQ ID NOS: 3–6 polypeptides or a bid polynucleotide encoding one such BID polypeptide; still more preferably, a BID polypeptide which has at least 90–95 percent substantial identity to any one of SEQ ID NOS: 3–6 polypeptides or a bid polynucleotide encoding one such BID polypeptide or a bid polynucleotide which has at least 90–95 percent substantial identity to any one of SEQ ID NOS: 1–3 polynucleotides; even still more preferably, a BID polypeptide which has 100 percent conservation with any one of SEQ ID NOS: 3–6 polypeptides or a bid polynucleotide encoding one such BID polypeptide; and most preferably, a BID polypeptide which has 100 percent substantial identity to any one of SEQ ID NOS: 3–6 polypeptides or a bid polynucleotide encoding one such BID polypeptide or a bid polynucleotide which has at least 100 percent substantial identity to any one of SEQ ID NOS: 1–3 polynucleotides. Preferred bid polynucleotides are capable of hybridizing with a naturally-occurring bid polynucleotide as set forth in SEQ ID NO: 1 and/or SEQ ID NO: 2 and/or SEQ ID NO: 3. Most preferred bid polynucleotides can hybridize to a naturally-occurring bid polynucleotide under high stringency conditions (see Sambrook et al., *Molecular Cloning*, 2nd Ed., 1989 which is incorporated by reference).

The terms "biologically equivalent" are intended to mean that the compositions of the present invention are capable of demonstrating some or all of the same apoptosis promoting effects although not necessarily to the same degree as the BID polypeptide deduced from sequences identified from cDNA libraries of human or mouse origin or produced from recombinant expression symptoms.

By "substantially homologous" it is meant that the degree of homology of human and mouse BID polypeptide to a BID polypeptide from any species is greater than that between BID and any previously reported member of the BCL-2 family of proteins.

Sequence identity or percent identity is intended to mean the percentage of same residues between two sequences, referenced to human BID polypeptides when determining percent identity with non-human BID polypeptides and referenced to human BID polypeptides when determining percent identity with non-BID BCL-2 family members, when the two sequences are aligned using the Clustlal method (Higgins et al, *Cabios* 8: 189–191, 1992 which is incorporated by reference) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in *Atlas of Protein Sequence and Structure*, Dayhoff, Ed., NBRF, Washington, Vol. 5, suppl. 3, p. 345, 1978 which is incorporated by reference).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to sequences as indicated above for identity comparisons. Conservative amino acid changes satisfying this requirement are: R-K; E-D, Y-F, L-M; V-I, Q-H.

The degree of homology between the murine BID polypeptide and the human BID polypeptide is 72.3% identity. It is believed that all BID polypeptide orthologs will have at least about 65% identity with the human BID polypeptide.

BID polypeptides can also include derivatives of BID polypeptides which are intended to include hybrid and modified forms of BID including fusion proteins and BID fragments and hybrid and modified forms in which certain amino acids have been deleted or replaced and modifications such as where one or more amino acids have been changed to a modified amino acid or unusual amino acid and modifications such as glycosylations so long as the hybrid or modified form retains the biological activity of BID. By retaining the biological activity, it is meant that cell death is induced by the BID polypeptide, although not necessarily at the same level of potency as that of the naturally-occurring BID polypeptide identified for human or mouse and that can be produced, for example, recombinantly.

Also included within the meaning of substantially homologous is any BID polypeptide which may be isolated by virtue of cross-reactivity with antibodies to the BID polypeptide described herein or whose encoding nucleotide sequences including genomic DNA, mRNA or cDNA may be isolated through hybridization with the complementary sequence of genomic or subgenomic nucleotide sequences or cDNA of the BID polynucleotides herein or fragments thereof. It will also be appreciated by one skilled in the art that degenerate DNA sequences can encode human BID polynucleotide sequences and these are also intended to be included within the present invention as are allelic variants of BID.

Polynucleotides encoding full-length BID or fragments or analogs thereof, may include sequences that facilitate transcription (expression sequences) and translation of the coding sequences, such that the encoded polypeptide product is produced. Construction of such polynucleotide is described further in Maniatis et al. (Maniatis et al., *Molecular Cloning: A Laboratory Manual,* 2nd Ed., 1989, Cold Spring Harbor, N.Y. which is incorporated by reference). For example, but not a limitation, such polynucleotides can include a promoter, a transcription termination site (polyadenylation site in eukaryotic expression hosts), a ribosome binding site, and, optionally, an enhancer for the use in eukaryotic expression hosts, and, optionally, sequences necessary for replication of a vector. A typical eukaryotic expression cassette will include a polynucleotide sequence encoding a BID polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

Preferably, the amino acid sequences of BID polypeptides occur in the given order and may comprise other intervening and/or terminal sequences; generally such polypeptides are less than 1000 amino acids in length, more usually less than about 500 amino acids in length, and frequently approximately 194 amino acids in length. The degeneracy of the genetic code gives a finite set of polynucleotide sequences encoding these amino acid sequences; this set of degenerate sequences may be readily generated by hand or by computer using commercially available software. Isolated BID polynucleotides typically are less than approximately 10,000 nucleotides in length.

Additionally, where expression of a polypeptide is not desired, polynucleotides of this invention need not encode a functional protein. Polynucleotides of this invention may serve as hybridization probes and/or PCR primers for detecting BID RNA or DNA sequences.

BID polynucleotides may be short oligonucleotides such as for example 20–100 bases long, such as for use as hybridization probes and/or PCR primers. BID polynucleotide sequences may also comprise part of a larger polynucleotide, for example, a cloning vector comprising a BID clone and may be fused, by polynucleotide linkage, in frame with another polynucleotide sequence encoding a different protein (for example, glutathione s-transferase or β-galactosidase) for encoding expression of a fusion protein. Typically, BID polynucleotides comprise at least 25 consecutive nucleotides which are substantially identical a naturally-occurring BID sequence, more usually BID polynucleotides comprise an least 50 to 100 consecutive nucleotides which are substantially identical to a naturally-occurring BID sequence. However, it will be recognized that the minimum length of a BID polynucleotide required for specific hybridization to a BID target sequence will depend on several factors: G/C content, positioning of mismatched bases (if any), degree of uniqueness of the sequence as compared to the population of target polynucleotides, and chemical nature of the polynucleotide (for example, methylphosphonate backbone, polyamide nucleic acid, phosphorothiolate and the like) among other factors.

The term "naturally-occurring" as used herein in reference to BID or related BCL-2 family members is intended to mean a polynucleotide or polypeptide that can be found in nature and present in an organism (including viruses) although not necessarily in a discrete or isolated form, which can be isolate from a source in nature and which has not been intentionally modified by man in the laboratory.

BID polynucleotides contain a sequence encoding a BH3 domain polypeptide comprised of the sequence Leu-Ala-Gln-$Xaa_1$-Gly-Asp-$Xaa_2$-Met-Asp, where $Xaa_1$ is Ile or Val and $Xaa_2$ is Gln or Ser (SEQ ID NO: 7). Preferred is a human BID polynucleotide containing a sequence encoding the BH3 domain Leu-Ala-Gln-Val-Gly-Asp-Ser-Met-Asp (SEQ ID NO: 8).

The preferred Bid polynucleotide of the present invention is comprised of the sequence:

ATGGA CTGTGAGGTC AACAACGGTT CCAGCCT-CAG GGATGAGTGC ATCACAAACC TACTGGTGTT TGGCTTCCTC CAAAGCTGTT CTGACAACAG CTTC-CGCAGA GAGCTGGACG CACTGGGCCA CGAGCT-GCCA GTGCTGGCTC CCCAGTGGGA GGGCTACGAT GAGCTGCAGA CTGATGGCAA CCGCAGCAGC CACTCCCGCT TGGGAAGAAT AGAGGCAGAT TCT-GAAAGTC AAGAAGACAT CATCCGGAAT ATTGC-CAGGC ACCTCGCCCA GGTCGGGGAC AGCATG-GACC GTAGCATCCC TCCGGGCCTG GTGAACGGCC TGGCCCTGCA GCTCAGGAAC ACCAGCCGGT CGGAGGAGGA CCGGAACAGG GACCTGGCCA CTGCCCTGGA GCAGCTGCTG CAGGCCTACC CTA-GAGACAT GGAGAAGGAG AAGACCATGC TGGT-GCTGGC CCTGCTGCTG GCCAAGAAGG TGGC-CAGTCA CACGCCGTCC TTGGCTCCGT GATGTCTTTC ACACAACAGT AATTTATTA ACCA-GAACCT ACGCACCTAC GTGAGGAGCT TAGCCA-GAAA TGGGATGGAC TGA (SEQ ID NO: 1).

In addition, the BID polynucleotide can be comprised of one or more sequences selected from the group consisting of:

5'-ATGGACTGTGAGGTCAACAACGGTTCCAGCC-3'; (SEQ ID NO: 9)

5'-TCAGGGATGAGTGCATCACAAACCTACTGGTGT TTGG-3';(SEQ ID NO: 10)

5'-CTTCCTCCAAAGCTGTTCTGACAACAGCTTCCG-3';(SEQ ID NO: 11)

5'-CAGAGAGCTGGACGCACTGGGCCAC-3';(SEQ ID NO: 12)

5'-GAGCTGCCAGTGCTGGCTCCCC-3';(SEQ ID NO: 13)
5'-AGTGGGAGGGCTACGATGAGCTGCAG-3';(SEQ ID NO: 14)
5'-ACTGATGGCAACCGCAGCAGCCACTC-3';(SEQ ID NO: 15)
5'-CCGCTTGGGAAGAATAGAGGCAGATTCTGAAAG-3';(SEQ ID NO: 16)
5'-TCAAGAAGACATCATCCGGAATATTGCCAGGCAC-3';(SEQ ID NO: 17)
5'-CTCGCCCAGGTCGGGGACAGCATGGAC-3';(SEQ ID NO: 18)
5'-CGTAGCATCCCTCCGGGCCTGGTGAAC-3';(SEQ ID NO: 19)
5'-GGCCTGGCCCTGCAGCTCAGGAACAC-3';(SEQ ID NO: 20)
5'-CAGCCGGTCGGAGGAGGACCGGAAC-3';(SEQ ID NO: 21)
5'-AGGGACCTGGCCACTGCCCTGGAG-3';(SEQ ID NO: 22)
5'-CAGCTGCTGCAGGCCTACCCTAGAGAC-3';(SEQ ID NO: 23)
5'-ATGGAGAAGGAGAAGACCATGCTGGTGCTGG-3'; (SEQ ID NO: 24)
5'-CCCTGCTGCTGGCCAAGAAGGTGGC-3';(SEQ ID NO: 25)
5'-CAGTCACACGCCGTCCTTGGCTCCG-3';(SEQ ID NO: 26)
5'-TGATGTCTTTCACACAACAGTAATTTTATTAAC CAGAACCTACGCACC'3';(SEQ ID NO: 27)
5'-TACGTGAGGAGCTTAGCCAGAAATGGGATGGA CTGA-3'(SEQ ID NO: 28)

A preferred BID polynucleotide comprises all of the above sequences in the given order with or without spacer polynucleotides between the given sequences. The above sequences can also be used as hybridization probes suitable for hybridizing with a naturally-occurring BID sequence.

BID polypeptides can also include a sequence of contiguous amino acids comprising one or more BID epitopes. Preferred BID epitopes are:
-MDCEVNNGSSLRDEC-; -ITNLLVFGFLQSCSDNSFR-; (SEQ ID NO: 29)
-RELDALGHELPVLAPQWEGYDELQT-;(SEQ ID NO: 30)
-DGNRSSHSRLGRIEADSESQEDII-;(SEQ ID NO: 31)
-RNIARHLAQVGDSMDRSIPPGLVNGLALQ-;(SEQ ID NO: 32)
-LRNTSRSEEDRNR-;(SEQ ID NO: 33)
-DLATALEQLLQAYPRDMEKEKTMLV-;(SEQ ID NO: 34)
-LALLLAKKVASHTPSLLRDVFHTTVNFI-;(SEQ ID NO: 35) and
-NQNLRTYVRSLARNGMD-(SEQ ID NO: 36).

Genomic clones of BID, particularly of the murine BID gene, may be used to construct homologous targeting constructs for generating cells and transgenic nonhuman animals having at least one functionally disrupted BID allele. Guidance for construction of homologous targeting constructs are known in the art. Homologous targeting can be used to generate "knockout" mice, which are heterozygous or homozygous for an inactivated allele. Such mice may be sold commercially as research animals or they may be used to screen for substances which can functionally replace BID. Such substances are useful in the treatment of neoplasm and in treating autoimmune diseases.

Chimeric target mice are derived according to Hogan et al. (Hogan et al., *Manipulating the Mouse Embryo: A Laboratory Manual*, Cold Spring Harbor Laboratory, 1988 which is incorporated by reference) and Robertson (*Teratocarcinomas and Embryonic Stem Cells: A Practical Approach*, E. J. Robertson, Ed., IRL Press, Washington, D.C., 1987) both of which are incorporated by reference. Embryonic stem cells are manipulated according to procedures known in the art (Id., Zjilstra et al, *Nature* 342: 435, 1989; and Schwartzberg et al, *Science* 246: 799 which are incorporated by reference).

Additionally, a BID CDNA or genomic gene copy may be used to construct transgenes for expressing BID polypeptides at high levels and/or under the transcriptional control of transcription control sequences which do not naturally occur adjacent to the BID gene. For example, a constitutive promoter (e.g., a HSV-tk or pgk promoter) or a cell-lineage specific transcriptional regulatory sequence (e.g., a CD4 or CD8 gene promoter/enhancer) may be operably linked to a BID-encoding polynucleotide sequence to form a transgene (typically in combination with a selectable marker such as a neo gene expression cassette). Such transgenes can be introduced into cells such as hematopoietic stem cells and transgenic cells and transgenic nonhuman animals can be obtained according to conventional methods. Transgenic cells and/or transgenic nonhuman animals may be used to generate models of disease and to screen for agents to treat diseases involving overexpression or inappropriate expression of BID such as for example, immunodeficiency diseases, including AIDS, senescence, neurodegenerative disease, ischemic and reperfusion cell death, infertility, wound-healing, and the like.

In the treatment of diseases involving overexpression or inappropriate expression of BID, it may be desirable to modulate or decrease the amount of BID produced or expressed by a cell. In such a disease condition, treatments to modulate or decrease BID can be used. Such treatments can involve administration of antisense polynucleotides to modulate BID expression or the use of BID antibodies, either polyclonal or monoclonal or the use of a substance that binds and neutralizes BID or mutant forms of BID that counter endogenous BID activity.

Thus, in another aspect of the present invention, isolated and purified BID antisense oligonucleotides are provided along with a method utilized for diminishing the level of expression of BID by a cell comprising administering one or more BID antisense oligonucleotides. By BID antisense oligonucleotides reference is made to oligonucleotides that have a nucleotide sequence that interacts through base pairing with a specific complementary nucleic acid sequence involved in the expression of BID such that the expression of BID is reduced. Preferably, the specific nucleic acid sequence involved in the expression of BID is a genomic DNA molecule or mRNA molecule that encodes BID. This genomic DNA molecule can comprise regulatory regions of the BID gene or the coding sequence for a BID polypeptide. The term complementary to a nucleotide sequence in the context of BID antisense oligonucleotides and methods therefor means sufficiently complementary to such a sequence as to allow hybridization to that sequence in a cell, i.e., under physiological conditions. The BID antisense oligonucleotides preferably comprise a sequence containing from about 8 to about 100 nucleotides and more preferably the BID antisense oligonucleotides comprise from about 15 to about 30 nucleotides. The BID antisense oligonucleotides can also include derivatives which contain a variety of modifications that confer resistance to nucleolytic degradation such as, for example, modified internucleoside linkages modified nucleic acid bases and/or sugars and the like (Uhlmann and Peyman, *Chemical Reviews* 90: 543–584, 1990; Schneider and Banner, *Tetrahedron Lett* 31: 335, 1990; Milligan et al., *J Med Chem* 36: 1923–1937, 1993; Tseng et al., *Cancer Gene Therap* 1: 65–71, 1994; Miller et al., *Parasitology* 10: 92–97, 1994 which are incorporated by reference). Such derivatives include but are not limited to backbone modifications such as phosphotriester, phosphorothioate, methylphosphonate, phosphoramidate, phosphorodithioate and formacetal as well as morpholino, peptide nucleic acid analogue and dithioate repeating units. The BID antisense polynucleotides of the present invention can be used in treating overexpression of BID or inappropriate expression of BID such as in treating immunodeficiency diseases, including AIDS, senescence, neurodegenerative disease, ischemic and reperfusion cell death, infertility, wound-healing, and the like. Such treatment can also include the ex vivo treatment of cells.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or in interstitial fluid in vivo. Soluble antisense polynucleotides present in the external milieu have been shown to gain access to the cytoplasm and inhibit translation of specific mRNA species.

The BID polypeptides and polynucleotides, including antisense polynucleotides, of the present invention are provided in isolated and purified form. By "pure form" or "purified form" or "substantially purified form" it is meant that the object species such as a BID polynucleotide or a BID polypeptide is substantially free of other substances which are not the object species. Generally a substantially pure composition will comprise more than about 80 to 90 percent of all macromolecular species present in the composition. Most preferably, the object species is purified to essential homogeneity such that contaminant species cannot be detected in the composition by conventional detection methods and wherein the composition consists essentially of a single macromolecular species. Solvent species, small molecules (<500 Daltons), and elemental ion species are not considered macromolecular species.

A preferred human BID may be made by expression of the DNA sequences encoding a human BID polypeptide in a suitable transformed host cell. Using methods well known in the art, the DNA encoding BID may be linked to an expression vector, transformed into a host cell and conditions established that are suitable for expression of the BID polypeptide by the transformed cell.

Any suitable expression vector may be employed to produce recombinant human BID polypeptide such as, for example, the mammalian expression vector pCB6 (Brewer, *Meth Cell Biol* 43: 233–245, 1994 which is incorporated by reference) or the *E. coli* pET expression vectors, specifically, pET-30a (Studier et al., *Methods Enzymol* 185: 60–89, 1990 which is incorporated by reference) both of which were used herein. Other suitable expression vectors for expression in mammalian and bacterial cells are known in the art as are expression vectors for use in yeast or insect cells. Baculovirus expression systems can also be employed. BID polypeptides can also be prepared by chemical synthesis, by expression in in vitro translation systems using polynucleotide template or by isolation from biological samples. Chemical synthesis of a peptide can be performed, for example, by the classical Merrifeld method of solid phase peptide synthesis (Merrifeld, *J Am Chem Soc* 85: 2149, 1963 which is incorporated by reference) or the FMOC strategy on a Rapid Automated Multiple Peptide Synthesis system (DuPont Company, Wilmington, Del.) (Caprino and Han, *J Org Chem* 37: 3404, 1972 which is incorporated by reference).

Fragments or analogs of a BID polypeptide can also be made. A fragment of a BID polypeptide is a polypeptide that has an amino-terminal and/or carboxy-terminal deletion, but where the remaining amino acid sequence is identical to the corresponding positions in the sequence of the full-length BID polypeptide. Fragments are at least 10 amino acids long, preferably at least 20 amino acids long and most preferably at least 50 amino acids long or longer up to the length of a full-length naturally-occurring BID polypeptide. The term "analog", "mutein" or "mutant" as used herein refers to polypeptides which are comprised of a segment of at least 10 amino acids that has substantial identity to a portion of the naturally-occurring protein. Typically, analog polypeptides comprise a conservative amino acid substitution (or addition or deletion) with respect to the naturally-occurring sequence. Analogs typically are at least 20 amino acids long, preferably at least 50 amino acids long or longer up to the length of a full-length naturally-occurring BID polypeptide.

Polyclonal or monoclonal antibodies to a BID polypeptide or an epitope thereof can be made for use in treating overexpression or inappropriate expression of a BID polypeptide or for use in immunoassays to detect a BID polypeptide. By epitope reference is made to an antigenic determinant of a polypeptide. An epitope could comprise 3 amino acids in a spacial conformation which is unique to the epitope. Generally an epitope consists of at least 5 such amino acids. Typically epitopes contain hydrophilic amino acids such that the particular region of the polypeptide will be likely to be exposed in an aqueous based milieu. Furthermore, antibodies to a BID polypeptide can also be raised against oligopeptides that include a conserved region such as the BH3 domain identified herein.

Methods for preparation of a BID polypeptide or an epitope thereof include methods known in the art for the preparation of polypeptides such as chemical synthesis, recombinant DNA techniques or isolation from biological samples.

Polyclonal antibodies can be prepared by immunizing rabbits or other animals by injecting antigen followed by subsequent boosts at appropriate intervals. The animals are bled and sera assayed against purified BID polypeptide usually by ELISA or by bioassay based upon the ability to accelerate apoptosis in cells. Monoclonal antibodies can be prepared after the method of Milstein and Kohler by fusing splenocytes from immunized mice with continuously replicating tumor cells such as myeloma or lymphoma cells. (Milstein and Kohler *Nature* 256: 495–497, 1975; Gulfre and Milstein, *Methods in Enzymology: Immunochemical Techniques* 73: 1–46, Langone and Banatis eds., Academic Press, 1981 which are incorporated by reference). The hybridoma cells so formed are then cloned by limiting dilution methods and supernates assayed for antibody production by ELISA, RIA or bioassay.

The unique ability of antibodies to recognize and specifically bind to target polypeptide provides an approach for treating an overexpression or inappropriate expression of the BID polypeptide. Thus, another aspect of the present invention provides for a method for preventing or treating diseases involving over expression of a BID polypeptide by treatment of a patient with specific antibodies to the BID polypeptide.

Specific antibodies, either polyclonal or monoclonal, to the BID polypeptide can be produced by any suitable method known in the art as discussed above. For example, murine or human monoclonal antibodies can be produced by hybridoma technology or, alternatively, the BID polypeptide, or an immunologically active fragment thereof, or an anti-idiotypic antibody, or fragment thereof can be administered to an animal to elicit the production of antibodies capable of recognizing and binding to the BID polypeptide. Such antibodies can be from any class of antibodies including, but not limited to IgG, IgA, IgM, IgD, and IgE or in the case of avian species, IgY and from any subclass of antibodies.

Small molecules can mimic the effect of an anti-BID antibody by binding to a BID polypeptide. Such small molecules can be small polypeptides such as analogues or fragments of part or the full sequence of a BCL-2 family member such as BAX or BCL-2 or BCL-$X_L$ or muteins having BH1 domain mutations in which case the polypeptide itself may produce little or no effect on apoptosis, however, the analogue or fragment or mutein is able to bind to a BID polypeptide produced by a cell and thereby diminish the death agonist activity of BID. BID polypeptides can also have mutations within the BH3 domain such that the BID mutein has little or no effect on apoptosis but can bind to a BCL-2 family member partner and prevent the binding of a BID polypeptide produced by a cell to thereby modulate the death agonist activity of BID within the cell.

Non-peptidal substances possessing the biological properties of BID polypeptides in eliciting an apoptotic state or antagonists BID polypeptides can also be made. The techniques for development of peptide mimetics are well known in the art. (See for example, Navia and Peattie, *Trends Pharm Sci* 14: 189–195, 1993; Olson et al, *J Med Chem* 36: 3039–3049 which are incorporated by reference). Typically this involves identification and characterization of the protein target site as well as the protein ligand using X-ray crystallography and nuclear magnetic resonance technology. The amino acid sequence of the BID polypeptide and the BH3 domain which is required for has been identified. Using this information along with computerized molecular modeling, a pharmacophore hypothesis is developed and compounds are made and tested in an assay system.

The BID polypeptides of the present invention can also be used to detect new polypeptides as well as non-peptide compositions capable of associating or binding to BCL-2 family members to serve as either agonists or antagonists to the binding of BID to the particular family member using a standard radioligand assay system. (For example, see Bylund and Toews, *Am J Physiol* 265: L421–429, 1993 which is incorporated by reference). This can be done by first preparing a radiolabeled form of the BID polypeptide or fragment thereof capable of binding to the family member using either a $^3H$ or $^{125}I$ according to standard methods. For example, the Bolton Hunter Reagent can be used (ICN Chemicals, Radioisotope Division, Irvine, Calif.). The radiolabeled BID ligand binds to the BCL-2 family member (e.g. BAX) immobilized to a substrate such as in a standard ELISA-style plate assay. The amount of bound and/or free radiolabeled ligand is then measured. (For example see Slack et al. *BioTechniques* 7: 1132–1138, 1989; Dower et al, *J Immunol* 142: 4314–4320, 1989 which are incorporated by reference). Alternatively, the BCL-2 family member can be radiolabeled and the BID polypeptide immobilized to a substrate. In a variation to this approach, the binding assay is performed with soluble, non-immobilized BID polypeptide and BCL-2 family member. Competitive inhibition of the binding of the radiolabeled BID ligand to the BCL-2 family member on addition of a test compound can be evaluated by standard methods of analysis. (For example, see Rovati, *Pharmacol Res* 28: 277–299, 1993 which is incorporated by reference).

The present invention also provides methods and kits based upon yeast two-hybrid assay systems for identifying polypeptide sequences which bind to a BID polypeptide (see Chien et al. *PNAS USA* 88: 9578, 1991 which is incorporated by reference). This approach identifies protein-protein interactions in vivo through reconstitution of a transcriptional activator, the yeast GAL4 transcription protein. Polynucleotides encoding two hybrid proteins, one consisting of the yeast GAL4 DNA-binding domain fused to a polypeptide sequence of a known protein and the other consisting of the Bal4 activation domain fused to a polypeptide sequence of a second protein are constructed and introduced into a yeast host cell. Intramolecular binding between the two fusion proteins reconstitutes the Gal4 DNA-binding domain with the Gal4 activation domain, which leads to the transcriptional activation of a reporter gene such as, for example, lacZ, which is operably linked to a Gal4 binding site. Typically, the two-hybrid method is used to identify polypeptide sequence which interact with a known protein. Variations in this assay method can be used to assess the effect of mutations of a known polypeptide, to identify interacting structural domains and to identify interactive proteins forming heterodimers or heteromultimers.

The invention also provides host organisms (typically unicellular organisms, e.g. a yeast cell such as *Saccharomyces cervisiae*) which harbor a BID protein two-hybrid system, typically in the form of polynucleotides encoding a first hybrid protein, a second hybrid protein, and a reporter gene, wherein the polynucleotides are either stably replicated or introduced for transient expression.

Yeast comprising (1) an expression cassette encoding a GAL4 DNA binding domain (or GAL4 activator domain) fused to a binding fragment of BID capable of binding to a BAX, BCL-2 or BCL-$X_L$ polypeptide, (2) an expression cassette encoding a GAL4 DNA activator domain (or a GAL4 binding domain, respectively) fused to a member of a cDNA library or a binding fragment of BAX, BCL-2 or BCL-$X_L$ capable of binding to a BID polypeptide, and (3) a reporter gene (e.g., β-galactosidase) comprising a cis-linked GAL4 transcriptional response element can be used for agent screening. Such yeast are incubated with a test agent and expression of the reporter gene is determined; the capacity of the agent to inhibit expression of the reporter gene as compared to a control culture identifies the agent as a candidate BID modulatory agent. Yeast two-hybrid systems can be used to screen mammalian cDNA expression libraries for cDNA's which encode proteins that bind to BID.

The present invention also provides a kit comprising a two-hybrid system having (1) a first hybrid protein transcript polypeptide and a transcriptional activation domain (2) a second hybrid protein comprising a BAX, BCL-2 or BCL-$x_L$ polypeptide and a DNA-binding domain, a host cell, and an instruction manual. Alternatively, the BID polypeptide may be fused to the DNA-binding domain and the BAX, BCL-2 or BCL-$x_L$ polypeptide fused to the activation domains. Such kits may optionally include a panel of agents for testing for the capacity to alter intermolecular binding between the first and second hybrid proteins.

The present invention also includes therapeutic or pharmaceutical compositions comprising a BID polypeptide, derivative thereof or biologically active fragment thereof in an effective amount for treating diseases or disease conditions in which the cell death signal is down regulated and the affected cell has an inappropriately diminished propensity for cell death, which is referenced herein as being a decreased apoptotic state. Also encompassed within the present invention are methods comprising administering a therapeutically effective amount of a BID polypeptide. These compositions and methods are useful for treating a number of diseases such as, for example, cancer, other lymphoproliferative conditions, arthritis, inflammation, autoimmune diseases and the like may result from a down regulation of cell death regulation. Treatment can also involve administration to affected cells ex vivo.

The therapeutic or pharmaceutical compositions of the present invention can be administered by any suitable route known in the art including for example intravenous, subcutaneous, intramuscular, transdermal, intrathecal or intracerebral or administration to cells in ex vivo treatment protocols. Administration can be either rapid as by injection or over a period of time as by slow infusion or administration of slow release formulation. For treating tissues in the central nervous system, administration can be by injection or infusion into the cerebrospinal fluid (CSF). When it is intended that a BID polypeptide be administered to cells in the central nervous system, administration can be with one or more agents capable of promoting penetration of BID polypeptide across the blood-brain barrier.

BID can also be linked or conjugated with agents that provide desirable pharmaceutical or pharmacodynamic properties. For example, BID can be coupled to any substance known in the art to promote penetration or transport across the blood-brain barrier such as an antibody to the transferrin receptor, and administered by intravenous injection. (See for example, Friden et al., *Science* 259: 373–377, 1993 which is incorporated by reference). Furthermore, BID can be stably linked to a polymer such as polyethylene glycol to obtain desirable properties of solubility, stability, half-life and other pharmaceutically advantageous properties. (See for example Davis et al. *Enzyme Eng* 4: 169–73, 1978; Burnham, *Am J Hosp Pharm* 51: 210–218, 1994 which are incorporated by reference).

Furthermore, the BID polypeptide can be in a composition which aids in delivery into the cytosol of a cell. For example, the peptide may be conjugated with a carrier moiety such as a liposome that is capable of delivering the peptide into the cytosol of a cell. Such methods are well known in the art (for example see Amselem et al., *Chem Phys Lipids* 64: 219–237, 1993 which is incorporated by reference). Alternatively, the BID polypeptide can be modified to include specific transit peptides or fused to such transit peptides which are capable of delivering the BID polypeptide into a cell. In addition, the polypeptide can be delivered directly into a cell by microinjection.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. BID can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used.

It is also contemplated that certain formulations containing the BID polypeptide or fragment thereof are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, a BID polypeptide may be therapeutically administered by implanting into patients vectors or cells capable of producing a biologically-active form of BID or a precursor of BID, i.e. a molecule that can be readily converted to a biological-active form of BID by the body. In one approach cells that secrete BID may be encapsulated into semipermeable membranes for implantation into a patient. The cells can be cells that normally express BID or a precursor thereof or the cells can be transformed to express BID or a biologically active fragment thereof or a precursor thereof. It is preferred that the cell be of human origin and that the BID polypeptide be human BID when the patient is human. However, the formulations and methods herein can be used for veterinary as well as human applications and the term "patient" as used herein is intended to include human and veterinary patients.

In a number of circumstances it would be desirable to determine the levels of a BID polypeptide in a patient. The identification of BID along with the present report showing that BID polypeptide is expressed by a number of tissues provides the basis for the conclusion that the presence of BID serves a normal physiologic function related to modulation of cell death. Endogenously produced BID polypeptides may also play a role in certain disease conditions, where cell death is either up-regulated or down-regulated.

Given that BID is expressed in kidney, brain, spleen, liver, testis and lung, it is likely that the level of BID may be altered in a variety of conditions and that quantification of BID levels would provide clinically useful information. Furthermore, because it has been demonstrated herein that increased levels of BID expressed by a cell can shift the cell death regulatory mechanism of that cell to decrease viability, it is believed that measurement of the level of BID in a cell or cells such as in a group of cells, tissue or neoplasia, like will provide useful information regarding apoptotic state of that cell or cells. In addition, because, BID interacts with related BCL-2 family members, in particular BAX and also BCL-2 and BCL-$X_L$ it can also be desirable to determine the cellular levels of these BID-interacting BCL-2 family members.

Furthermore, in the treatment of disease conditions, compositions containing BID can be administered exogenously and it would likely be desirable to achieve certain target levels of BID polypeptide in sera, in any desired tissue compartment or in the affected tissue. It would, therefore, be advantageous to be able to monitor the levels of BID polypeptide in a patient or in a biological sample including a tissue biopsy sample obtained form a patient and, in some cases, also monitoring the levels of BAX and, in some circumstances, also monitoring levels of BCL-2 and BCL-$X_L$. Accordingly, the present invention also provides methods for detecting the presence of BID in a sample from a patient.

The term "detection" as used herein in the context of detecting the presence of BID in a patient is intended to include the determining of the amount of BID or the ability to express an amount of BID in a patient, the distinguishing of BID from related BCL-2 family members, the estimation of prognosis in terms of probable outcome of a disease involving BID and the prospect for recovery, the monitoring of the BID levels over a period of time as a measure of status of the condition, and the monitoring of BID levels for determining a preferred therapeutic regimen for the patient.

To detect the presence of BID in a patient, a sample is obtained from the patient. The sample can be a tissue biopsy sample or a sample of blood, plasma, serum, CSF or the like. BID is expressed in a wide variety of tissues including kidney, brain, spleen, liver, testis and lung and samples for detecting BID can be taken from any of these tissues as well as from a diseased tissue such as a neoplasia. When assessing peripheral levels of BID polypeptide, the sample can be a sample of a cells obtained from blood or a cell-free sample such as plasma or serum.

In some instances it is desirable to determine whether a BID gene is intact in the patient or in a tissue or cell line within a patient or obtained from a patient and maintained ex vivo. By an intact BID gene it is meant that there are no alterations in the gene such as point mutations, deletions, insertions, chromosomal breakage, chromosomal rearrangements and the like wherein such alteration might alter production of BID or alter its biological activity, stability or the like to lead to disease processes or susceptibility to repression of cell death. Thus, in one embodiment of the present invention a method is provided for detecting and characterizing any alterations in a BID gene. The method comprises providing an oligonucleotide that contains BID cDNA, genomic DNA or a fragment thereof or a derivative thereof. By a derivative of an oligonucleotide, it is meant that the derived oligonucleotide is substantially the same as the sequence from which it is derived in that the derived sequence has sufficient sequence complementarily to the sequence from which it is derived to hybridize to the BID gene. The derived nucleotide sequence is not necessarily physically derived from the nucleotide sequence, but may be generated in any manner including for example, chemical synthesis or DNA replication or reverse transcription or transcription.

Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact BID gene or a BID gene abnormality.

Hybridization to the BID gene would involve denaturing the chromosomal DNA to obtain a single-stranded DNA; contacting the single-stranded DNA with a gene probe associated with the BID gene sequence; and identifying the hybridized DNA-probe to detect chromosomal DNA containing at least a portion of the human BID gene.

The term "probe" as used herein refers to a structure comprised of a polynucleotide which forms a hybrid structure with a target sequence, due to complementarity of probe sequence with a sequence in the target region. Oligomers suitable for use as probes may contain a minimum of about 8–12 contiguous nucleotides which are complementary to the targeted sequence and preferably a minimum of about 20.

The BID gene probes of the present invention can be DNA or RNA oligonucleotides and can be made by any method known in the art such as, for example, excision, transcription or chemical synthesis. Probes may be labelled with any detectable label known in the art such as, for example, radioactive or fluorescent labels or enzymatic marker. Labeling of the probe can be accomplished by any method known in the art such as by PCR, random priming, end labelling, nick translation or the like. One skilled in the art will also recognize that other methods not employing a labelled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25–45° C., more preferably at 32–40° C. and more preferably at 37–38° C. The time required for hybridization is from about 0.25 to about 96 hours, more preferably from about one to about 72 hours, and most preferably from about 4 to about 24 hours.

BID gene abnormalities can also be detected by using the PCR method and primers that flank or lie within the BID gene. The PCR method is well known in the art. Briefly, this method is performed using two oligonucleotide primers which are capable of hybridizing to the nucleic acid sequences flanking a target sequence that lies within a BID gene and amplifying the target sequence. The terms "oligonucleotide primer" as used herein refers to a short strand of DNA or RNA ranging in length from about 8 to about 30 bases. The upstream and downstream primers are typically from about 20 to about 30 base pairs in length and hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, the method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize with the strand being amplified.

After PCR amplification, the DNA sequence comprising BID polynucleotide or a fragment thereof is then directly sequenced and analyzed by comparison of the sequence with the sequences disclosed herein to identify alterations which might change activity or expression levels or the like.

In another embodiment a method for detecting BID is provided based upon an analysis of tissues expressing the BID gene such as those tissues identified below in example 2 as expressing the BID gene. The method comprises hybridizing a polynucleotide to mRNA from a sample of tissues that normally express the BID gene. The sample is obtained from a patient suspected of having an abnormality in the BID gene or in the BID gene of particular cells.

To detect the presence of mRNA encoding BID polypeptide, a sample is obtained from a patient. The sample can be from blood or from a tissue biopsy sample. The sample may be treated to extract the nucleic acids contained therein. The resulting nucleic acid from the sample is subjected to gel electrophoresis or other size separation techniques.

The mRNA of the sample is contacted with a DNA sequence serving as a probe to form hybrid duplexes. The use of a labeled probes as discussed above allows detection of the resulting duplex.

When using the cDNA encoding BID polypeptide or a derivative of the cDNA as a probe, high stringency conditions can be used in order to prevent false positives, that is the hybridization and apparent detection of BID nucleotide sequences when in fact an intact and functioning BID gene is not present. When using sequences derived from the BID cDNA, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al. (Sambrook, et al. 1989, supra).

In order to increase the sensitivity of the detection in a sample of mRNA encoding the BID polypeptide, the technique of reverse transcription/polymerase chain reaction (RT/PCR) can be used to amplify cDNA transcribed from mRNA encoding the BID polypeptide. The method of RT/PCR is well known in the art.

The RT/PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and BID specific primers. (Belyavsky et al, *Nucl Acid Res* 17: 2919–2932, 1989; Krug and Berger, *Methods in Enzymology,* Academic Press, N.Y., Vol.152, pp. 316–325, 1987 which are incorporated by reference).

The polymerase chain reaction method is performed as described above using two oligonucleotide primers that are substantially complementary to the two flanking regions of the DNA segment to be amplified.

Following amplification, the PCR product is then electrophoresed and detected by ethidium bromide staining or by phosphoimaging.

The present invention further provides for methods to detect the presence of the BID polypeptide in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (for example see *Basic and Clinical Immunology,* Sites and Terr, eds., Appleton & Lange, Norwalk, Conn. pp 217–262, 1991 which is incorporated by reference). Preferred are binder-ligand immunoassay methods including reacting antibodies with an epitope or epitopes of the BID polypeptide and competitively displacing a labeled BID polypeptide or derivative thereof.

As used herein, a derivative of the BID polypeptide is intended to include a polypeptide in which certain amino acids have been deleted or replaced or changed to modified or unusual amino acids wherein the BID polypeptide derivative is biologically equivalent to a BID polypeptide and wherein the polypeptide derivative cross-reacts with antibodies raised against the BID polypeptide. By cross-reaction it is meant that an antibody reacts with an antigen other than the one that induced its formation.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like. Polyclonal or monoclonal antibodies to a BID polypeptide or an epitope thereof can be made for use in immunoassays by any of a number of methods known in the art.

The unique ability of antibodies to recognize and specifically bind to target proteins provides an approach for treating an overexpression of a BID polypeptide. Thus, another aspect of the present invention provides for a method for preventing or treating diseases involving overexpression of a BID polypeptide by treatment of a patient with specific antibodies to the BID polypeptide. The antibodies can be either polyclonal or monoclonal and can be from any class or subclass of antibodies.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the isolation and identification of murine and human BID cDNA.

BID was isolated by protein interactive cloning from a cDNA expression library of a murine T cell hybridoma line, 2B4. First strand DNA synthesis was primed with oligo(dT) and completed using SuperScript Choice system (Bibco BRL). Size-fractionated CDNA ($^3$ 500 bp) was directionally cloned into λEXlox vector (Novagen), which allowed the expression of cloned cDNA in frame with the T7-gene-10 product under the T7 promoter. Novagen's PhageMaker system was used for packaging and the CDNA library underwent one round of amplification.

Screening was performed as described previously (Blanar and Rutter, Science 256: 1014–1018, 1992 which is incorporated by reference). Murine bcl-2 and bax cDNA's deleted of the COOH-terminal signal-anchor segment were used to generate GST-HMK-BCL-2 or GST-HMK-mBAX fusion protein. The bcl-2 and bax cDNA's, deleted of the COOH-terminal 22 or 19 amino acids, respectively, were amplified by PCR and inserted into the EcoRI site of a modified pGEX-3X vector (pGEX-HMK) to generate pGEX-HMK-BCL-2 or -BAX. The purified fusion proteins were labeled in vitro by phosphorylation of the heart muscle kinase (HMK) epitope with bovine HMK (Sigma) and [γ-$^{32}$P]ATP. Labeled proteins were used to screen the λEXlox expression library constructed from the 2B4 murine T cell hybridoma line.

A total of 1×10$^6$ plaques were plated. Plaques were transferred overnight to IPTG-immersed nitrocellulose filters. Filters were subsequently blocked and incubated with the probes overnight. After washing filters were subjected to autoradiography.

The same, novel gene was identified multiple times with both BCL-2 and BAX probes. Positive clones were further purified. loxP-cre recombination was used to excise the plasmid. Sequencing was performed by standard procedures.

A full length cDNA having 588 nucleotides (SEQ ID NO: 6) was obtained which encodes the murine BID 195 amino acid polypeptide (SEQ ID NO: 3). The molecular weight of the murine BID polypeptide was predicted to be 21.95 kDa.

Two human clones containing homology to Bid sequences were identified upon searching the EST division of the GenBank with our newly determined murine Bid cDNA sequence. The EST sequences of the two clones contained partial overlapping sequences of a presumed human homolog to the murine Bid. One of these clones (Clone Id No: 52055) was obtained from infant brain and the other (Clone Id No: 128065) was obtained from fetal liver spleen. The 5' EST sequence of the 52055 clone contained the partial sequence corresponding to nucleotides 1–345 of human bid cDNA (FIG. 1A, SEQ ID NO: 1) and the 5' EST sequence of the 128065 clone contained the partial sequence corresponding to nucleotides 289–603 of the variant human bid cDNA (FIG. 1B, SEQ ID NO: 2). We obtained and completely sequenced the 52055 clone which contains a 1.1 kb insert. The human bid sequence was identified by virtue of its homology to the murine BID (FIG. 1A and (SEQ ID NO: 1) and FIG. 1B (SEQ ID NO: 3). The full-length sequence of the variant human bid cDNA was deduced from the complete sequence of the 52055 clone and the reported EST of the 128065 clone containing an additional 15 nucleotide sequence near the 3' end (FIG. 1B(SEQ ID NO: 2)).

A BLAST search identified a region within this gene that shares high sequence homology with the well-conserved BH3 domain of the BCL-2 family. However, BID does not display sequence conservation with other regions of the BCL-2 family including the BH1, BH2 or BH4 domains. Moreover, BID does not possess a COOH-terminal hydrophobic region typical of most BCL-2 family members which serves as a signal-anchor segment for these membrane proteins.

EXAMPLE 2

This example illustrates the distribution of expression of BID mRNA in adult mouse using Northern blot analysis.

Northern blot analysis was carried out using radiolabeled murine Bid cDNA containing the open reading frame as a probe, hybridized against a poly (A)$^+$RNA blot of adult mouse tissues (Clontech) and washed by standard protocol.

As shown in FIG. 3, BID is expressed in a number of tissues and most abundantly expressed in kidney, and also present in brain, spleen, liver, testis and lung. Little to no BID was found to be present in heart and skeletal muscle.

EXAMPLE 3

This example illustrates the intracellular distribution of BID in the cytosol and membrane fractions of FL5.12-Bcl-2 cells using polyclonal anti-BID antibody.

Purified GST-BID fusion protein was used to immunize rabbits and generate a polyclonal anti-BID antibody. The anti-BID antibody was purified with protein A and delipidized and this antibody was used in this and subsequent examples for Western blotting (1:2000) and immunoprecipitations unless otherwise indicated. Anti-BID antibodies were also prepared using epitopes identified in FIG. 2A. Anti-human-BCL-2 monoclonal antibody 6C8 and biotinylated anti-murine-BAX polyclonal antibody 651 were used for Western blotting analysis (1:2000 and 1:500, respectively). Horseradish peroxidase-conjugated secondary antibodies (CALTAG) or streptavidin (ZYMED) were used at 1:2000 and 1:4000, respectively.

FL5.12-Bcl-2 cells were maintained in Iscove's modified Dulbecco's medium supplemented with 10% fetal calf serum (Gibco BRL), penicillin (100 U/ml), streptomycin (100 μg/ml) and 10% WEHI-3B-conditioned medium as a source of IL-3.

To determine the intracellular distribution of BID, 10$^7$ FL5.12-Bcl-2 cells were collected by centrifugation, washed twice with PBS, and resuspended in hypotonic Buffer A (10 mM Tris [pH 7.5], 25 mM NaF, 5 mM MgCl$_2$, 1 mM EGTA, 1 mM DTT, 0.15 U/ml aprotinin, 20 mM leupeptin, and 1 mM PMSF). After incubation on ice for 15 min, cells were homogenized in a Dounce homogenizer for 50 strokes. Cells were checked under microscope to monitor the degree of lysis. Nuclei and non-lysed cells were removed by centrifugation at 500×g for 10 min. The supernatant was transferred and centrifuged at 315,000×g for 30 min to separate cytosolic and membrane fractions.

Equal amounts of protein from each fraction were size-fractionated by SDS-PAGE followed by Western blotting developed with anti-BID polyclonal antibodies or anti-human-BCL-2 monoclonal antibody 6C8. For Western blotting, cell lysates were separated on 12.5 or 16% Tris-Glycine gels (NOVEX) and transferred to PVDF membranes (BioTrace, Gelman Sciences). Filters were blocked overnight at 4° C. with Tris-buffered saline plus 0.1% Tween 20 (TBST) containing 6% non-fat milk and incubated with antibodies for 1 hr, followed by washing three times in TBST for 5 min, and developed by ECL (Amersham).

Figure 4:
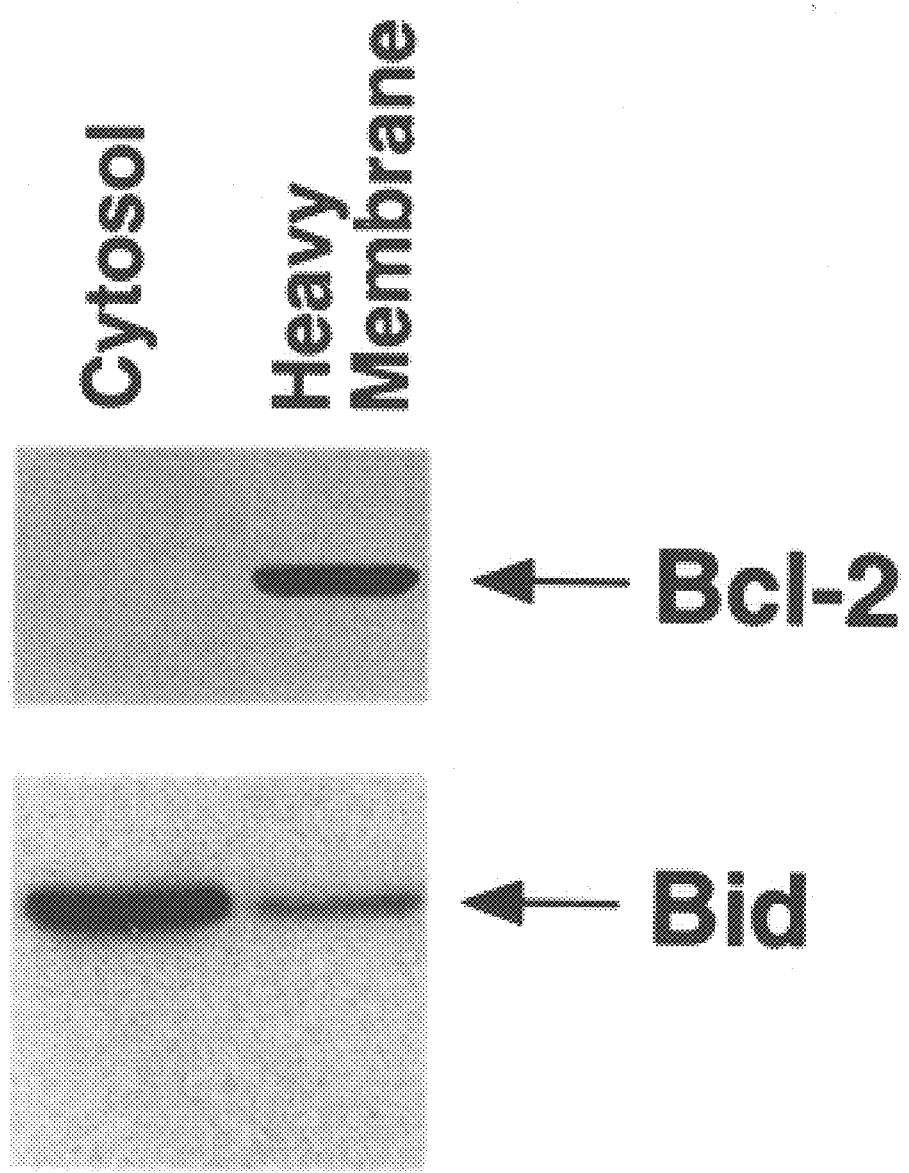
FIG. 4 illustrates the distribution of BID and BCL-2 proteins in the cytosol and membrane fractions of FL5.12-Bcl-2 cells using Western blot analysis.

The anti-BID antibody recognized a 23 kD protein on Western blot analysis of lysates from 2B4 cells and from a mouse hematopoietic cell line, FL5.12 (FIG. 4). Antibodies generated against two BID polypeptides (FIG. 2, Peptides 1 and 2) recognize the same protein on Western blots. Subcellular fractionation revealed that BID was predominantly localized to the cytosol (>90%) with a small fraction being found in the membrane fraction (FIG. 4). This observation is consistent with the lack of a COOH-terminal hydrophobic segment in the BID polypeptide which would suggest that BID does not become anchored in the mitochondria. By way of comparison, BCL-2, as expected was found to exclusively reside in the membrane fraction in Western blot using anti-human-BCL-2 monoclonal Ab 6C8 (1:2000).

EXAMPLE 4

This example illustrates the cell death agonist activity of BID and the counter effect of BID on protection by BCL-2 in transformed hematopoietic cells expressing BID.

A mammalian expression plasmid, pSFFV-Bid was constructed by placing Bid under the control of the Splenic Focus-Forming Virus (SFFV) long terminal repeat. Stable clones expressing BID were established following transfection of pSFFV-Bid into the interleukin (IL-3) dependent early hematopoietic cell line, FL5.12 (Nunez et al., *J Immunol* 144: 3602–3610, 1990 which is incorporated by reference). Stable transfection was accomplished by suspending $10^7$ FL5.12 cells in 1 ml of RPMI 1640 with 10 mM HEPES (pH 7.4). 10–20 $\mu$g of linearized pSFFV construct was added. After 5 min on ice, cells were electroporated at 200 V, 900 $\mu$F for 5 sec (Transfector 300, BTX). After 10 min on ice cells were transferred to 6–7 ml of non-selective medium in a 25 cm$^2$ flask. Two days later cells were put under selection in 96-well plates with 2 $\mu$g/ml G418 Sulfate (Gibco BRL), or 2 $\mu$g/ml Hygromycin B (CalBiochem).

IL-3 deprivation assays were performed as described (Oltvai et al., *Cell* 74: 609–619, 1993 which is incorporated by reference). Briefly, cells cultured at 1–2×10$^6$ cells/ml were collected by centrifugation, washed two times with serum-free medium and once with IL-3-free medium. Cells were resuspended at 10$^6$ cells/ml in IL-3-free medium and 200 $\mu$l aliquots were seeded in 96-well plates. At each time point, 25 $\mu$l sample was taken from 2 separate wells and mixed with an equal volume of 0.08% trypan blue. Cell viability was determined by trypan blue exclusion calculated as the percentage of unstained cells counted under a microscope.

Figure 5A:
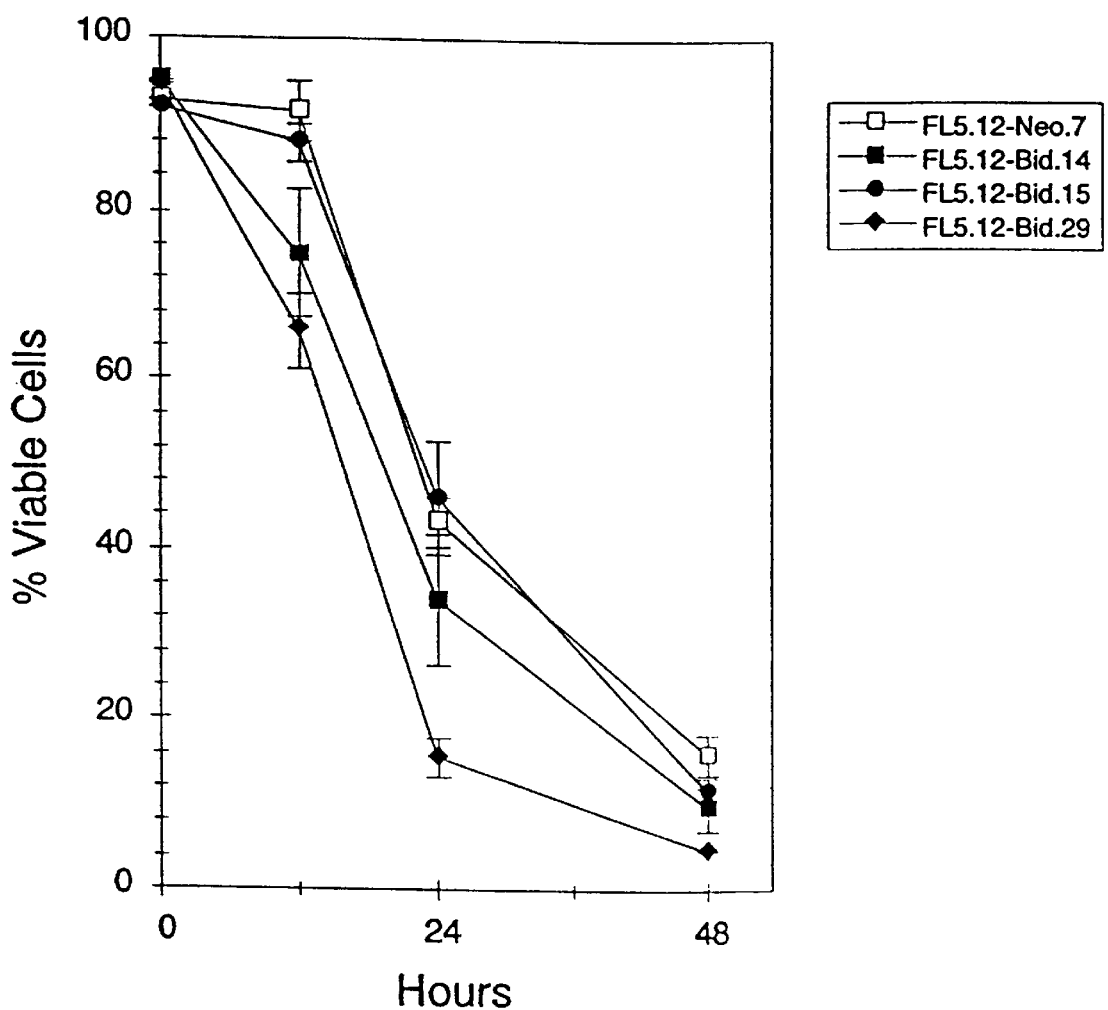
FIGS. 5A–B illustrate the (A) decreased viability in bid clones following IL-3 withdrawal and in a Neo control measured by trypan blue exclusion and (FIG. 5B) the levels of BID in the same cells measured by Western blot analysis (Lane 1: FL5.12-Neo; Lane 2: FL5.12-Bid-14; Lane 3: FL5.12-Bid-15; Lane 4: FL5.12-Bid-29)
Figure 5B:
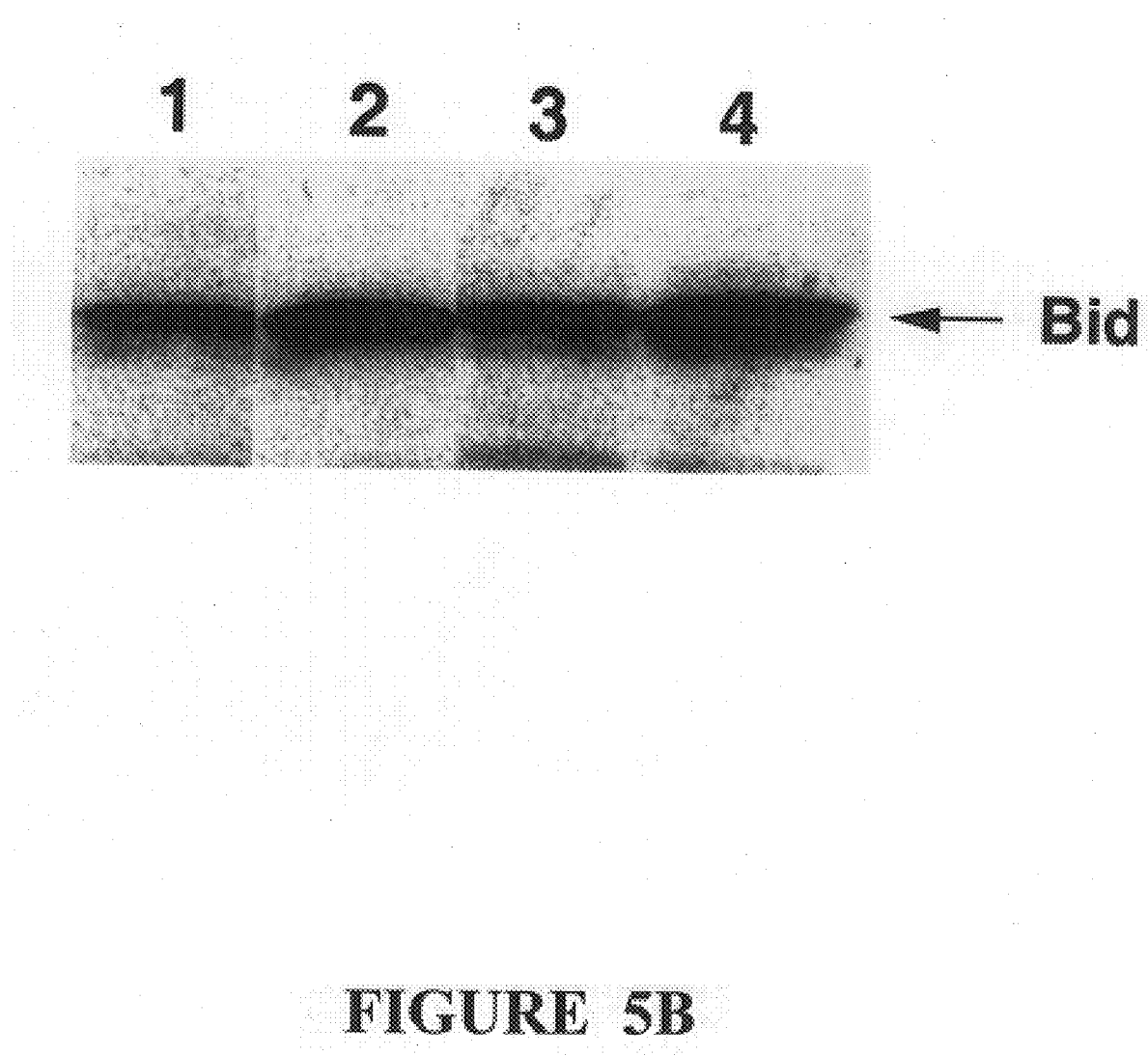

FIG. 5A which shows the mean ± standard deviation of duplicate samples reveals a consistent, but subtle increase in apoptosis was observed in the two highest BID expressing clones following IL-3 withdrawal (FIG. 5A). Lysates of the various FL5.12 clones were separated by 12.5% SDS-PAGE followed by a Western blot developed with an anti-BID Ab. The degree of cell death in individual BID clones corresponded to BID protein levels as detected by Western blot analysis as shown in FIG. 5B, lanes 2–4.

Figure 6A:
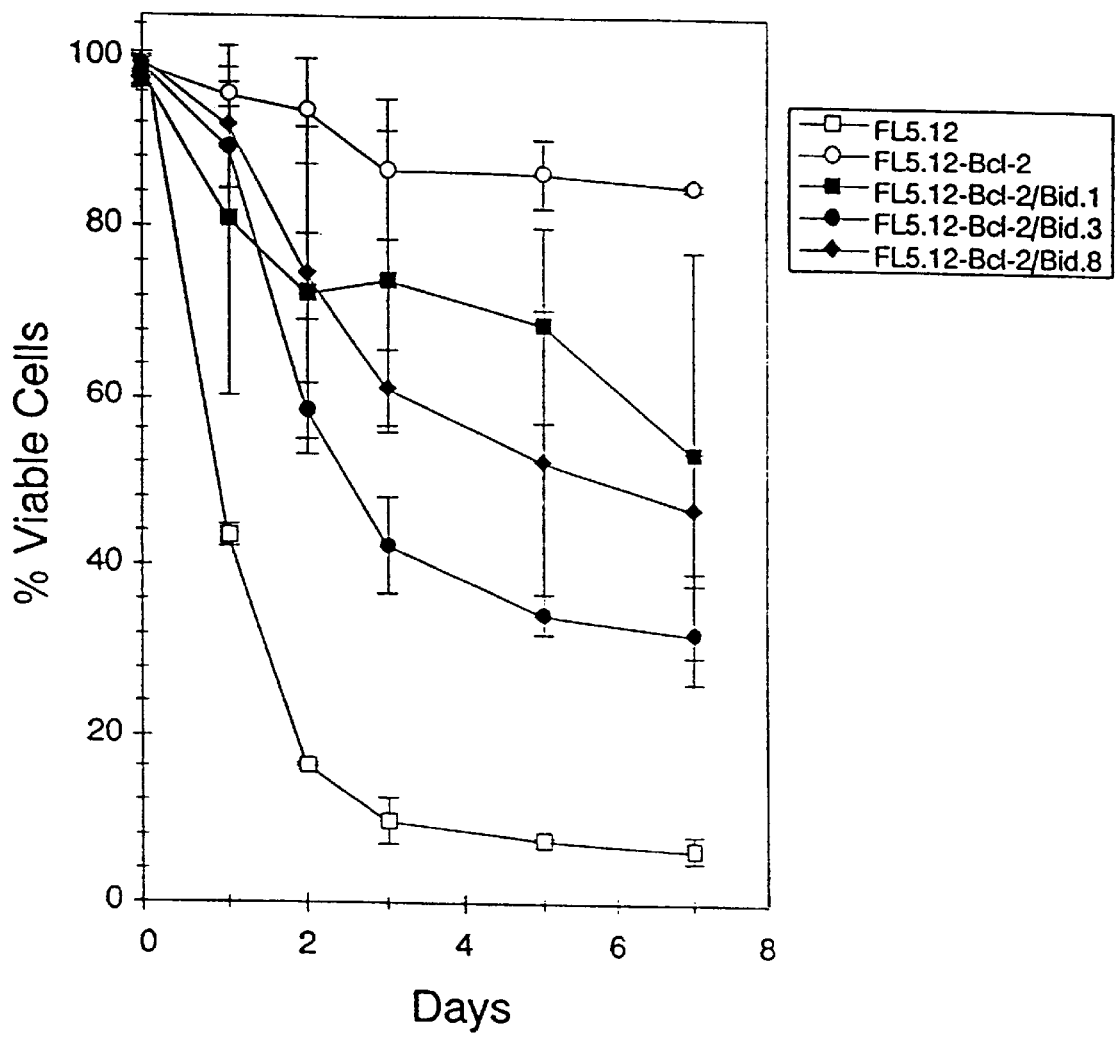
FIGS. 6A–C illustrates the decreased viability in bcl-2/bid clones following IL-3 withdrawal and a FL5.12 control measured by trypan blue exclusion, (FIG. 6B) the levels of BID and (FIG. 6C) the levels of BCL-2 in the same cells measured by Western blot analysis (Lane 1: FL5.12; Lane 2: FL5.12-Bcl-2; Lane 3: FL5.12-Bcl-2/Bid-1; Lane 4: FL5.12-Bcl-2/Bid-3; Lane 5: FL5.12-Bcl-2/Bid-8)
Figure 6B:
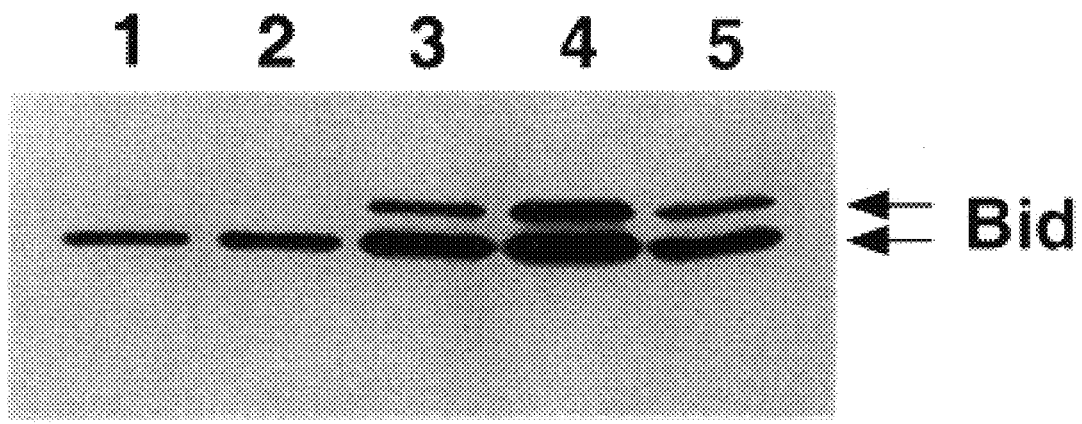

Parental FL5.12 cells are very susceptible to apoptosis as they possess abundant BAX, but little BCL-2 or BCL-X$_L$. To determine whether BID could counteract the anti-apoptotic effect of BCL-2, we introduced BID into FL5.12-Bcl-2 clones. The method described above was used except that 1 $\mu$g of pGK-Hygro was added with the pSFFV construct. BID restored apoptosis to BCL-2 overexpressing clones with intermediate death rates between parental FL5.12 and FL5.12-Bcl-2 cells (FIG. 6A). Western blot analysis was developed with anti-BID antibody as described in example 3. The extent of cell death following IL-3 deprivation correlated with levels of BID protein as assessed by Western blot (FIG. 6B). When highly expressed, BID often ran as a doublet on Western blots, suggesting a post-translational modification (FIG. 6B).

EXAMPLE 5

This example demonstrates that BID can induce apoptosis in Jurkat T cells in the absence of additional death stimulus and that the cell death triggered by BID is inhibited by zVAD.

Expression of BID within FL5.12 indicated that BID could enhance apoptosis after administration of a death signal, IL-3 deprivation. To assess whether BID could induce apoptosis in the absence of an additional death stimulus we established two more assays: a Doxycycline inducible expression system in Jurkat T cells and a transient transfection assay in Rat-1 fibroblasts.

Inducible Jt-Bid clones were generated by introducing the Bid cDNA under the control of the heptamerized tet-operator into a Jurkat clone stably expressing the reverse tetracycline-controlled transactivator (rtTA). Jurkat cells were transfected with pUHD172-lneo which encodes the rtTA transactivator consisting of a fusion between TetR$^r$ and VP16 (Gossen et al., *Science* 268: 1766–1769, 1995 which is incorporated by reference) under the control of a CMV promoter/enhancer. Stable transfectants were screened by transient transfection of pUHC13-3, which encodes a luciferase reporter gene driven by a CMV minimal promoter with heptamerized tet-operators, followed by quantitation of luciferase activity after induction with Doxycycline. The clone with the highest degree of induction, Jt1, was selected and used in later studies. cDNAs encoding wild-type or mutant BID proteins were put under the control of heptamerized tet-operators by cloning into pUHD10-3, co-transfected into Jt1 cells with pGK-Hygro, and selected under 2 $\mu$g/ml Hygromycin B. Hygro resistant clones were screened for BID expression by Western blot of cell lysates before and after Dox induction. Two or more inducible clones were obtained and kept for each mutant and wild-type Bid. Electroporations were performed at 250 V, 960 $\mu$F with Electro Cell Manipulator 600 (BTX).

For viability assays, 1 $\mu$g/ml of Doxycycline (Sigma) was add to 2 ml cultures of each clone. At each time point, cells were collected from 0.3 ml of cell culture, resuspended in 1:4000 solution of annexin V/FITC (Bender MedSystems) and 1 $\mu$g/ml propidium iodide (PI). Flow cytometry was performed (FACScan, Becton Dickinson) and cell populations negative for both annexin V and PI were scored as viable.

Figure 7A:
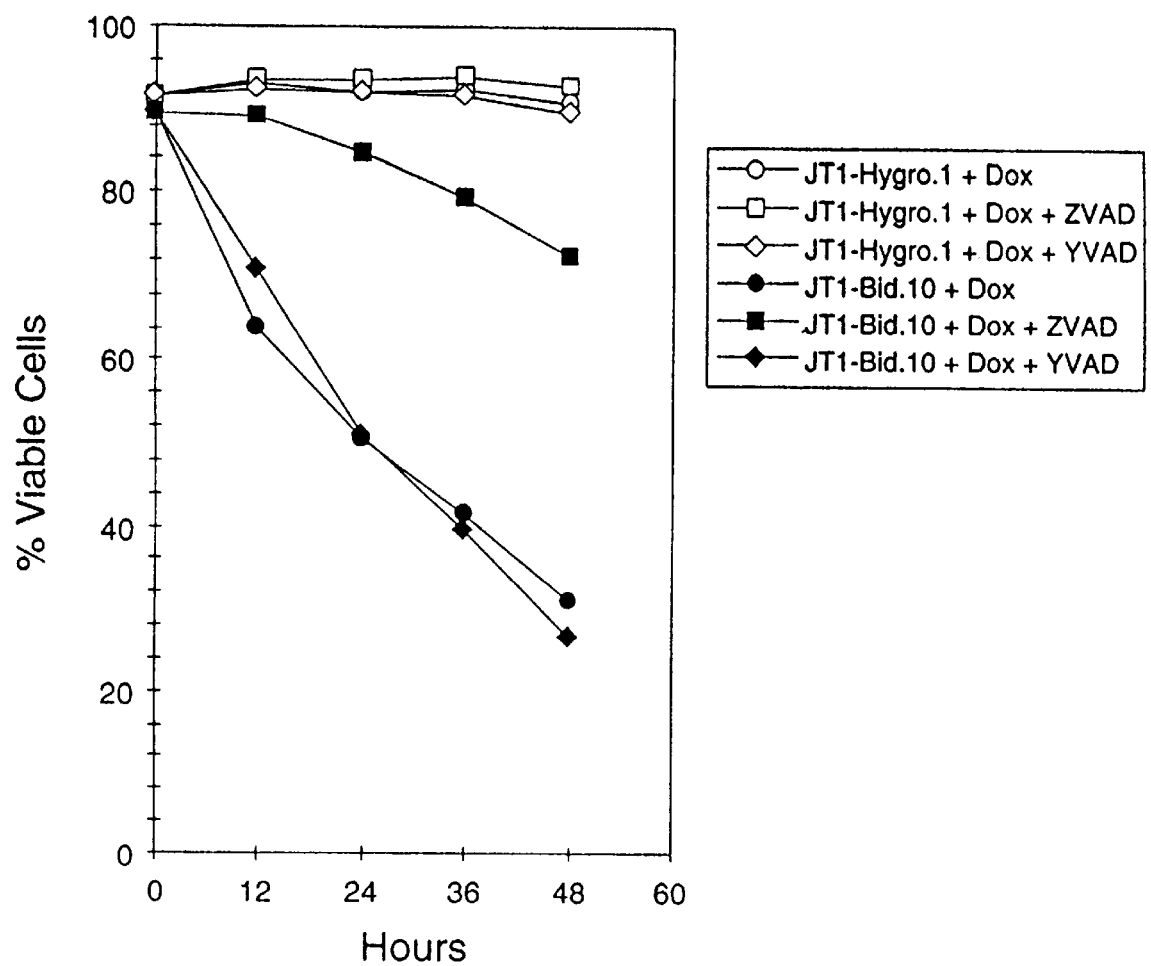
FIGS. 7A–C illustrate (FIG. 7A) the decrease in viability in Jurkat cells expressing BID and the blocking of the apoptotic effect by zVAD, (FIG. 7B) the levels of BID protein after incubation with doxycycline measured by Western blot of cell lysates and (FIG. 6C) viability measured in luciferase activity in Rat-1 fibroblasts co-transfected with bid and luciferase reporter gene and the concentration-dependent blocking of the apoptotic effect by zVAD.
Figure 7B:
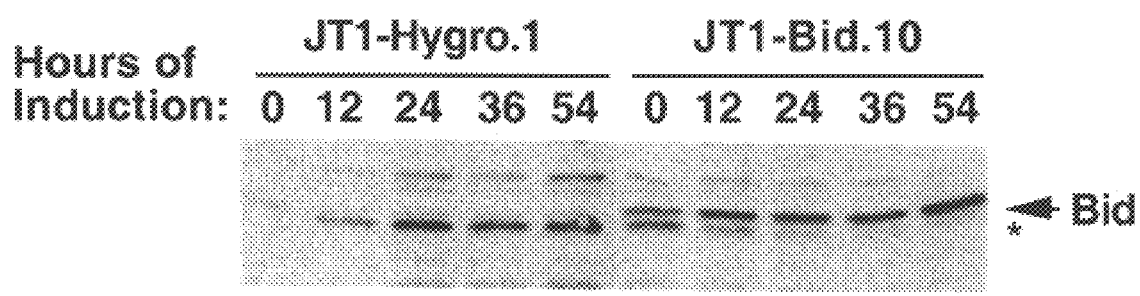

Upon addition of Doxycycline hydrochloride (Dox) Jt-Bid clones rapidly initiated apoptosis, within 12 hrs, and had less than 40% viability at 48 hrs (FIG. 7A). Western blot analysis revealed expression of BID by 12 hrs which maximized by approximately 24 hrs after Dox treatment (FIG. 7B).

We next wished to determine whether ICE-like cysteine proteases are required for BID induced apoptosis. A small peptide based molecule, benzoxy-carbonyl-Val-Ala-Asp-fluoromethylketone (zVAD-fmk), is an irreversible inhibitor particularly effective against the CPP32-like subset of cysteine proteases (Fearnhead et al., *FEBS Lett* 375: 283–288, 1995; Armstrong et al., *J Biol Chem* 271: 16850–16855, 1996; Jacobson et al., *J Cell Biol* 133: 1041–1051, 1996 which are incorporated by reference). Treatment of Jt-Bid cells with 50 $\mu$M zVAD-fmk inhibited BID induced apoptosis (FIG. 7A). In contrast, treatment of Jt-Bid cells with 35 $\mu$M YVAD-cmk, an ICE inhibitor (Thornberry et al., *Nature*

356: 768–774, 1992; Lazebnik et al., *Nature* 371: 346–347, 1994 which are incorporated by reference), had no effect. This result suggests that CPP32-like cysteine protease(s) are required in the cell death pathway triggered by BID.

A transient transfection system was developed in Rat-1 fibroblasts. Preliminary studies established that expression of a luciferase reporter was eliminated in cells undergoing apoptosis (not shown). Subsequently, apoptotic regulatory genes under the control of a CMV promoter were co-transfected with the luciferase reporter and luciferase activity assays were performed 18–20 hrs later.

All cDNA constructs were cloned into pcDNA3 (Invitrogen) under the CMV immediate early promoter. Rat-1a cells were allowed to grow to about 80% confluence in 12-well plates before transfection. The reporter luciferase plasmid (0.1 µg) was mixed with 0.05 µg of various constructs as indicated and 3 µl of LipofectAMINE™ (Gibco BRL) in a volume of 0.5 ml per transfection for 5 hrs. Cells were lysed 18–20 hrs later and a luciferase assay was carried out using luciferase substrates provided by Promega. Luciferase activity was detected by a luminometer (Optocomp II, MGM Instruments Inc.).

Cell viability was estimated as the relative luciferase activity of construct infection of a test construct compared with the control in which the luciferase reporter was co-transfected with an empty pcDNA3 plasmid.

Figure 7C:
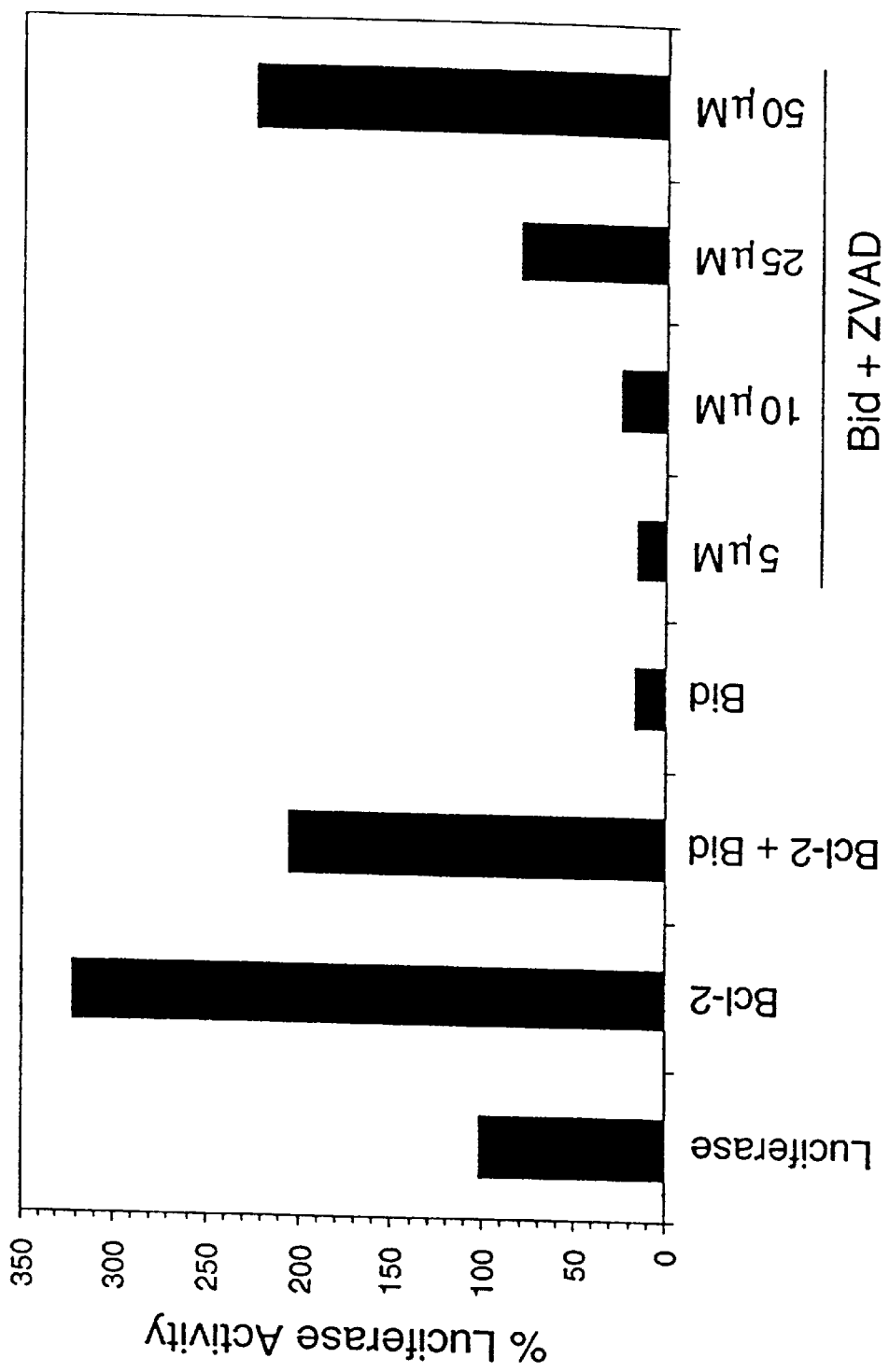

Co-transfection of Bid with the luciferase reporter resulted in a 5-fold decrease in luciferase activity (FIG. 7C). BCL-2 resulted in a 3-fold increase, protecting cells from transfection induced cell death. Simultaneous transfection of BID and BCL-2 showed an intermediate luciferase activity confirming the capacity of BID and BCL-2 to counter each other. Similar to what was observed in the Jurkat inducible system, the induction of apoptosis by BID was also repressed by zVAD-fmk, in a dose-dependent fashion (FIG. 7C).

EXAMPLE 6

This example the heterodimerization of BID with the death agonist, BAX, and the death antagonists, BCL-2 and BCL-$X_L$.

To further characterize the interactions of BID with BCL-2 family members in vivo, a vaccinia virus mediated transient transfection assay was utilized. Bid was cloned into the EXlox vector (Novagen) driven by a T7 promoter with T7-gene-10 in frame at its 5' end. The EXlox-Bid plasmid which encodes a T7-gene-10-BID fusion protein was generated through loxP-cre mediated recombination. The EXlox-Bid plasmid was then co-transfected by lipofection along with BCL-$X_L$ or BCL-2 expression plasmids under the control of the T7 promoter into NIH 3T3 cells infected with a recombinant vaccinia virus encoding T7 polymerase and labeled with [$^{35}$S]Met. Details of the method are as follows.

NIH 3T3 cells were seeded in 6-well plates with 2 ml of medium at $2\times10^5$ cells/well 18 hrs before transfection. Cells were washed with serum free medium, and incubated with 1 ml of fresh medium mixed with 2–5 pfu/well vaccinia virus at 37° C. for 30 min. For each transfection, a total of 5 µg DNA construct either in pBlueScript or pGEM4Z under the T7 promoter and 15 µl of LipofectACgr™ (Gibco BRL) were each added to 100 µl of serum-free medium. DNA and LipofectACgr™ were combined, mixed gently and incubated at room temperature for 10–15 min. The cells were washed, and 0.8 ml serum-free medium plus pre-incubated DNA-LipofectACE™ complexes were added for each transfection. [$^{35}$S]methionine/[$^{35}$S]cysteine (Tran$^{35}$S-label, ICN) was added into each well to a final concentration of 20 µCi/ml. 8–10 hrs later, cells were collected and lysed for immunoprecipitation.

Immunoprecipitations of cell lysates using an anti-T7 epitope mAb (Novagen) were assessed by SDS-PAGE. $5–10\times10^6$ cells were used in each sample for immunoprecipitation. Cells were lysed in 100 µl of NP-40 isotonic lysis buffer with freshly added protease inhibitors (142.5 mM KCl, 5 mM MgCl$_2$, 10 mM HEPES [pH 7.2], 1 mM EDTA, 0.25% NP-40, 0.2 mM PMSF, 0.1% aprotinin, 1 µg/ml pepstatin, and 1 µg/ml leupeptin), incubated on ice for 30 min, and centrifuged at 15,000×g for 10 min to precipitate nuclei and non-lysed cells. 20 µg of anti-BID Ab was added to the supernatant of each sample, mixed, and incubated on ice for 30 min. Subsequently 400 µl of NP-40 buffer was added sample along with 25 µl of protein A-sepharose and incubated at 4° C. with nutation for 1–2 hrs. Immunoprecipitates were collected by a brief spin, washed three times with 1 ml of NP-40 buffer, and solubilized with 1× SDS-PAGE sample buffer. Western blotting was performed on immunoprecipitates as described for direct cell lysates in example 3.

Figure 8A:
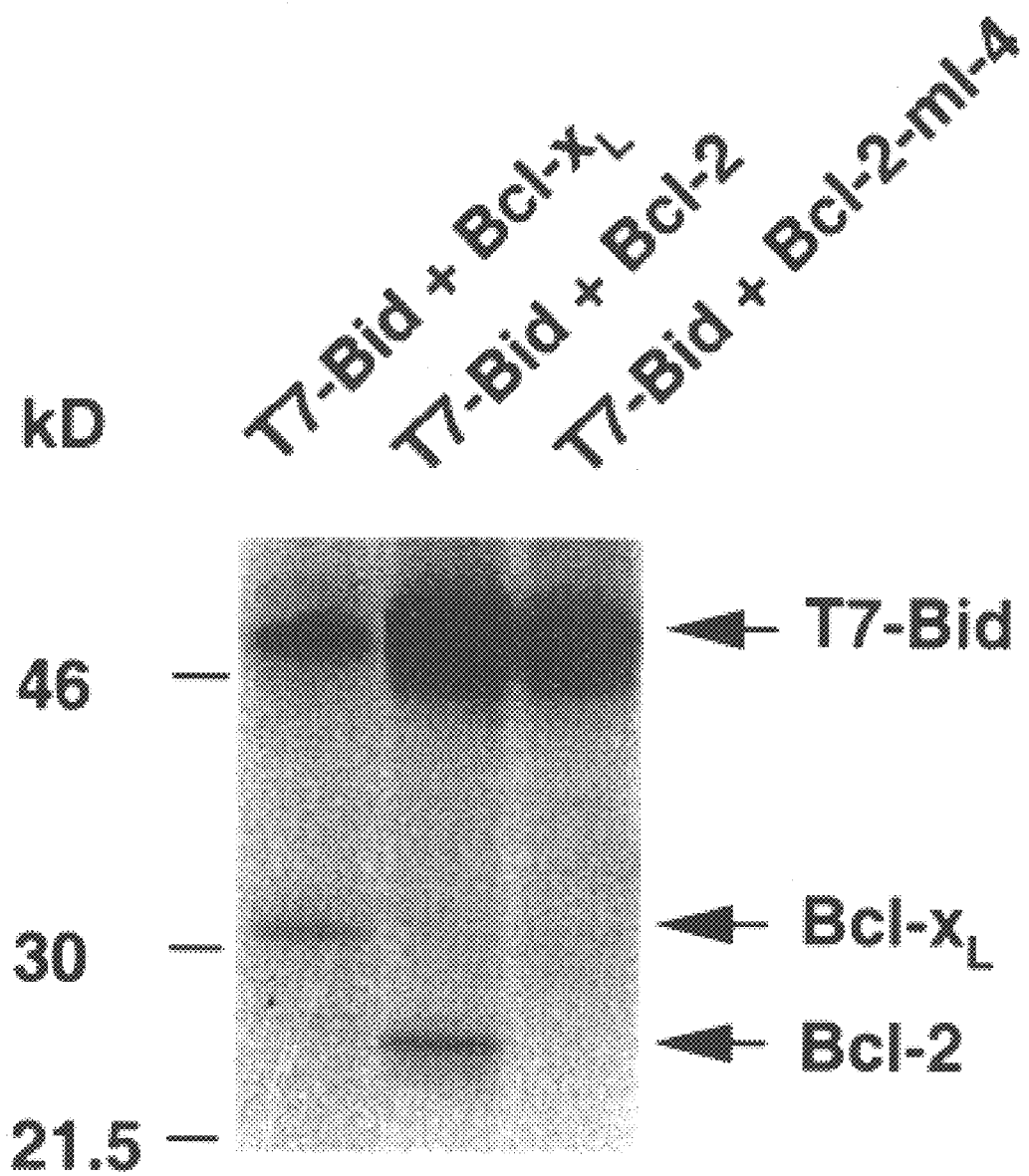
FIGS. 8A–D illustrate BID and BCL-2 family member interactions (FIG. 8A) in co-immunoprecipitation of T7-gene-10-BID fusion protein and BCL-$X_L$, BCL-2, BCL-2-mI4(G145E) expressed in NIH 3T3 cells.

Both BCL-$X_L$ and BCL-2 co-precipitated with the T7-gene-10-BID fusion protein, while a BH1 domain mutant, BCL-2-mI-4 (G145E), did not (FIG. 8A). However, we could not further assess the interaction between BID and BAX in this system since their co-expression markedly reduced the level of T7-gene-10-BID expression, apparently by inducing apoptosis of NIH 3T3 cells.

Figure 6C:
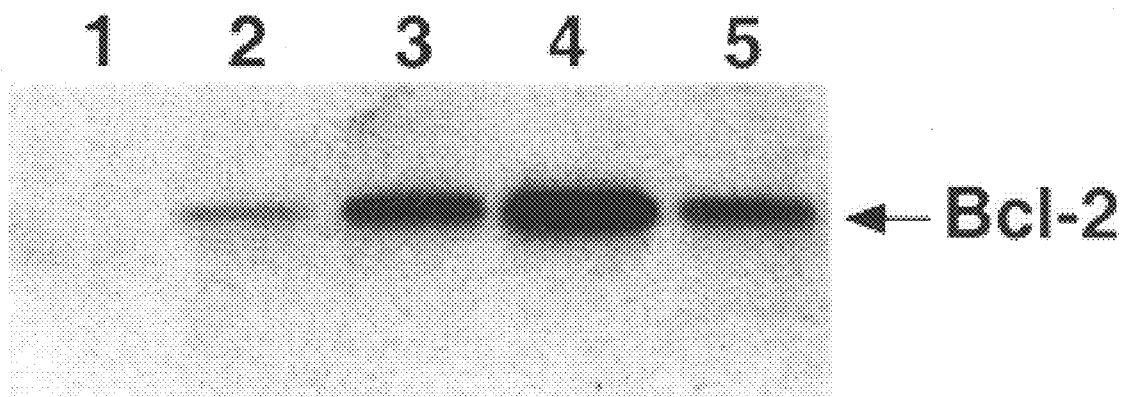

To confirm the in vivo interaction noted in transient transfections, we assessed whether BID would dimerize with BCL-2 at protein levels obtainable in the stably transfected FL5.12-Bcl-2 cells of example 4. BID was immunoprecipitated from the series of FL5.12 clones, and the immunoprecipitates were size-fractioned by SDS-PAGE followed by immunoblotting with an anti-human BCL-2 monoclonal antibody (6C8) (FIG. 6C). Parental FL5.12 cells contain no human BCL-2 (FIG. 6C, lane 1), while FL5.12-Bcl-2 cells (FIG. 6C, lane 2) demonstrated human BCL-2 bound to endogenous BID. Substantially more BCL-2 was heterodimerized in clones which overexpressed BID (FIG. 6C, lanes 3–5).

To further assess the sites of interaction between BID and BCL-2 family members we established an in vitro binding assay. Equal amounts of in vitro translated, $^{35}$S-labeled products of BAX, BCL-2, BCL-$X_L$ and BID were incubated with 1 µg of purified GST-BID fusion protein (wt or mutant) on ice for 30 min. 500 µl of NP-40 buffer with protease inhibitors was added to each binding mixture plus 25 µl of GSH-agarose and notated at 4° C. for 1–2 hrs. Materials bound to GSH-agarose were precipitated, washed three times in 1 ml of NP-40 buffer and solubilized in 25 µl of 1× SDS-PAGE sample buffer. Electrophoresis on 12.5% SDS-PAGE was followed by autoradiography.

Figure 8B:
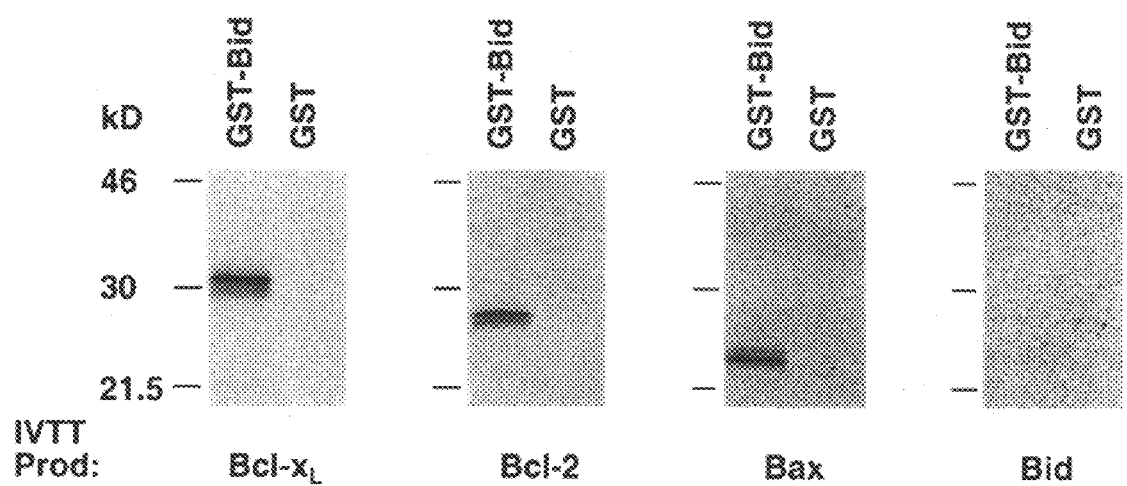

BCL-$X_L$, BCL-2 or BAX, but not BID, all bound to GST-BID, but not GST (FIG. 8B). This data was confirmed in a yeast two-hybrid system where BID was assayed in the DNA binding domain as well as the activation domain. The yeast two-hybrid assay was performed according to standard procedures which were briefly as follows. pBTM-Bid wt and mutants were co-transformed into yeast strain L40 (MATa his3D200 trpl-901 leu2–3,112 ade2 LYS2::(lexAop)$_4$-HIS3 URA3::(lexAop)$_8$-lacZ) with BCL-$X_L$, BCL-2, BAX or BID in pACTII. Transformants were grown on -Trp -Leu plates and assayed for β-gal activity as described previously (Sedlak et al., *Proc Natl Acad Sci U S A* 92: 7834–7838, 1995 which is incorporated by reference). BID interacted with BCL-$X_L$ but failed to homodimerize with itself in yeast two-hybrid assays (data not shown). Altogether these data indicated that BID exists as a monomer and can form dimers or perhaps multimers with both death agonists and antagonists.

In order to identify the domains within antagonists (BCL-2) and agonists (BAX) that interacted with BID, mutants of BCL-2 and BAX were tested in the in vitro binding assay. BCL-2mI-3 (G145A)mutants were generated as follows. An EcoRI fragment of human Bcl-2 CDNA was cloned into a modified pBluescript II Ks vector (Stratagene), whose SacI and BamHI sites had been eliminated. A 153 bp SacI/BamHI fragment containing the BH1 domain was replaced with a PCR-synthesized fragment containing substituted nucleotides. The mutated Bcl-2 cDNA was subsequently cloned into pGEM-4Z under the control of the Sp6 promoter for in vitro translation.

BAXmI-3 (G108A) and BAXmIII-3 (G67A), -4 (G67E) and -5(M74A) were generated as follows. An EcoRI/PstI (for BAXmI-3) or EcoRI/NheI (for BAXmIII-3,4 & %) fragment was PCR amplified from the 5' half of the murine Bax cDNA, respectively. Mutations were introduced into the 3' primers ending at the PstI or NheI site 226 bp or 349 bp into the open reading frame. For BAXmI-3 an HA Tag was added into the 5' primer. The amplified fragment plus the 3' half of the molecule were ligated into the EcoRI site of PBTM. The mutated Bax cDNA's were subsequently cloned into pGEM-4Z under the control of the Sp6 promoter for in vitro translation.

Figure 8C:
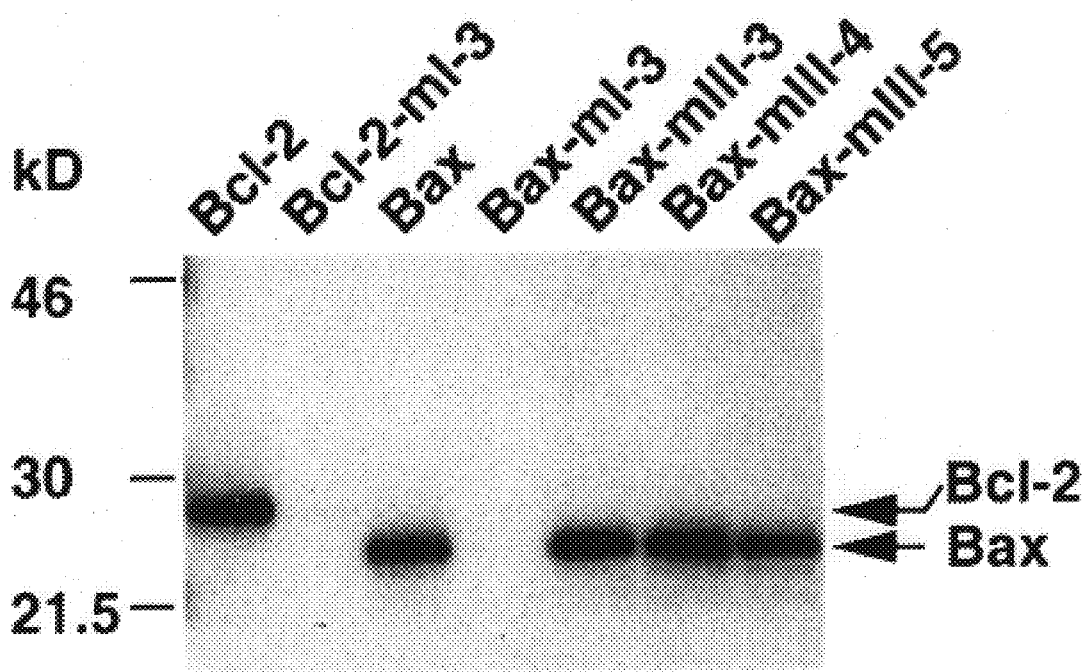

BCL-2mI-3 (G145A) and BAXmI-3 (G108A) have substituted the conserved Gly in the BH1 domain, and both failed to bind BID (FIG. 8C). BAXmIII-3 (G67A), mIII-4 (G67E) and mIII-5 (M74A), which bear mutations in the BH3 domain, still interacted with GST-BID (FIG. 8C). These results implicated the BH1 but excluded the BH3 domain as the site of interaction within the partner proteins that bind BID.

Figure 8D:
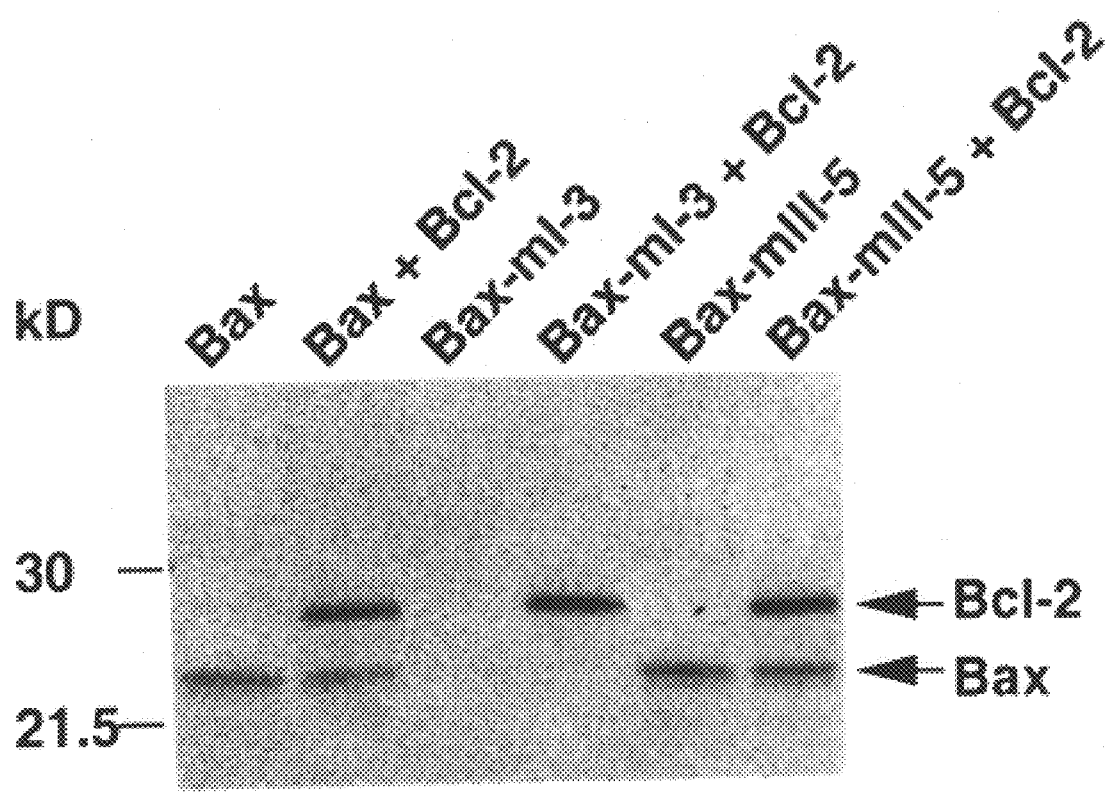

BID can interact with either BCL-2 or BAX, and BCL-2 heterodimerizes with BAX, raising the question of whether BID selectively interacts with BCL-2/BAX heterodimers or with each individual molecule. To address this, in vitro translated BCL-2 and BAX were pre-associated before being admixed with GST-BID (FIG. 8D). Compared to BAX alone, the presence of BCL-2/BAX heterodimers did not augment the binding to GST-BID (FIG. 8D). We next used BAXmI-3, a BH1 mutant which does not bind GST-BID, but still forms heterodimers with wild-type BCL-2 (data not shown). BAXmI-3 would not bind GST-BID even when heterodimerized with BCL-2 (FIG. 8D). These data suggest that BID does not form a tri-molecular complex with BCL-2/BAX heterodimers. To confirm this we performed the converse experiment using BAXmIII-5, a BH3 mutant, which does not form heterodimers with BCL-2 (unpublished data). The amount of BAXmIII-5 or wild-type BAX that bound GST-BID was similar and was unaffected by the presence of BCL-2 (FIG. 8D). In total these observations argue that BID interacts with monomeric or perhaps homodimeric BCL-2 or BAX, but not with BCL-2/BAX heterodimers.

EXAMPLE 7.

This example illustrates the effect of BH3 domain mutations on the death agonist activity of BID and the binding of BID to BCL-2 or BAX.

The only conserved domain that BID possesses is BH3, prompting a mutational assessment of its functional importance (FIG. 9A). BH3-mutant Bid constructs were generated in two steps. First, the 5' portion of the molecule was PCR amplified. The 5' primer added an EcoRI site, while the 3' primer ended at the NheI site 324 bp into the open reading frame. Second, the amplified EcoRIINheI fragment plus the 3' NheI/EcoRI fragment were ligated into the EcoRI site of pBTM. Subsequently, the entire insert was subcloned into pSFFV for transfection into F15.12 cells, pcDNA3 for transient transfection, pUHD10-3 for inducible clones in Jurkat cells and pGEX-HMK for GST-fusion proteins.

Figure 9B:
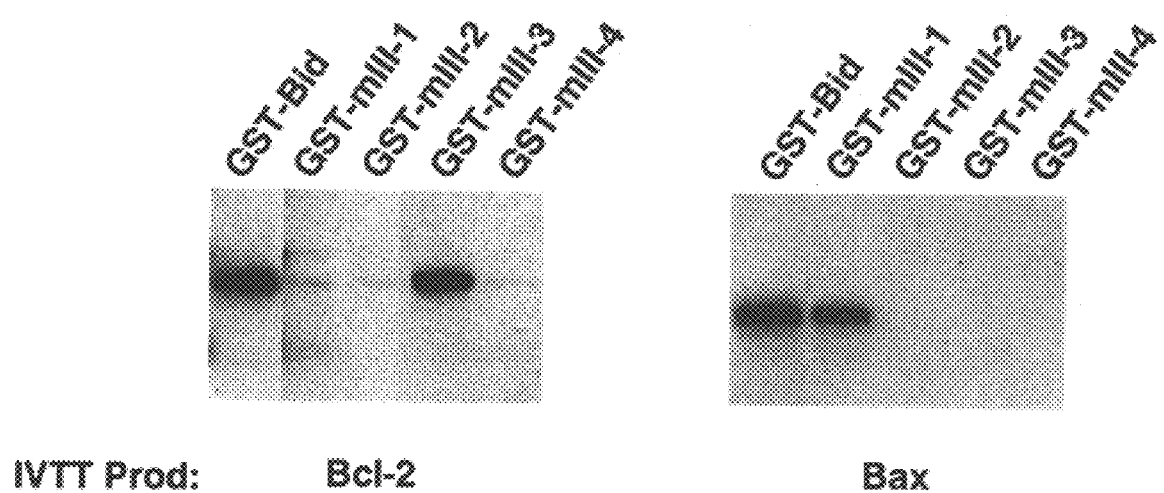
Figure 10A:
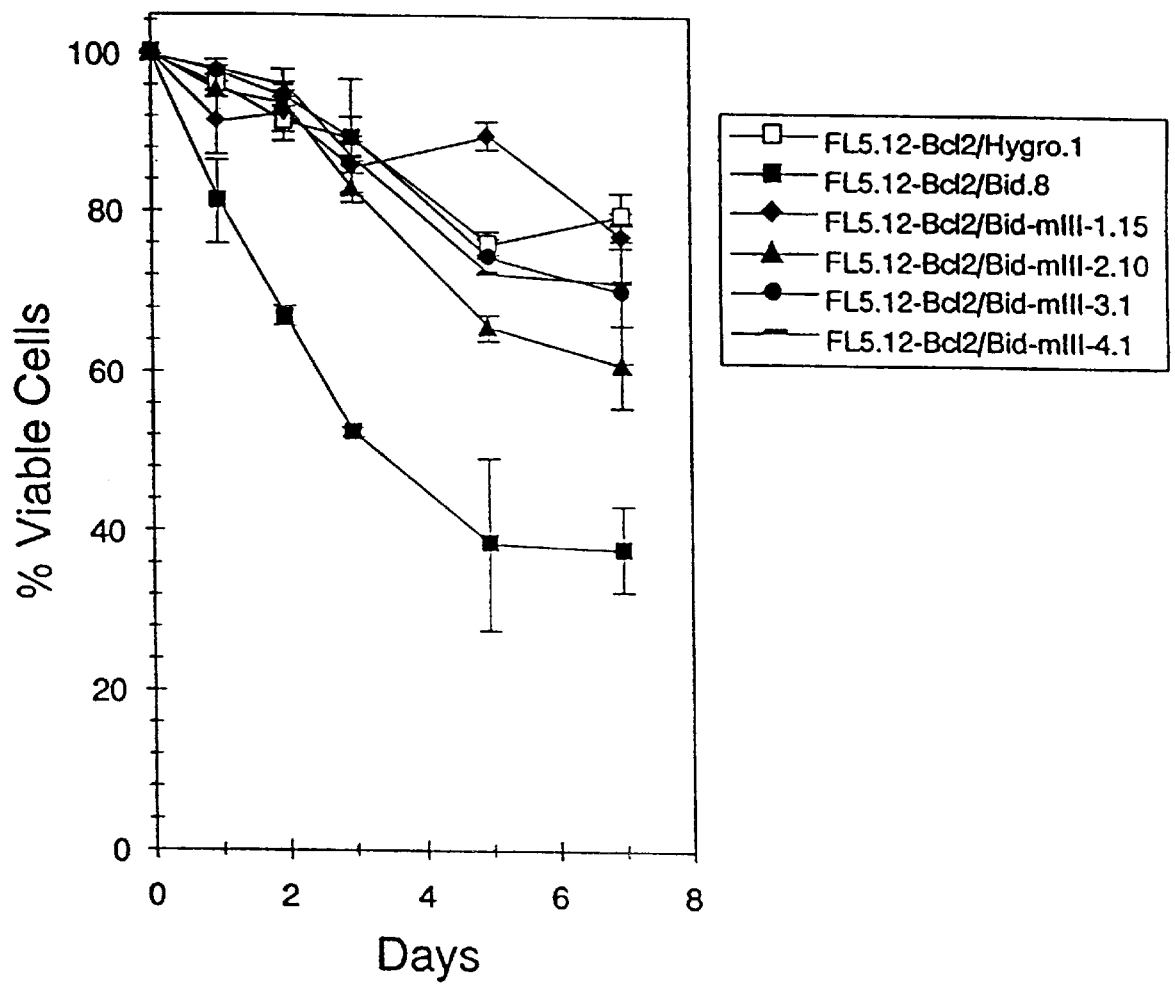
FIG. 10A–C illustrates (FIG. 9A) the viability of FL5.12-Bcl-2 clones expressing wild type or BH3-domain mutant BID, (FIG. 10B) Western blot showing BID expression and (FIG. 10C) Western blot showing association of wild type or BH3-domain mutant BID with BCL-2 and BAX (Lane 1: FL5.12-Bcl-2/Hygro.1; Lane 2: FL5.12-Bcl-2/Bid-8; Lane 3: FL5.12-Bcl-2/BidmIII-1.15; Lane 4: FL5.12-Bcl-2/BidmIII-2.10; Lane 5: FL5.12-Bcl-2/BidmIII-3.1; Lane 6: FL5.12-Bcl-2/BidmIII-4.1)
Figure 10B:
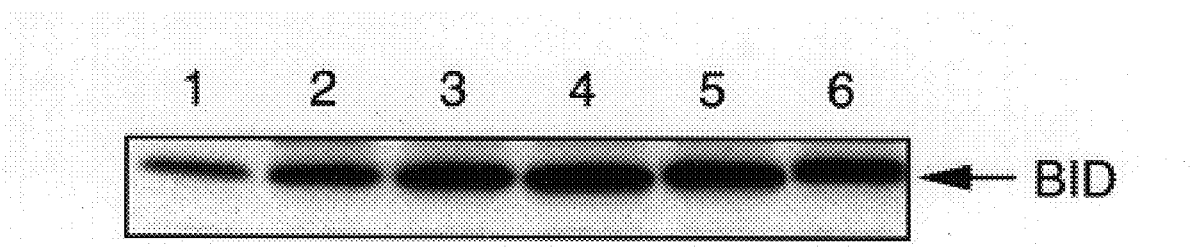
Figure 10C:
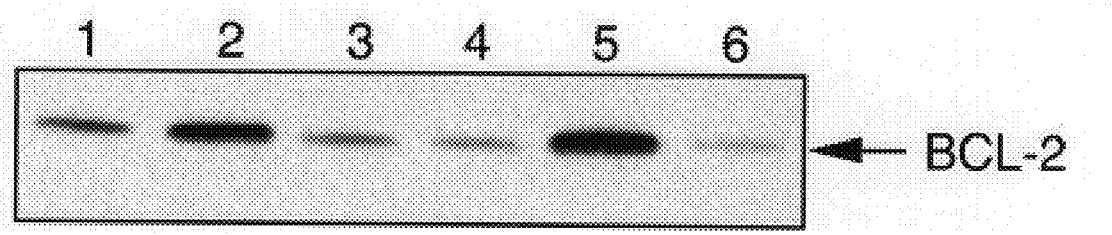

The BH3 mutants of BID were tested for their binding to BCL-2 and BAX in vitro (FIG. 9B). All four mutants tested disrupted BID's interaction with either BCL-2 or BAX. However, the mutants did display different specificities: BIDmIII-1 (M97A,D98A) bound to BAX but not to BCL-2, BIDmIII-3 (G94A) bound to BCL-2 but not BAX, whereas BIDmIII-2 and mIII-4 did not bind to either (FIG. 9B). To determine if this in vitro binding data accurately reflected interactions of the BID mutants in vivo, we introduced each BID mutant into FL5.12-Bcl-2 cells and selected stable expressing clones (FIG. 10A). The expression level of BID mutants was comparable to that of a wild-type BID transfectant (FIG. 10B). The ability of each mutant to interact with BCL-2 or BAX was assessed by immunoprecipitation with an anti-BID Ab followed by an anti-BCL-2 or anti-BAX immunoblot (FIG. 10C). Anti-human-BCL-2 monoclonal Ab 6C8 and biotinylated anti-murine-BAX polyclonal Ab 651 were used for blot analyses (1:2000 and 1:500, respectively). Wild-type BID (lane 2) and BIDmIII-3 (lane 5) interacted with BCL-2 whereas wild-type BID and BIDmIII-1 (lane 3) interacted with BAX in vivo, confirming the in vitro binding data. BIDmIII-1 was the only mutant which still interacted with BAX, albeit a decreased amount similar to the in vitro assay (FIG. 10C).

Figure 11A:
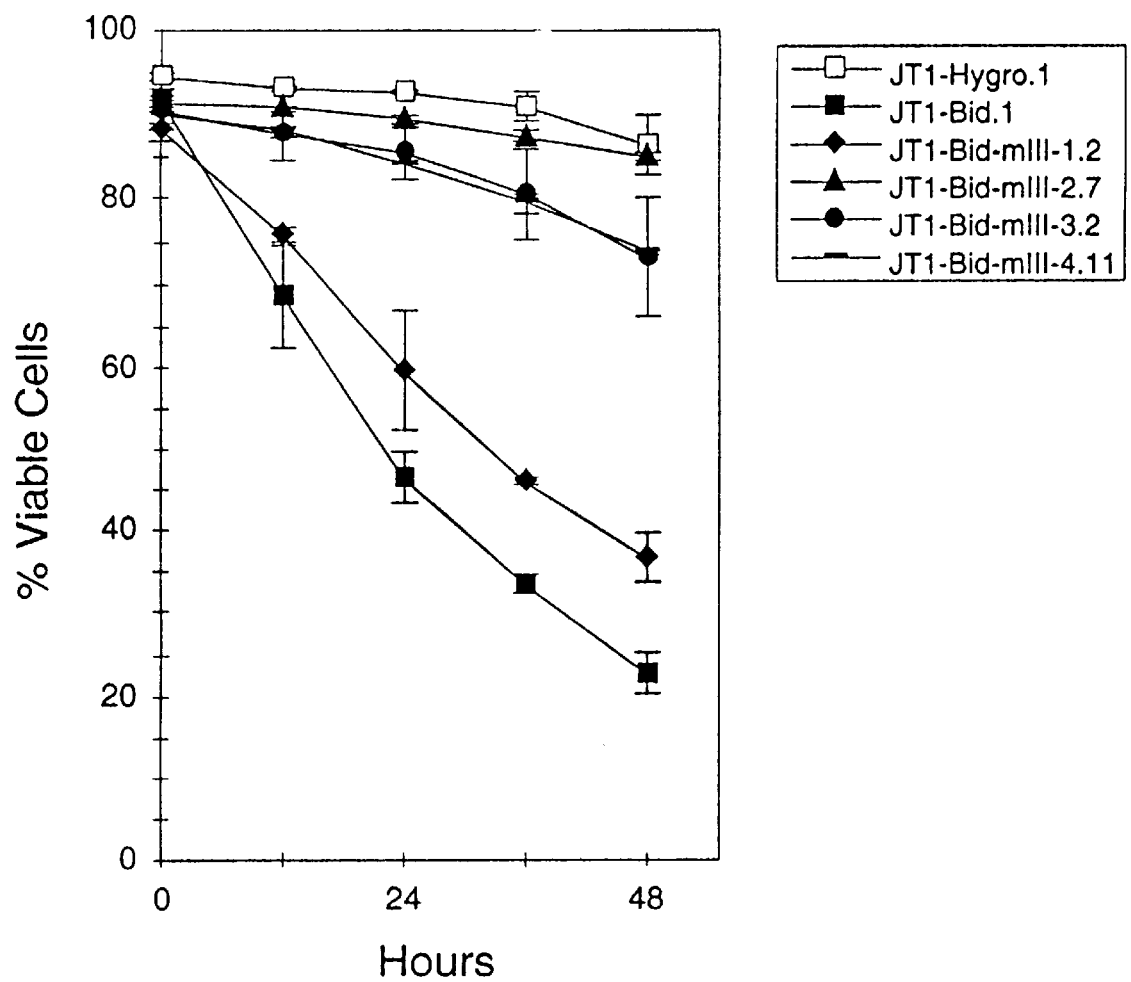
Figure 11C:
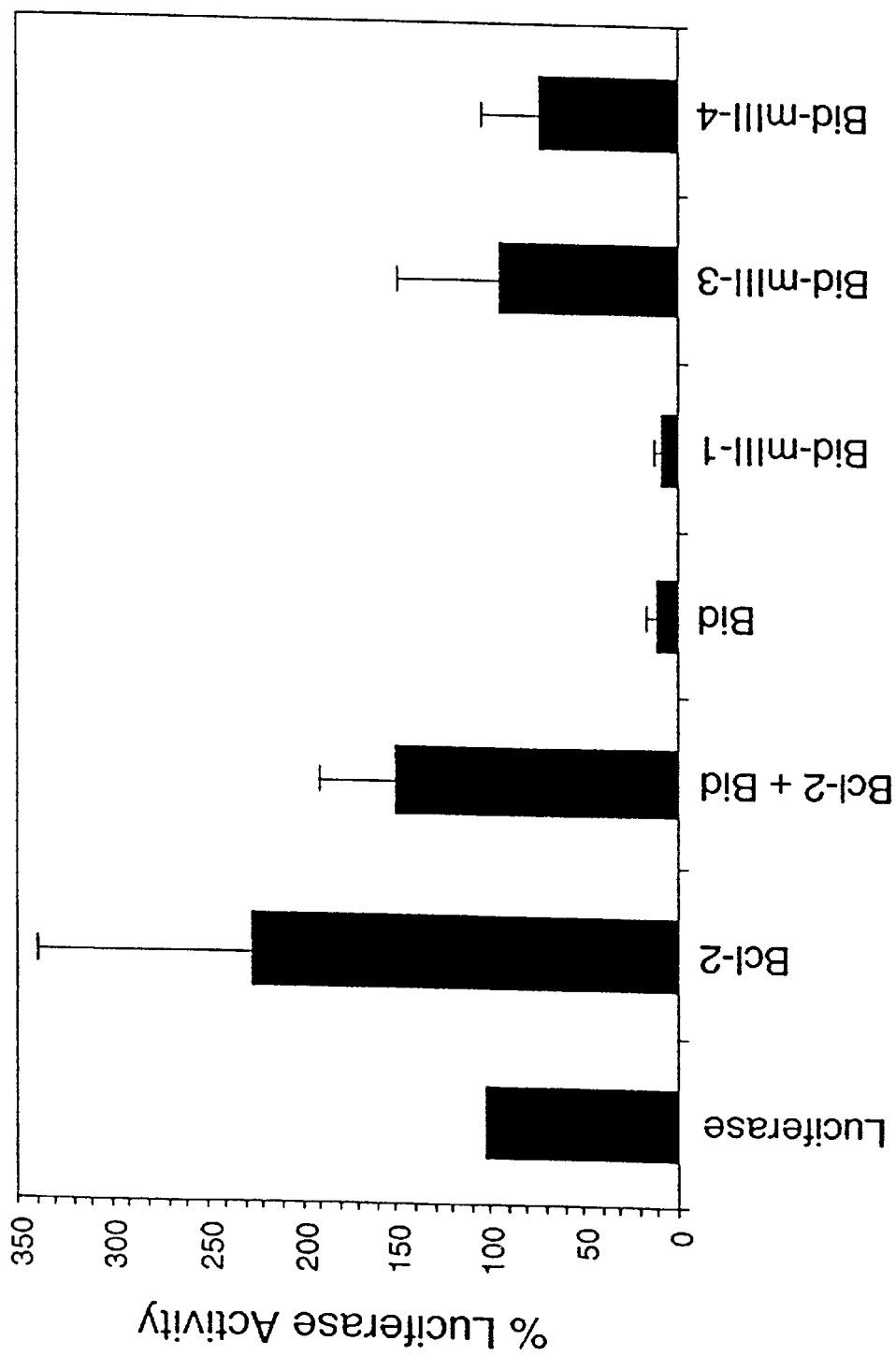

The capacity of BID mutants to counter protection by BCL-2 was assessed in the stably transfected FL5.12-Bcl-2 clones deprived of IL-3 (FIG. 10A). Of note, all BH3 mutants of BID were impaired in their capacity to counter protection by BCL-2. Even BIDmIII-3 (G94A) which still avidly heterodimerized with BCL-2 was less effective than wild-type BID. This dissociated the capacity of BID to form heterodimers with BCL-2 from its reversal of BCL-2 protection (FIG. 10A). This prompted further assessment of the BID mutants in the inducible system in Jurkat cells which does not require another apoptotic signal (FIG. 11A). Moreover, Jurkat cells do not express substantial amounts of BCL-2. Despite substantial levels of protein (FIG. 11B), BIDmIII-2,-3 & -4 displayed no meaningful death promoting effect (FIG. 11A). Only BIDmIII-1 demonstrated substantial killing that was somewhat less than wt BID (FIG. 11A), perhaps reflecting its weaker binding to BAX (FIGS. 9B and 10C). This BID mutant was also analyzed in the transient transfection death assay in Rat-1 fibroblasts. Once again, BIDmIII-1 demonstrated strong killing activity whereas, the activity of BIDmIII-3 & -4 was substantially impaired (FIG. 11C). Thus, the BH3 mutations in BID score differently in stable transfectants with high levels of BCL-2 that require an external death stimulus (IL-3 deprivation, FIG. 10A); when compared to systems which induce expression of BID and do not require another signal (FIGS. 11A and 11C). Of note, the only BID mutant (mIII-1) still active (M97A,D98A) bound BAX but not BCL-2 (FIGS. 9B and 10C).

Site specific mutagenesis of BID revealed that BH3 was required for death promoting activity. This included the capacity to counter protection by BCL-2 as well as induce a cysteine protease dependent apoptosis when expressed in Jurkat T cells or Rat-1 fibroblasts (Table 1).

TABLE 1

|  | BIDwt | BIDmIII-1 | BIDmIII-2 | BIDmIII-3 | BIDmIII-4 |
|---|---|---|---|---|---|
| Yeast Two-Hybrid Interactions with BCL-xL | + | − | − | + | − |
| In Vitro and In Vivo BCL-2 Binding | + | − | − | + | − |
| Counter BCL-2 *FL5.12-Bcl-2 | + | − | − | − | − |
| In Vitro and In Vivo BAX Binding | + | + | − | − | − |
| Death Agonist Activity |  |  |  |  |  |
| #Jurkat | + | + | − | − | − |
| •Rat-1 | + | + | ND | − | − |

*Ability to counteract BCL-2's death-inhibiting effect in FL5.12-Bcl = 2 cells following IL-3 withdrawal;
Ability to induce cell death in Jurkat cells following induction of BID expression by Doxycyclin treatment;
•Transient co-transfection of both Bid and Luciferase plasmids into Rat-1 cells assessed by Luciferase assay.

The requirement of an wild type BH3 domain in BID for its death promoting effect is consistent with prior deletion constructs in which 12 amino acids including the BH3 domain were eliminated from BAK, BAX and BIK (previously Bipl) resulting in reduced killing activity (Chittenden et al., Embo J 14: 5589–5596, 1995 which is incorporated by reference). In addition, a swap of a 23 amino acid segment surrounding BH3 from BAX into BCL-2 converted it to a death agonist (Hunter and Parslow, J Biol Chem 271: 8521–8524, 1996 which is incorporated by reference). The point mutations in BH3 of BID determined that the central glycine of BH3 was critical to apoptotic activity.

The point mutants of BID indicated that the BH3 domain is also required for interacting with BCL-2, BCL-$X_L$ or BAX (FIGS. 8, 9, 10, and Table 1). Conversely, point mutations of BCL-2 and BAX suggest that the BH1 domain (but do not exclude BH2) of partner proteins binds to BH3 (FIG. 8). The conservation of predicted α-helical regions in BCL-2 and BAX suggests that their 3-dimensional structure will be similar to that of BCL-$X_L$, with the reservation that a BCL-$X_L$ monomer was solved (Muchmore et al., Nature 381: 335–341, 1996 which is incorporated by reference). The point mutation information here argues that the BH3 domain of BID, an amphipathic α_helix, would bind the exposed hydrophobic amino acids of the cleft contributed by the BH1 domain of partner proteins.

Instructively, the various BH3 mutants of BID did not score identically in interations with BCL-2 and BAX or in death agonist assays. BIDmIII-3 (G94A) which binds BCL-2 but not BAX lost its capacity to counter BCL-2 and induce apoptosis. In contrast, BIDmIII-1 (M97A,D98A) still bound BAX but not BCL-2 and retained death agonist activity. A model consistent with all of the available data would embrace BID/BAX rather than BID/BCL-2 heterodimers as the critical, functional pair. Furthermore, the failure of BIDmIII-1 to counter BCL-2 protection dissociates the capacity of BID to reverse BCL-2 protection from its binding to BCL-2. This provides evidence that BID restores apoptosis in FL5.12-Bcl-2 cells by its death promoting activity that is independent of binding BCL-2 (Table 1). This could also explain why a weakened BIDmIII-1, which binds less avidly to BAX (FIGS. 9B and 10C) is unable to promote apoptosis in the more stringent assay in which cells are loaded with BCL-2 (FL5.12-Bcl-2, Table 1).

BCL-2 family members possessing COOH-terminal signal-anchor segments are integral membrane proteins predominantly localized to the mitochondrial outer membrane and nuclear envelope (Monaghan et al., J Histochem Cytochem 40: 1819–1825, 1992; Krajewski et al., Cancer Res 53: 4701–4714, 1993; Nguyen et al., J Biol Chem 268: 25265–25268, 1993; de Jong et al., Cancer Res 54: 256–260, 1994 which is incorporated by reference). Mutational analysis implicates BID/BAX as the key heterodimer. While not intending to be bound by a particular theory, these data suggest a model in which BAX would represent a membrane bound receptor and BID a "death ligand" that translocates between a free cytosolic and a membrane bound receptor site.

EXAMPLE 8

This example demonstrates that the BH3 domain in BID fragments and a fusion protein is sufficient to induce cell death.

Figure 12A:
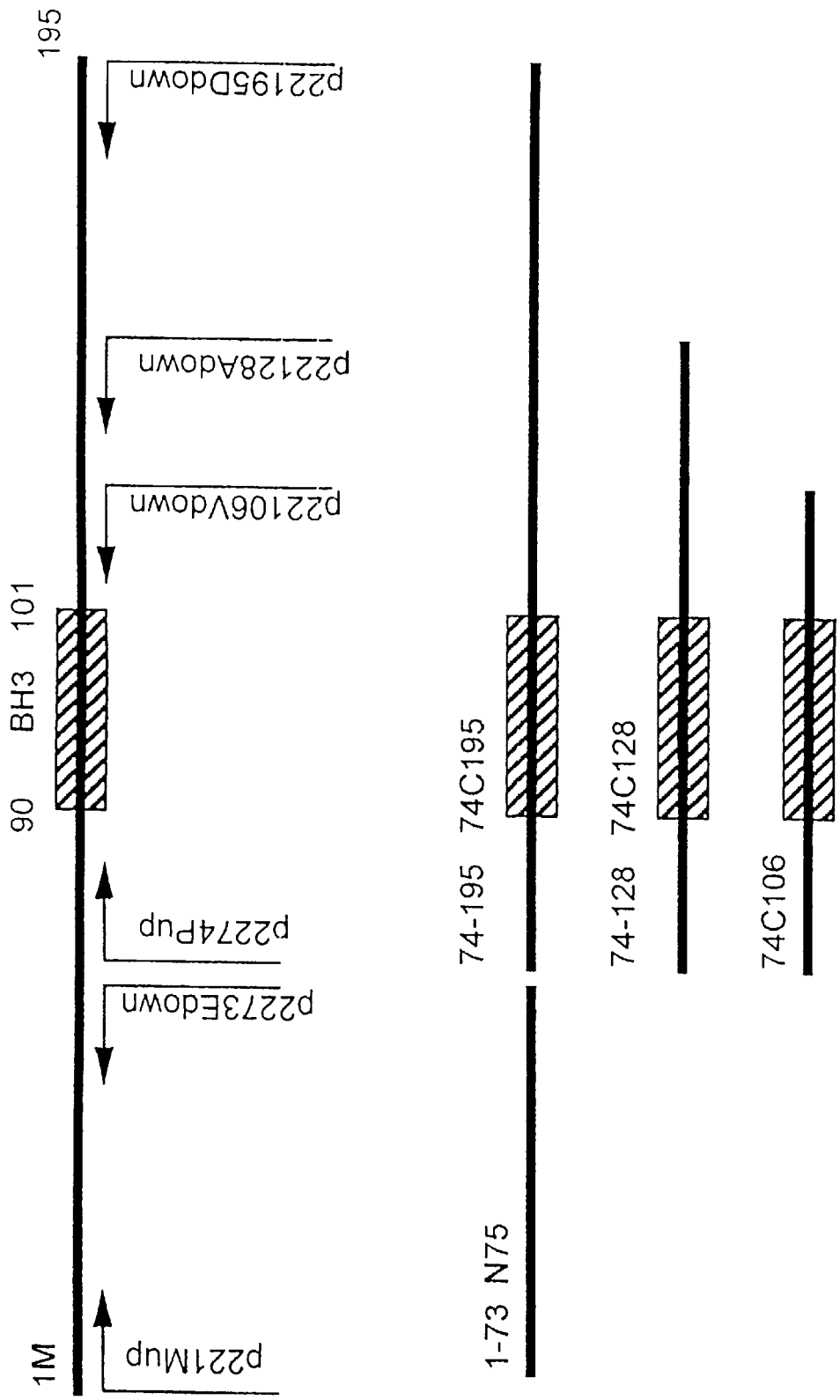

We made four different truncated BID polypeptides defined according to their amino acid positions referenced to full-length murine BID as follows: BID 1–73, BID 74–195, BID 74–128, and BID 74–106 (FIG. 12A; primers indicated by arrows). Each of these was separately cloned into pCDNA3 under CMV promoter and the constructs cotransfected into Rat-1 cells alone with a luciferase reporter gene as in example 5. The N-terminal fragment of BID (BID 1–73) did not induce cell death, whereas all the other constructs containing the BH3 domain did. In addition two short BID sequences (BID 81–100:EIIHNIARHLAQIGDEMDHN, SEQ ID NO: 85, and BID 84–98: HNIARHLAQIGDEMD, SEQ ID NO: 86) were made but not tested in the above system.

Figure 12C:
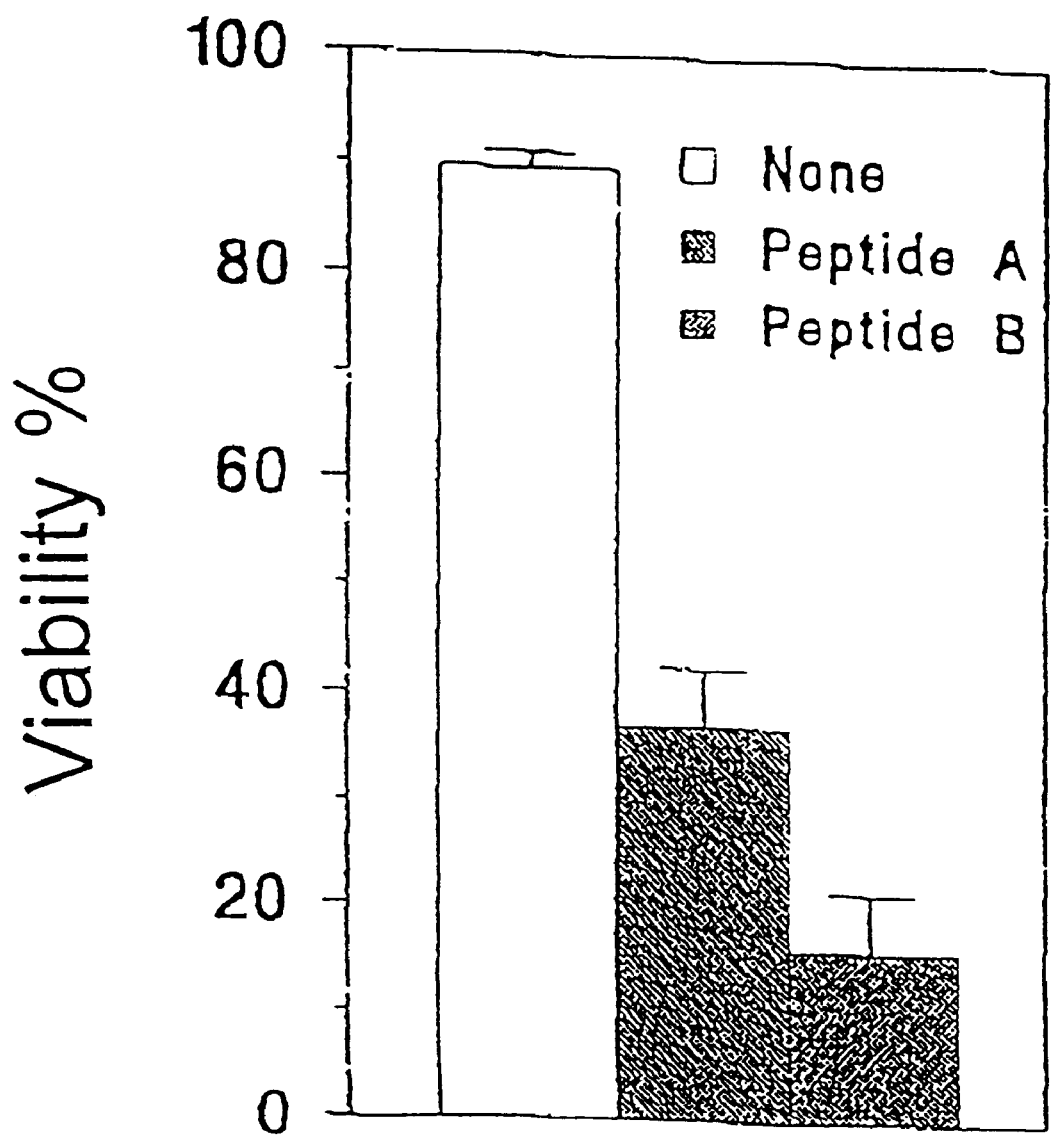

In order to determine whether an exogenously administered BH3 containing BID peptide can promote cell death, we constructed fusion proteins, which contains the tat protein sequence from HIV-1 and various sequences of murine BID which include the BH3 domain: BID(75–106)(SEQ ID NO: 55) (peptide A; SEQ ID NO: 56), BID(81–100)(SEQ ID NO: 85) (peptide B; SEQ ID NO: 87) and BID(84–98)(SEQ ID NO: 86) (peptide C; SEQ ID NO: 88)(FIG. 12B). The presence of the Tat sequence is believed to allow the peptide to penetrate into cells when added to a cell culture. As shown in FIG. 12C, treatment the murine T cell hybridoma 2B4 cells with the tat-BID(75–106) (SEQ ID NO: 56) or tat-BID (81–100) (SEQ ID NO: 87) fusion proteins (peptide A and peptide B, respectively) resulted in a reduction in cell viability determined by trypan blue dye exclusion at 19 and 43 hours compared to viability in control cells treated with medium alone. The tat-BID(84–98)(SEQ ID NO: 88) was not tested, however, it is believed that this fusion protein will also produce a reduction in cell viability. Thus, the BH3 domain of BID is sufficient to induce cell death when expressed by transformed cells or when administered exogenously coupled to the carrier HIV-1 tat peptide.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. An isolated and purified polynucleotide or a polynucleotide complementary thereto, wherein the polynucleotide comprises a nucleotide sequence which encodes a mammalian bcl-homology-domain-3-interacting-domain-death-agonist (BIH3-interacting-domain-death-agonist (BID)) polypeptide which (a) lacks a carboxyl terminal signal-anchor sequence characteristic of membrane bound BCL-2 family members, (b) lacks bcl-homology-domains 1 and 2, (c) has a BH3 domain, (d) heterodimerizes with BAX, BCl,-2 and BCL-$X_L$, and (e) has at least 85% sequence conservation with SEQ ID NO:4, SEQ ID NO:5, or SEQ ID NO:6.

2. The polynucleotide or polynucleotide fully complementary thereto of claim 1 wherein said polynucleotide comprises a nucleotide sequence as set forth in SEQ ID NO:1.

3. The polynucleotide or polynucleotide fully complementary thereto of claim 1 wherein said polynucleotide comprises a nucleotide sequence as set forth in SEQ ID NO:2 or SEQ ID NO:3.

4. An isolated and purified polynucleotide or polynucleotide fully complementary thereto, wherein the polynucleotide comprises a nucleotide sequence encoding a fusion protein comprising SEQ ID NO:54 and at least 10 consecutive amino acids of SEQ ID NO:4, SEQ ID NO:5, or SEQ ID NO:6.

5. The polynucleotide or polynucleotide complementary thereto of claim 4, wherein the polynucleotide encodes a fusion protein having an amino acid sequence as set forth in SEQ ID NO:56.

6. An isolated and purified polynucleotide comprising a nucleotide sequence which encodes a human bcl-homology-domain-3-interacting-domain-death-agonist (BH3-interacting-domain-death-agonist(BID)) polypeptide or a polynucleotide fully complementary thereto, wherein the BID polypeptide comprises an amino acid sequence which has at least 85 percent conservation with the amino acid sequence set forth in SEQ ID NO:4, SEQ ID NO:5, or SEQ ID NO:6, and wherein the complementary polynucleotide specifically hybridizes to SEQ ID NO:1, SEQ ID NO:2 or SEQ ID NO:3.

7. The polynucleotide or polynucleotide fully complementary thereto of claim 6, wherein the BID polypeptide comprises an amino acid sequence which is at least 85 percent identical to the amino acid sequence set forth in SEQ ID NO:4 and wherein the complementary polynucleotide specifically hybridizes to SEQ ID NO:1.

8. The polynucleotide or polynucleotide fully complementary thereto of claim 7, wherein the BID polypeptide comprises an amino acid sequence which has at least 95 percent conservation with the amino acid sequence set forth in SEQ ID NO:4 and the complementary polynucleotide specifically hybridizes to SEQ ID NO:1.

9. The polynucleotide or polynucleotide fully complementary thereto of claim 8, wherein the BID polypeptide comprises an amino acid sequence which is at least 95 percent identical to the amino acid sequence set forth in SEQ ID NO:4 and the complementary polynucleotide specifically hybridizes to SEQ ID NO:1.

10. A vector comprising expression regulatory elements operably linked to the polynucleotide or polynucleotide fully complementary thereto of claim 1.

11. A host cell transformed with the vector of claim 10.

12. A vector comprising expression regulatory elements operably linked to the polynucleotide or polynucleotide fully complementary thereto of claim 6.

13. A host cell transforced with the vector of claim 12.

14. A composition comprising:

(a) a fusion gene comprising the polynucleotide of claim 1 fused in frame to a polynucleotide encoding a DNA-binding domain of a transcriptional activator protein;

(b) a fusion gene comprising a sequence encoding BAX, BCL-2 or BCL-$X_L$ fused in frame to a polynucleotide encoding a DNA-binding domain of the transcriptional activator protein of (a); and (c) a reporter gene functionally linked to a transcriptional regulatory element whose transcriptional activity is dependent upon the amount of a heterodimer or peptides encoded by fusion genes of (a) and (b).

15. The composition of claim 14, wherein the transcriptional activator protein is the yeast GAL4 transcription protein.

16. The composition of claim 15, wherein the reporter gene is β-galactosidase.

* * * * *

SEQUENCE LISTING (1) GENERAL INFORMATION:

(iii) NUMBER OF SEQUENCES: 88

(2) INFORMATION FOR SEQ ID NO:1:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

| | | | | | |
|---|---|---|---|---|---|
| ATGGACTGTG | AGGTCAACAA | CGGTTCCAGC | CTCAGGGATG | AGTGCATCAC | AAACCTACTG | 60 |
| GTGTTTGGCT | TCCTCCAAAG | CTGTTCTGAC | AACAGCTTCC | GCAGAGAGCT | GGACGCACTG | 120 |
| GGCCACGAGC | TGCCAGTGCT | GGCTCCCCAG | TGGGAGGGCT | ACGATGAGCT | GCAGACTGAT | 180 |
| GGCAACCGCA | GCAGCCACTC | CCGCTTGGGA | AGAATAGAGG | CAGATTCTGA | AAGTCAAGAA | 240 |
| GACATCATCC | GGAATATTGC | CAGGCACCTC | GCCCAGGTCG | GGACAGCAT | GGACCGTAGC | 300 |
| ATCCCTCCGG | GCCTGGTGAA | CGGCCTGGCC | CTGCAGCTCA | GGAACACCAG | CCGGTCGGAG | 360 |
| GAGGACCGGA | ACAGGGACCT | GGCCACTGCC | CTGGAGCAGC | TGCTGCAGGC | CTACCCTAGA | 420 |
| GACATGGAGA | AGGAGAAGAC | CATGCTGGTG | CTGGCCCTGC | TGCTGGCCAA | GAAGGTGGCC | 480 |
| AGTCACACGC | CGTCCTTGGC | TCCGTGATGT | CTTTCACACA | ACAGTAATTT | TATTAACCAG | 540 |
| AACCTACGCA | CCTACGTGAG | GAGCTTAGCC | AGAAATGGGA | TGGACTGA | | 588 |

(2) INFORMATION FOR SEQ ID NO:2:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| | | | | | |
|---|---|---|---|---|---|
| ATGGACTGTG | AGGTCAACAA | CGGTTCCAGC | CTCAGGGATG | AGTGCATCAC | AAACCTACTG | 60 |
| GTGTTTGGCT | TCCTCCAAAG | CTGTTCTGAC | AACAGCTTCC | GCAGAGAGCT | GGACGCACTG | 120 |
| GGCCACGAGC | TGCCAGTGCT | GGCTCCCCAG | TGGGAGGGCT | ACGATGAGCT | GCAGACTGAT | 180 |
| GGCAACCGCA | GCAGCCACTC | CCGCTTGGGA | AGAATAGAGG | CAGATTCTGA | AAGTCAAGAA | 240 |
| GACATCATCC | GGAATATTGC | CAGGCACCTC | GCCCAGGTCG | GGACAGCAT | GGACCGTAGC | 300 |
| ATCCCTCCGG | GCCTGGTGAA | CGGCCTGGCC | CTGCAGCTCA | GGAACACCAG | CCGGTCGGAG | 360 |
| GAGGACCGGA | ACAGGGACCT | GGCCACTGCC | CTGGAGCAGC | TGCTGCAGGC | CTACCCTAGA | 420 |
| GACATGGAGA | AGGAGAAGAC | CATGCTGGTG | CTGGCCCTGC | TGCTGGCCAA | GAAGGTGGCC | 480 |
| AGTCACACGC | CGTCCTTGGC | TCCGTGATGT | CTTTCACACA | ACAGTAATTT | TATTAACCAG | 540 |
| AACCTACGCA | CCTACGTGAG | GAGCTTAGCC | AGAAATGTAA | GAACCCTTGA | GGGGATGGAC | 600 |
| TGA | | | | | | 603 |

(2) INFORMATION FOR SEQ ID NO:3:

(i) SEQUENCE CHARACTERISTICS:
        (A) LENGTH: 588 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

```
ATGGACTCTG AGGTCAGCAA CGGTTCCGGC CTGGGGGCCA AGCACATCAC AGACCTGCTG      60

GTGTTCGGCT TTCTCCAAAG CTCTGGCTGT ACTCGCCAAG AGCTGGAGGT GCTGGGTCGG     120

GAACTGCCTG TGCAAGCTTA CTGGGAGGCA GACCTCGAAG ACGAGCTGCA GACAGACGGC     180

AGCCAGGCCA GCCGCTCCTT CAACCAAGGA AGAATAGAGC CAGATTCTGA AAGTCAGGAA     240

GAAATCATCC ACAACATTGC CAGACATCTC GCCCAAATAG GCGATGAGAT GGACCACAAC     300

ATCCAGCCCA CACTGGTGAG ACAGCTAGCC GCACAGTTCA TGAATGGCAG CCTGTCGGAG     360

GAAGACAAAA GGAACTGCCT GGCCAAAGCC CTTGATGAGG TGAAGACAGC CTTCCCCAGA     420

GACATGGAGA ACGACAAGGC CATGCTGATA ATGACAATGC TGTTGGCCAA AAAAGTGGCC     480

AGTCACGCAC CATCTTTGCT CCGTGATGTC TTCCACACGA CTGTCAACTT TATTAACCAG     540

AACCTATTCT CCTATGTGAG GAACTTGGTT AGAAACGAGA TGGACTGA                  588
```

(2) INFORMATION FOR SEQ ID NO:4:

(i) SEQUENCE CHARACTERISTICS:
(A) LENGTH: 195 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:4:

```
Met Asp Cys Glu Val Asn Asn Gly Ser Ser Leu Arg Asp Glu Cys Ile
  1               5                  10                  15

Thr Asn Leu Leu Val Phe Gly Phe Leu Gln Ser Cys Ser Asp Asn Ser
             20                  25                  30

Phe Arg Arg Glu Leu Asp Ala Leu Gly His Glu Leu Pro Val Leu Ala
         35                  40                  45

Pro Gln Trp Glu Gly Tyr Asp Glu Leu Gln Thr Asp Gly Asn Arg Ser
     50                  55                  60

Ser His Ser Arg Leu Gly Arg Ile Glu Ala Asp Ser Glu Ser Gln Glu
 65                  70                  75                  80

Asp Ile Ile Arg Asn Ile Ala Arg His Leu Ala Gln Val Gly Asp Ser
                 85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
            180                 185                 190

Gly Met Asp
        195
```

(2) INFORMATION FOR SEQ ID NO:5:

(i) SEQUENCE CHARACTERISTICS:
        (A) LENGTH: 200 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Met Asp Cys Glu Val Asn Asn Gly Ser Ser Leu Arg Asp Glu Cys Ile
 1               5                  10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
            180                 185                 190

Val Arg Thr Leu Glu Gly Met Asp
        195                 200
```

(2) INFORMATION FOR SEQ ID NO:6:

(i) SEQUENCE CHARACTERISTICS:
        (A) LENGTH: 195 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Met Asp Ser Glu Val Ser Asn Gly Ser Gly Leu Gly Ala Lys His Ile
 1               5                  10                  15

Thr Asp Leu Leu Val Phe Gly Phe Leu Gln Ser Ser Gly Cys Thr Arg
            20                  25                  30

Gln Glu Leu Glu Val Leu Gly Arg Glu Leu Pro Val Gln Ala Tyr Trp
        35                  40                  45

Glu Ala Asp Leu Glu Asp Glu Leu Gln Thr Asp Gly Ser Gln Ala Ser
50                  55                  60

Arg Ser Phe Asn Gln Gly Arg Ile Glu Pro Asp Ser Glu Ser Gln Glu
65                  70                  75                  80
```

```
        Glu Ile Ile His Asn Ile Ala Arg His Leu Ala Gln Ile Gly Asp Glu
                        85                  90                  95

Met Asp His Asn Ile Gln Pro Thr Leu Val Arg Gln Leu Ala Ala Gln
                    100                 105                 110

Phe Met Asn Gly Ser Leu Ser Glu Glu Asp Lys Arg Asn Cys Leu Ala
                    115                 120                 125

Lys Ala Leu Asp Glu Val Lys Thr Ala Phe Pro Arg Asp Met Glu Asn
            130                 135                 140

Asp Lys Ala Met Leu Ile Met Thr Met Leu Leu Ala Lys Lys Val Ala
        145                 150                 155                 160

Ser His Ala Pro Ser Leu Leu Arg Asp Val Phe His Thr Thr Val Asn
                        165                 170                 175

Phe Ile Asn Gln Asn Leu Phe Ser Tyr Val Arg Asn Leu Val Arg Asn
                        180                 185                 190

Glu Met Asp
                195

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "ISOLEUCINE OR VALINE"

(ix) FEATURE:
        (A) NAME/KEY: Modified-site
        (B) LOCATION: 7
        (D) OTHER INFORMATION: /note= "GLUTAMIC ACID OR SERINE"

(xi) SEQUENCE DESCRIPTION: SEQ ID NO:7:

Leu Ala Glu Xaa Gly Asp Xaa Met Asp
    1               5

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Leu Ala Glu Val Gly Asp Ser Met Asp
    1               5

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

ATGGACTGTG AGGTCAACAA CGGTTCCAGC C                                      31
```

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TCAGGGATGA GTGCATCACA AACCTACTGG TGTTTGG                              37

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CTTCCTCCAA AGCTGTTCTG ACAACAGCTT CCG                                    33

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CAGAGAGCTG GACGCACTGG GCCAC                                                  25

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GAGCTGCCAG TGCTGGCTCC CC                                                      22

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

AGTGGGAGGG CTACGATGAG CTGCAG                                              26

(2) INFORMATION FOR SEQ ID NO:15:

(i) SEQUENCE CHARACTERISTICS:

(A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ACTGATGGCA ACCGCAGCAG CCACTC                                          26

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CCGCTTGGGA AGAATAGAGG CAGATTCTGA AAG                                  33

(2) INFORMATION FOR SEQ ID NO:17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TCAAGAAGAC ATCATCCGGA ATATTGCCAG GCAC                                 34

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CTCGCCCAGG TCGGGACAG CATGGAC                                          27

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CGTAGCATCC CTCCGGGCCT GGTGAAC                                         27

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GGCCTGGCCC TGCAGCTCAG GAACAC                                      26

(2) INFORMATION FOR SEQ ID NO:21:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:21:

CAGCCGGTCG GAGGAGGACC GGAAC                                       25

(2) INFORMATION FOR SEQ ID NO:22:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:22:

AGGGACCTGG CCACTGCCCT GGAG                                        24

(2) INFORMATION FOR SEQ ID NO:23:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:23:

CAGCTGCTGC AGGCCTACCC TAGAGAC                                     27

(2) INFORMATION FOR SEQ ID NO:24:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:24:

ATGGAGAAGG AGAAGACCAT GCTGGTGCTG G                                31

(2) INFORMATION FOR SEQ ID NO:25:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:25:

CCCTGCTGCT GGCCAAGAAG GTGGC                                       25

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CAGTCACACG CCGTCCTTGG CTCCG                        25

(2) INFORMATION FOR SEQ ID NO:27:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TGATGTCTTT CACACAACAG TAATTTTATT AACCAGAACC TACGCACC        48

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

TACGTGAGGA GCTTAGCCAG AAATGGGATG GACTGA               36

(2) INFORMATION FOR SEQ ID NO:29:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Met Asp Cys Glu Val Asn Asn Gly Ser Ser Leu Arg Asp Glu Cys
1           5                  10               15

(2) INFORMATION FOR SEQ ID NO:30:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

Ile Thr Asn Leu Leu Val Phe Gly Phe Leu Gln Ser Cys Ser Asp Asn
1           5                  10               15

Ser Phe Arg (2) INFORMATION FOR SEQ ID NO:31:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Arg Glu Leu Asp Ala Leu Gly His Glu Leu Pro Val Leu Ala Pro Gln
    1               5                  10                  15

Trp Glu Gly Tyr Asp Glu Leu Gln Thr
                20                  25

(2) INFORMATION FOR SEQ ID NO:32:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

Asp Gly Asn Arg Ser Ser His Ser Arg Leu Gly Arg Ile Glu Ala Asp
    1               5                  10                  15

Ser Glu Ser Gln Glu Asp Ile Ile
                20

(2) INFORMATION FOR SEQ ID NO:33:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

Arg Asn Ile Ala Arg His Leu Ala Gln Val Gly Asp Ser Met Asp Arg
    1               5                  10                  15

Ser Ile Pro Pro Gly Leu Val Asn Gly Leu Ala Leu Gln
                20                  25

(2) INFORMATION FOR SEQ ID NO:34:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

Leu Arg Asn Thr Ser Arg Ser Glu Glu Asp Arg Asn Arg
    1               5                  10

(2) INFORMATION FOR SEQ ID NO:35:

(i) SEQUENCE CHARACTERISTICS:
        (A) LENGTH: 25 amino acids
        (B) TYPE: amino acid
        (C) STRANDEDNESS:

-continued (D) TOPOLOGY: linear (ii) MOLECULE TYPE: peptide (xi) SEQUENCE DESCRIPTION: SEQ ID NO:35:

Asp Leu Ala Thr Ala Leu Glu Gln Leu Leu Gln Ala Tyr Pro Arg Asp
    1               5                  10                  15

Met Glu Lys Glu Lys Thr Met Leu Val
                20                  25

(2) INFORMATION FOR SEQ ID NO:36:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Leu Ala Leu Leu Leu Ala Lys Lys Val Ala Ser His Thr Pro Ser Leu
    1               5                  10                  15

Leu Arg Asp Val Phe His Thr Thr Val Asn Phe Ile
                20                  25

(2) INFORMATION FOR SEQ ID NO:37:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

Asn Gln Asn Leu Arg Thr Tyr Val Arg Ser Leu Ala Arg Asn Gly Met
    1               5                  10                  15

Asp (2) INFORMATION FOR SEQ ID NO:38:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

Leu Ala Ile Ile Gly Asp Asp Ile Asn
    1               5

(2) INFORMATION FOR SEQ ID NO:39:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Leu Arg Arg Ile Gly Asp Glu Leu Asp
    1               5

(2) INFORMATION FOR SEQ ID NO:40:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

Leu Ala Cys Ile Gly Asp Glu Met Asp
1          5

(2) INFORMATION FOR SEQ ID NO:41:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

Leu Ala Gln Ile Gly Asp Glu Met Asp
1          5

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

Arg Gln Leu Ala Ile Ile Gly Asp Asp Ile Asn Arg Arg
1          5                  10

(2) INFORMATION FOR SEQ ID NO:43:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

Glu Cys Leu Arg Arg Ile Gly Asp Glu Leu Asp Ser Asn
1          5                  10

(2) INFORMATION FOR SEQ ID NO:44:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Leu Arg Leu Ala Cys Ile Gly Asp Glu Met Asp Val Ser
1          5                  10

-continued (2) INFORMATION FOR SEQ ID NO:45:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

Arg His Leu Ala Gln Ile Gly Asp Glu Met Asp His Asn
1               5                   10

(2) INFORMATION FOR SEQ ID NO:46:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

Leu Ala Gln Ile Gly Asp Glu Ala Ala
1               5

(2) INFORMATION FOR SEQ ID NO:47:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:47:

Leu Ala Gln Ala Ala Ala Ala Met Asp
1               5

(2) INFORMATION FOR SEQ ID NO:48:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:48:

Leu Ala Gln Ile Ala Asp Glu Met Asp
1               5

(2) INFORMATION FOR SEQ ID NO:49:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:49:

Leu Ala Gln Ile Glu Asp Glu Met Asp
1               5

(2) INFORMATION FOR SEQ ID NO:50:

(i) SEQUENCE CHARACTERISTICS:
　　　　(A) LENGTH: 73 amino acids
　　　　(B) TYPE: amino acid
　　　　(C) STRANDEDNESS:
　　　　(D) TOPOLOGY: linear (ii) MOLECULE TYPE: protein (xi) SEQUENCE DESCRIPTION: SEQ ID NO:50:

Met Asp Ser Glu Val Ser Asn Gly Ser Gly Leu Gly Ala Lys His Ile
1               5                   10                  15

Thr Asp Leu Leu Val Phe Gly Phe Leu Gln Ser Ser Gly Cys Thr Arg
            20                  25                  30

Gln Glu Leu Glu Val Leu Gly Arg Glu Leu Pro Val Gln Ala Tyr Trp
        35                  40                  45

Glu Ala Asp Leu Glu Asp Glu Leu Gln Thr Asp Gly Ser Gln Ala Ser
    50                  55                  60

Arg Ser Phe Asn Gln Gly Arg Ile Glu
65                  70

(2) INFORMATION FOR SEQ ID NO:51:

(i) SEQUENCE CHARACTERISTICS:
　　　　(A) LENGTH: 122 amino acids
　　　　(B) TYPE: amino acid
　　　　(C) STRANDEDNESS:
　　　　(D) TOPOLOGY: linear (ii) MOLECULE TYPE: protein (xi) SEQUENCE DESCRIPTION: SEQ ID NO:51:

Pro Asp Ser Glu Ser Gln Glu Glu Ile Ile His Asn Ile Ala Arg His
1               5                   10                  15

Leu Ala Gln Ile Gly Asp Glu Met Asp His Asn Ile Gln Pro Thr Leu
            20                  25                  30

Val Arg Gln Leu Ala Ala Gln Phe Met Asn Gly Ser Leu Ser Glu Glu
        35                  40                  45

Asp Lys Arg Asn Cys Leu Ala Lys Ala Leu Asp Glu Val Lys Thr Ala
    50                  55                  60

Phe Pro Arg Asp Met Glu Asn Asp Lys Ala Met Leu Ile Met Thr Met
65                  70                  75                  80

Leu Leu Ala Lys Lys Val Ala Ser His Ala Pro Ser Leu Leu Arg Asp
            85                  90                  95

Val Phe His Thr Thr Val Asn Phe Ile Asn Gln Asn Leu Phe Ser Tyr
        100                 105                 110

Val Arg Asn Leu Val Arg Asn Glu Met Asp
    115                 120

(2) INFORMATION FOR SEQ ID NO:52:

(i) SEQUENCE CHARACTERISTICS:
　　　　(A) LENGTH: 55 amino acids
　　　　(B) TYPE: amino acid
　　　　(C) STRANDEDNESS:
　　　　(D) TOPOLOGY: linear (ii) MOLECULE TYPE: protein (xi) SEQUENCE DESCRIPTION: SEQ ID NO:52:

Pro Asp Ser Glu Ser Gln Glu Glu Ile Ile His Asn Ile Ala Arg His

```
              1               5                  10                 15
    Leu Ala Gln Ile Gly Asp Glu Met Asp His Asn Ile Gln Pro Thr Leu
                    20                  25                 30

Val Arg Gln Leu Ala Ala Gln Phe Met Asn Gly Ser Leu Ser Glu Glu
                    35                  40                 45

Asp Lys Arg Asn Cys Leu Ala
                    50              55
```

(2) INFORMATION FOR SEQ ID NO:53:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

```
    Pro Asp Ser Glu Ser Gln Glu Glu Ile Ile His Asn Ile Ala Arg His
    1               5                  10                 15

Leu Ala Gln Ile Gly Asp Glu Met Asp His Asn Ile Gln Pro Thr Leu
                    20                  25                 30

Val
```

(2) INFORMATION FOR SEQ ID NO:54:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

```
    Tyr Gly Arg Lys Lys Arg Arg Gln Arg Arg Arg
    1               5                  10
```

(2) INFORMATION FOR SEQ ID NO:55:

(i) SEQUENCE CHARACTERISTICS:
        (A) LENGTH: 32 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:55:

```
    Asp Ser Glu Ser Gln Glu Glu Ile Ile His Asn Ile Ala Arg His Leu
    1               5                  10                 15

Ala Gln Ile Gly Asp Glu Met Asp His Asn Ile Gln Pro Thr Leu Val
                    20                  25                 30
```

(2) INFORMATION FOR SEQ ID NO:56:

(i) SEQUENCE CHARACTERISTICS:
        (A) LENGTH: 44 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:56:

```
    Tyr Gly Arg Lys Lys Arg Arg Gln Arg Arg Gly Asp Ser Glu Ser
    1               5                   10                  15

Gln Glu Glu Ile Ile His Asn Ile Ala Arg His Leu Ala Gln Ile Gly
                    20                  25                  30

Asp Glu Met Asp His Asn Ile Gln Pro Thr Leu Val
                35                  40
```

(2) INFORMATION FOR SEQ ID NO:57:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:57:

```
    Leu Arg Gln Ala Gly Asp Asp Phe Ser
    1               5
```

(2) INFORMATION FOR SEQ ID NO:58:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:58:

```
    Leu Lys Arg Ile Gly Asp Glu Leu Asp
    1               5
```

(2) INFORMATION FOR SEQ ID NO:59:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:59:

```
    Leu Arg Glu Ala Gly Asp Glu Phe Glu
    1               5
```

(2) INFORMATION FOR SEQ ID NO:60:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:60:

```
    Leu Arg Arg Val Gly Asp Gly Val Gln
    1               5
```

(2) INFORMATION FOR SEQ ID NO:61:

(i) SEQUENCE CHARACTERISTICS:
        (A) LENGTH: 9 amino acids
        (B) TYPE: amino acid
        (C) STRANDEDNESS:

(D) TOPOLOGY: linear (ii) MOLECULE TYPE: peptide (xi) SEQUENCE DESCRIPTION: SEQ ID NO:61:

Met Arg Val Met Gly Thr Ile Phe Glu
    1               5

(2) INFORMATION FOR SEQ ID NO:62:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:62:

Asp Gly Val Asn Trp Gly Arg Ile Val Ala
    1               5                   10

(2) INFORMATION FOR SEQ ID NO:63:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:63:

Asp Gly Asn Phe Asn Trp Gly Arg Val Val Ala
    1               5                   10

(2) INFORMATION FOR SEQ ID NO:64:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:64:

Asp Gly Val Asn Trp Gly Arg Ile Val Ala
    1               5                   10

(2) INFORMATION FOR SEQ ID NO:65:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:65:

Ser Gly Ile Asn Trp Gly Arg Val Val Ala
    1               5                   10

(2) INFORMATION FOR SEQ ID NO:66:

(i) SEQUENCE CHARACTERISTICS:
        (A) LENGTH: 11 amino acids
        (B) TYPE: amino acid
        (C) STRANDEDNESS:

(D) TOPOLOGY: linear (ii) MOLECULE TYPE: peptide (xi) SEQUENCE DESCRIPTION: SEQ ID NO:66:

Asp Gly Val Thr Asn Trp Gly Arg Ile Val Thr
    1               5                  10

(2) INFORMATION FOR SEQ ID NO:67:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:67:

Cys Pro Met Ser Tyr Gly Arg Leu Ile Gly
    1               5                  10

(2) INFORMATION FOR SEQ ID NO:68:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:68:

Asp Gly Ile Ile Asn Trp Gly Arg Ile Val Thr
    1               5                  10

(2) INFORMATION FOR SEQ ID NO:69:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:69:

Trp Ala Ala Gln Arg Tyr Gly Arg Glu Leu Arg
    1               5                  10

(2) INFORMATION FOR SEQ ID NO:70:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:70:

Asp Leu Ile Asn Trp Gly Arg Ile Cys Gly
    1               5                  10

(2) INFORMATION FOR SEQ ID NO:71:

(i) SEQUENCE CHARACTERISTICS:
        (A) LENGTH: 11 amino acids
        (B) TYPE: amino acid
        (C) STRANDEDNESS:

(D) TOPOLOGY: linear (ii) MOLECULE TYPE: peptide (xi) SEQUENCE DESCRIPTION: SEQ ID NO:71:

Arg Gly Asp Pro Ser Leu Gly Arg Ala Leu Ala
        1               5                   10

(2) INFORMATION FOR SEQ ID NO:72:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:72:

Trp Ile Gln Asp Asn Gly Gly Trp Asp
        1               5

(2) INFORMATION FOR SEQ ID NO:73:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:73:

Trp Ile Gln Asp Gln Gly Gly Trp Asp
        1               5

(2) INFORMATION FOR SEQ ID NO:74:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:74:

Trp Ile Gln Glu Asn Gly Gly Trp Asp
        1               5

(2) INFORMATION FOR SEQ ID NO:75:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:75:

Trp Ile Ala Gln Arg Gly Gly Trp Val
        1               5

(2) INFORMATION FOR SEQ ID NO:76:

(i) SEQUENCE CHARACTERISTICS:
            (A) LENGTH: 9 amino acids
            (B) TYPE: amino acid
            (C) STRANDEDNESS:

(D) TOPOLOGY: linear (ii) MOLECULE TYPE: peptide (xi) SEQUENCE DESCRIPTION: SEQ ID NO:76:

Trp Leu Val Lys Gln Arg Gly Trp Asp
        1               5

(2) INFORMATION FOR SEQ ID NO:77:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:77:

Trp Lys Glu His Asn Arg Ser Trp Asp
        1               5

(2) INFORMATION FOR SEQ ID NO:78:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:78:

Trp Ile Arg Gly Asn Gly Gly Trp Glu
        1               5

(2) INFORMATION FOR SEQ ID NO:79:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:79:

Trp Thr Arg Ile Ile Gln Ser Trp Asp
        1               5

(2) INFORMATION FOR SEQ ID NO:80:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:80:

Trp Met Ile Ser His Gly Gly Trp Glu
        1               5

(2) INFORMATION FOR SEQ ID NO:81:

(i) SEQUENCE CHARACTERISTICS:
            (A) LENGTH: 9 amino acids
            (B) TYPE: amino acid
            (C) STRANDEDNESS:

(D) TOPOLOGY: linear (ii) MOLECULE TYPE: peptide (xi) SEQUENCE DESCRIPTION: SEQ ID NO:81:

Trp Ile His Gln Gln Gly Gly Trp Asp
    1               5

(2) INFORMATION FOR SEQ ID NO:82:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:82:

Asn Arg Glu Ile Val Met Lys Tyr Ile His Tyr Lys Leu Ser Gln Arg
    1               5                   10                  15

Gly Tyr Glu Trp
                20

(2) INFORMATION FOR SEQ ID NO:83:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:83:

Asn Arg Glu Leu Val Val Asp Phe Leu Ser Tyr Lys Leu Ser Gln Lys
    1               5                   10                  15

Gly Tyr Ser Trp
                20

(2) INFORMATION FOR SEQ ID NO:84:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:84:

Trp Glu Glu Pro Arg Leu Asp Ile Glu Gly Phe Val Val Asp Tyr Phe
    1               5                   10                  15

Thr His Arg Ile Arg Gln Asn Gly Met Glu Trp
                20                  25

(2) INFORMATION FOR SEQ ID NO:85:

(i) SEQUENCE CHARACTERISTICS:
            (A) LENGTH: 18 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:85:

Ile His Asn Ala Ile Arg His Leu Ala Gln Ile Gly Asp Glu Met Asp

-continued

```
          1               5              10              15

His Asn
```

(2) INFORMATION FOR SEQ ID NO:86:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:86:

```
        Asn Ile Ala Arg His Leu Ala Gln Ile Gly Asp Glu Met Asp
        1               5                  10
```

(2) INFORMATION FOR SEQ ID NO:87:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:87:

```
        Tyr Gly Arg Lys Lys Arg Arg Gln Arg Arg Gly Ile His Asn Ile
        1               5                  10                  15

Ala Arg His Leu Ala Gln Ile Gly Asp Glu Met Asp His Asn
                       20                  25                  30
```

(2) INFORMATION FOR SEQ ID NO:88:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:88:

```
        Tyr Gly Arg Lys Lys Arg Arg Gln Arg Arg Arg Gly Asn Ile Ala Arg
        1               5                  10                  15

His Leu Ala Gln Ile Gly Asp Glu Met Asp
                       20                  25
```